US008969000B2

(12) United States Patent
Roepman et al.

(10) Patent No.: US 8,969,000 B2
(45) Date of Patent: Mar. 3, 2015

(54) PROGNOSTIC GENE EXPRESSION SIGNATURE FOR NON SMALL CELL LUNG CANCER PATIENTS

(75) Inventors: Paul Roepman, Utrecht (NL); Nico Van Zandwijk, Sydney (AU); Annuska Maria Glas, Assendelft (NL)

(73) Assignee: Agendia B.V., Amsterdam (NL)

( * ) Notice: Subject to any disclaimer, the term of this patent is extended or adjusted under 35 U.S.C. 154(b) by 322 days.

(21) Appl. No.: 12/602,287

(22) PCT Filed: Jun. 2, 2008

(86) PCT No.: PCT/NL2008/050342
§ 371 (c)(1),
(2), (4) Date: Jan. 14, 2010

(87) PCT Pub. No.: WO2008/147205
PCT Pub. Date: Dec. 4, 2008

(65) Prior Publication Data
US 2010/0184052 A1    Jul. 22, 2010

(30) Foreign Application Priority Data
Jun. 1, 2007   (EP) ................................. 07109466

(51) Int. Cl.
  *C12Q 1/68*   (2006.01)
(52) U.S. Cl.
  USPC ........................... 435/6.1; 435/6.11; 435/6.14
(58) Field of Classification Search
  USPC ........................................ 435/6.1, 6.11, 6.14
  See application file for complete search history.

(56) References Cited

U.S. PATENT DOCUMENTS

| 2003/0224509 A1 | 12/2003 | Moon et al. |
| 2004/0241725 A1 | 12/2004 | Xiao et al. |
| 2005/0272061 A1 | 12/2005 | Petroziello et al. |
| 2006/0211036 A1 | 9/2006 | Chou et al. |
| 2007/0065859 A1* | 3/2007 | Wang et al. .................. 435/6 |
| 2007/0099209 A1 | 5/2007 | Clarke et al. |

FOREIGN PATENT DOCUMENTS

EP           1541698 A2       4/2010

OTHER PUBLICATIONS

Cerutti et al. Journal of Clinical Investigation (2004) 113(8): 1234-1242.*
Adachi et al. Oncogene (2004) 23: 3495-3500.*
Potti et al. New England Journal of Medicine (2006) 355: 570-580.*
Roepman et al. Clinical Cancer Research (2009) 15(1): 284-290.*
Lau et al. Journal of Clinical Oncology (2007) 25(35): 5562-5569.*
Miyake et al., "A Novel Molecular Staging Protocol for Non-Small Cell Lung Cancer", Oncogene, vol. 18, pp. 2397-2404; 1999.
Agilent Technologies, "DNA Oligo Microarray Gene List and Annotations", Internet Article, on-line, XP002457877, retrieved from the Internet:   URL:http://www.chem.agilent.com/scripts/generic.asp?1page=5175&indocl=N&prodcol=Y> the whole document: Oct. 26, 2005.
Database Corenucleutide, on-line, "*Homosapiens* Chromosome 3 Open Reading Frame 41, transcript variant 1 (C3orf41), mRNA", XP002457709, retrieved from NCBI, Database Accession No. XM_046264, the whole document: Feb. 28, 2006.
Database Corenucleutide, on-line, "*Homosapiens* Chromosome 1 Open Reading Frame 24, (C1orf24), mRNA", XP002457710, retrieved from NCBI, Database Accession No. NM_052966, the whole document: Nov. 7, 2001.
Cancer Facts and Figures 2007, American Cancer Society, pp. 1-52.
Douillard et al., "Adjuvant Vinorelbine Plus Cisplatin Versus Observation in Patients with Completely Resected Stage IB-IIIA Non-Small-Cell Lung Cancer (Adjuvant Navelbine International Trialist Association [ANITA]): A Randomised Controlled Trial", Lancet Oncology, vol. 7, pp. 719-727; 2006.
Fan et al., "Cross-Study Validation and Combined Analysis of Microarray Data for Cancer Using Vector Cosine Angle Method", Proceedings of the 2005 IEEE, Engineering in Medicine and Biology 27th Annual Conference, pp. 4810-4813; 2005.
Glas et al., "Converting a Breast Cancer Microarray Signature into a High-Throughput Diagnostic Test", BMC Genomics, vol. 7, No. 278, pp. 1-10; 2006.
Martin-Magniette et al., "Evaluation of the Gene-Specific Dye Bias in cDNA Microarray Experiments", Bioinformatics, vol. 21, No. 9, pp. 1995-2000; 2005.
Michiels, et al., "Prediction of Cancer Outcome with Microarrays: A Multiple Random Validation Strategy", Lancet, vol. 465, pp. 488-492; 2005.
Pepe et al., "Adjuvant Vinorelbine and Cisplatin in Elderly Patients: National Cancer Institute of Canada and Intergroup Study JBR.10", Journal of Clinical Oncology, vol. 25, No. 12, pp. 1553-1561; 2007.
Veer et al., "Gene Expression Profiling Predicts Clinical Outcome of Breast Cancer", Nature, vol. 415, pp. 530-536; 2002.
Yang et al., "Normalization for cDNA Microarray Data: A Robust Composite Method Addressing Single and Multiple Slide Systematic Variation", Nucleic Acids Research, vol. 30, No. 4, pp. 1-11; 2002.
Borczuk et al., "Non-Small-Cell Lung Cancer Molecular Signatures Recapitulate Lung Developmental Pathways", American Journal of Pathology, vol. 163, No. 5, pp. 2-13 (Nov. 2003).
Kwon et al., "MUC4 Expression in Non-Small Cell Lung Carcinomas", Arch Pathol Lab Med, vol. 131, pp. 593-598 (Apr. 2007).
Sheu et al., "Development of a Membrane Array-Based Multimarker Assay for Detection of Circulating Cancel Cells in Patients with Non-Small Cell Lung Cancer", Int. J. Cancer, 119, 1419-1426 (2006).

(Continued)

*Primary Examiner* — Ardin Marschel
(74) *Attorney, Agent, or Firm* — Hoffmann & Baron, LLP

(57) ABSTRACT

The invention relates to a method of typing non-small cell lung cancer by determining RNA levels for a set of genes. The typing can be used for determining a metastasizing potential of the cancer cells. The invention further relates to a set of probes and a set of primers for typing non-small cell cancer cells.

7 Claims, 11 Drawing Sheets

(56) References Cited

OTHER PUBLICATIONS

Figure 1:
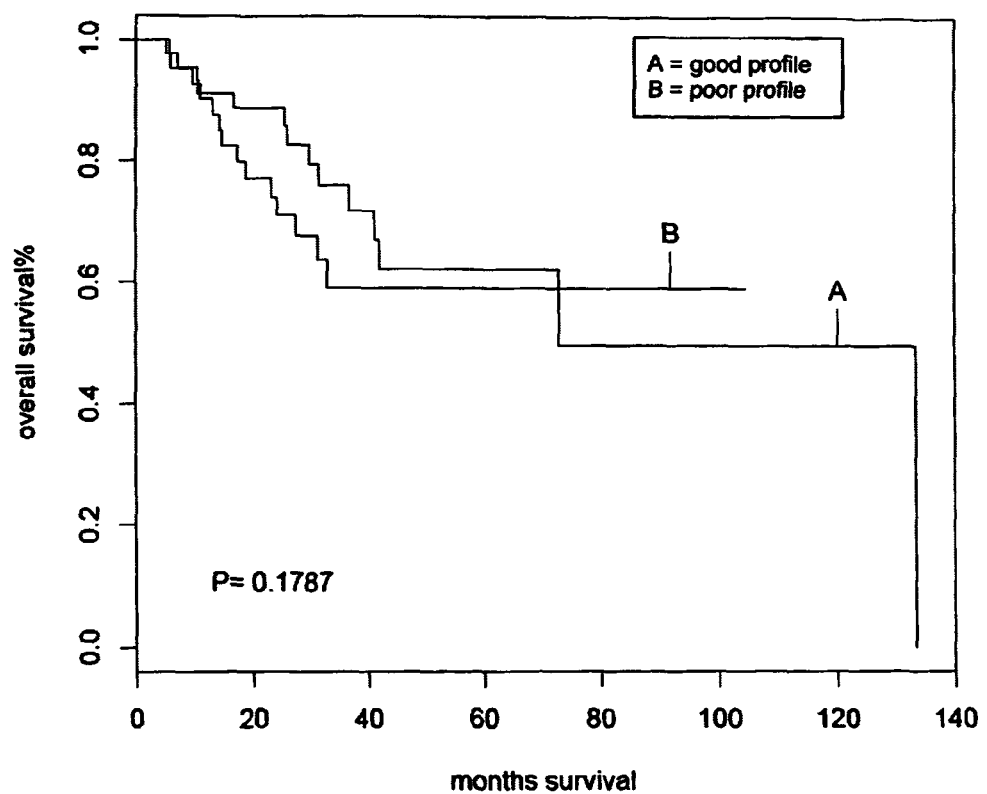

Chen et al., "Identification of Trophinin as an Enhancer for Cell Invasion and a Prognostic Factor for Early Stage Lung Cancer", Europian Journal of Cancer, 43, pp. 782-790 (2007).
Liu et al., "Identification of Genes Differentially Expressed in Human Primary Lung Squamous Cell Carcinoma", Lung Cancer, 56, pp. 307-317 (2007).
Tantipaiboonwong et al., "Different Techniques for Urinary Protein Analysis of Normal and Lung Cancer Patients", Proteomics, 5, pp. 1140-1149 (2005).
Deng et al.,"Proteomics Analysis of Stage-Specific Proteins Expressed in Human Squamous Cell Lung Carcinoma Tissues", Cancer Biomarkers, pp. 279-286 (2005).
Lu et al., "A Gene Expression Signature Predict Survival of Patients with Stage 1 Non-Small Cell Lung Cancer", PLOS Medicine, vol. 3, Issue 12, pp. 2229-2243 (Dec. 2006).
Woenickhaus et al., "Smoking and Cancer-Related Gene Expression in Bronchial Epithelium and Non-Small-Cell Lung Cancers", Journal of Pathology, 210, pp. 192-204 (2006).

* cited by examiner

SEQUENCE LISTING

<160> NUMBER OF SEQ ID NOS: 236

<210> SEQ ID NO 1
<211> LENGTH: 60
<212> TYPE: DNA
<213> ORGANISM: Homo sapiens

<400> SEQUENCE: 1
gtcaatgctg ggaagacagg agaaaagctt aattcttgac atttaaatac cagttttcca      60

<210> SEQ ID NO 2
<211> LENGTH: 60
<212> TYPE: DNA
<213> ORGANISM: Homo sapiens

<400> SEQUENCE: 2
aaaggtccaa gggaatttaa tctggaagag aacatatgcc aattttaaa ctatgacagc       60

<210> SEQ ID NO 3
<211> LENGTH: 60
<212> TYPE: DNA
<213> ORGANISM: Homo sapiens

<400> SEQUENCE: 3
tgagaaagac agcacccatt gaaacagata tgtgtgtgaa agtatatttt tcaattccag      60

<210> SEQ ID NO 4
<211> LENGTH: 60
<212> TYPE: DNA
<213> ORGANISM: Homo sapiens

<400> SEQUENCE: 4
aaagcttggt gttttctctg ggtacacccc aagcagcgtc tccttttgga tacagttatt      60

<210> SEQ ID NO 5
<211> LENGTH: 60
<212> TYPE: DNA
<213> ORGANISM: Homo sapiens

<400> SEQUENCE: 5
ttcatcgtgc tgtggaagag gaagaaagtc gcttttgacg gattgtggtg tccttttcaaa    60

<210> SEQ ID NO 6
<211> LENGTH: 60
<212> TYPE: DNA
<213> ORGANISM: Homo sapiens

-continued

<400> SEQUENCE: 6
atcgaggaat gcatcttccg ggacgttgga aacacagaca tgaagtataa gaaccgtgta    60

<210> SEQ ID NO 7
<211> LENGTH: 60
<212> TYPE: DNA
<213> ORGANISM: Homo sapiens

<400> SEQUENCE: 7
gcaagatccc ccgatcagct ttatctgcca ttgtcaatgg caagccatac aagataactt    60

<210> SEQ ID NO 8
<211> LENGTH: 60
<212> TYPE: DNA
<213> ORGANISM: Homo sapiens

<400> SEQUENCE: 8
gcaaaattgg aatgatgtaa cctgtttcct caattatttt cggatttgtg aaatggtagg    60

<210> SEQ ID NO 9
<211> LENGTH: 60
<212> TYPE: DNA
<213> ORGANISM: Homo sapiens

<400> SEQUENCE: 9
aaagcagcac catttagctg tagacccttta tcatggggtc atatattgct tcatgtgtaa    60

<210> SEQ ID NO 10
<211> LENGTH: 60
<212> TYPE: DNA
<213> ORGANISM: Homo sapiens

<400> SEQUENCE: 10
gcgacccagc atagatctat gcatccacca ctgttcatat ttccaaaagt gtgaaacaaa    60

<210> SEQ ID NO 11
<211> LENGTH: 60
<212> TYPE: DNA
<213> ORGANISM: Homo sapiens

<400> SEQUENCE: 11
cgtgaggatg cttggcacgt accccgtgta catacttccc aggcacccag catggaaata    60

<210> SEQ ID NO 12
<211> LENGTH: 60
<212> TYPE: DNA
<213> ORGANISM: Homo sapiens

<400> SEQUENCE: 12
gatgctgaac caaacttcga tgaggatggc caggatgagt acaatgagct gcacatgcca    60

<210> SEQ ID NO 13
<211> LENGTH: 60
<212> TYPE: DNA
<213> ORGANISM: Homo sapiens

<400> SEQUENCE: 13
accatagggc tatgatctgc agtagttctg tggtgaagag acttgtttca tctccggaaa    60

<210> SEQ ID NO 14
<211> LENGTH: 60
<212> TYPE: DNA

<213> ORGANISM: Homo sapiens

<400> SEQUENCE: 14
aggtctgatg cagtagcttt tactattggt ggaaatcgat gttttttcct tgaaagtcta    60

<210> SEQ ID NO 15
<211> LENGTH: 60
<212> TYPE: DNA
<213> ORGANISM: Homo sapiens

<400> SEQUENCE: 15
ggggctggaa tgggtggcag ttatatcaca tgatggaagt aataaatact acgcagactc    60

<210> SEQ ID NO 16
<211> LENGTH: 60
<212> TYPE: DNA
<213> ORGANISM: Homo sapiens

<400> SEQUENCE: 16
aacttcctac cactcaccct agcattactt atatgatatg tctccatacc cattacaatc    60

<210> SEQ ID NO 17
<211> LENGTH: 60
<212> TYPE: DNA
<213> ORGANISM: Homo sapiens

<400> SEQUENCE: 17
taatgactgc tgtacagtgg gtatagtatt ttggttttgg ttccagattg tgcaatcttt    60

<210> SEQ ID NO 18
<211> LENGTH: 60
<212> TYPE: DNA
<213> ORGANISM: Homo sapiens

<400> SEQUENCE: 18
tttgcattcc attgcatatt tccaagtcgg ctttgctata aacacaaata ttctccagaa    60

<210> SEQ ID NO 19
<211> LENGTH: 60
<212> TYPE: DNA
<213> ORGANISM: Homo sapiens

<400> SEQUENCE: 19
ctgtgttaat acacctagtg aggagtggag ctgaatttga atgcaagcct tggcaccttA    60

<210> SEQ ID NO 20
<211> LENGTH: 60
<212> TYPE: DNA
<213> ORGANISM: Homo sapiens

<400> SEQUENCE: 20
ggccatacgc catgccatag cttgtgctat ctgtaaatat gagacttgta aagaactgcc    60

<210> SEQ ID NO 21
<211> LENGTH: 60
<212> TYPE: DNA
<213> ORGANISM: Homo sapiens

<400> SEQUENCE: 21
ttgcaaattt tagggtcctg agccaagtat ggatggttca gaatttgttt ctttcctgga    60

<210> SEQ ID NO 22
<211> LENGTH: 60

```
<212> TYPE: DNA
<213> ORGANISM: Homo sapiens

<400> SEQUENCE: 22
aactctgcct ccctcaccat ctctggactg aggactgagg acgaggctga ctactactgt     60

<210> SEQ ID NO 23
<211> LENGTH: 60
<212> TYPE: DNA
<213> ORGANISM: Homo sapiens

<400> SEQUENCE: 23
tgaaaaatcc tgaggattca tcttgcacat ctgagatctg agccagtcgc tgtggttgtt     60

<210> SEQ ID NO 24
<211> LENGTH: 60
<212> TYPE: DNA
<213> ORGANISM: Homo sapiens

<400> SEQUENCE: 24
tactgatgta gccctgaggt agttcatgaa aatgctgtgc actcattcca tggaataaat     60

<210> SEQ ID NO 25
<211> LENGTH: 60
<212> TYPE: DNA
<213> ORGANISM: Homo sapiens

<400> SEQUENCE: 25
ggcccagggc ccacagccag cggtggaggt gtcttgctcc gggcccgtag cccacgccct     60

<210> SEQ ID NO 26
<211> LENGTH: 60
<212> TYPE: DNA
<213> ORGANISM: Homo sapiens

<400> SEQUENCE: 26
catcatgagg gtgttgaaaa agactgggaa tgagcaagaa tggaagatca agctgcaagt     60

<210> SEQ ID NO 27
<211> LENGTH: 60
<212> TYPE: DNA
<213> ORGANISM: Homo sapiens

<400> SEQUENCE: 27
cagcaatcat tgcagactaa ctttattagg agaagcctat gccagctggg agtgattgct     60

<210> SEQ ID NO 28
<211> LENGTH: 60
<212> TYPE: DNA
<213> ORGANISM: Homo sapiens

<400> SEQUENCE: 28
cacctagttt tctgaaaact gatttaccag gtttaggttg atgtcatcta atagtgccag     60

<210> SEQ ID NO 29
<211> LENGTH: 60
<212> TYPE: DNA
<213> ORGANISM: Homo sapiens

<400> SEQUENCE: 29
ctactgactt gtgatgctct caagcacatg atagtgggcg atgaaggtca aggaggactc     60

<210> SEQ ID NO 30
```

```
<211> LENGTH: 60
<212> TYPE: DNA
<213> ORGANISM: Homo sapiens

<400> SEQUENCE: 30
ctcccatctg aaacctgtga ctcaggttta tgaatggtgt ttgtgtagca acacattgtg      60

<210> SEQ ID NO 31
<211> LENGTH: 60
<212> TYPE: DNA
<213> ORGANISM: Homo sapiens

<400> SEQUENCE: 31
tagcagagag agactaaaca ttgtcgttag tttaccagat ccgtgatgcc acttacctgt      60

<210> SEQ ID NO 32
<211> LENGTH: 60
<212> TYPE: DNA
<213> ORGANISM: Homo sapiens

<400> SEQUENCE: 32
aggatgagcg tgagccagaa gcagctgtgt atttaaggaa acaagcgttc ctggaattaa      60

<210> SEQ ID NO 33
<211> LENGTH: 60
<212> TYPE: DNA
<213> ORGANISM: Homo sapiens

<400> SEQUENCE: 33
gtctctgctt ttcccttgag ggattgggga ggacccagtc caggcctttc taagatactc      60

<210> SEQ ID NO 34
<211> LENGTH: 60
<212> TYPE: DNA
<213> ORGANISM: Homo sapiens

<400> SEQUENCE: 34
gtctgtgcca tgttgtcaat gggtcctttc caacccaaga ggtacatttg tttttctgtt      60

<210> SEQ ID NO 35
<211> LENGTH: 60
<212> TYPE: DNA
<213> ORGANISM: Homo sapiens

<400> SEQUENCE: 35
ccccatgttt acagataccg ctaataaatt gcagtagtcc ttcccatgga gccaaagtac      60

<210> SEQ ID NO 36
<211> LENGTH: 60
<212> TYPE: DNA
<213> ORGANISM: Homo sapiens

<400> SEQUENCE: 36
gtaacatgaa gaacactcaa aaattggcaa atgtcatcag tgttttaaac agaataaaga      60

<210> SEQ ID NO 37
<211> LENGTH: 60
<212> TYPE: DNA
<213> ORGANISM: Homo sapiens

<400> SEQUENCE: 37
tcacagtgtc tgatttgtat gccatgaact ttgagccgag ggccacagac aaagatatca      60
```

```
<210> SEQ ID NO 38
<211> LENGTH: 60
<212> TYPE: DNA
<213> ORGANISM: Homo sapiens

<400> SEQUENCE: 38
caggattcct gatatagatg ccagtcataa tagatttcga gacaacagtg gccttctgat    60

<210> SEQ ID NO 39
<211> LENGTH: 60
<212> TYPE: DNA
<213> ORGANISM: Homo sapiens

<400> SEQUENCE: 39
atgatataaa tgccaactgg caagtcattc caaactgctt gaaggagtag atgaaccaga    60

<210> SEQ ID NO 40
<211> LENGTH: 60
<212> TYPE: DNA
<213> ORGANISM: Homo sapiens

<400> SEQUENCE: 40
tggggcgagc actgtgagca cctgagcatg aaactcgacg cgttcttcgg catcttcttt    60

<210> SEQ ID NO 41
<211> LENGTH: 60
<212> TYPE: DNA
<213> ORGANISM: Homo sapiens

<400> SEQUENCE: 41
cctctgaacg atcactggtt tactttctat ggatacatct ctcctccatt gagaattgat    60

<210> SEQ ID NO 42
<211> LENGTH: 60
<212> TYPE: DNA
<213> ORGANISM: Homo sapiens

<400> SEQUENCE: 42
cagaacttct tcatatgctc aagtctccag agtcactcca ttctaaggtt gatgaagctg    60

<210> SEQ ID NO 43
<211> LENGTH: 60
<212> TYPE: DNA
<213> ORGANISM: Homo sapiens

<400> SEQUENCE: 43
aaagcattta ggacttcata aagattttga tcagtgggac tgcttgattg aaggagatga    60

<210> SEQ ID NO 44
<211> LENGTH: 60
<212> TYPE: DNA
<213> ORGANISM: Homo sapiens

<400> SEQUENCE: 44
gatgttttaa ttccaaaccg gatgagtggt gaatgccaat ccccacactg ccctgggact    60

<210> SEQ ID NO 45
<211> LENGTH: 60
<212> TYPE: DNA
<213> ORGANISM: Homo sapiens

<400> SEQUENCE: 45
tttacaaact tcaatctttt ctacatggat tttgccttcc atgaaatcat acaggagtgg    60
```

```
<210> SEQ ID NO 46
<211> LENGTH: 60
<212> TYPE: DNA
<213> ORGANISM: Homo sapiens

<400> SEQUENCE: 46
cccaaggcat caagcccttc tcccgtgcac tcaataaacc ctcaataaat attctcattt      60

<210> SEQ ID NO 47
<211> LENGTH: 60
<212> TYPE: DNA
<213> ORGANISM: Homo sapiens

<400> SEQUENCE: 47
gctggtaaaa tcattggtat gttgttggag attggtaatt tggaactcct tcatatgctt      60

<210> SEQ ID NO 48
<211> LENGTH: 60
<212> TYPE: DNA
<213> ORGANISM: Homo sapiens

<400> SEQUENCE: 48
ccgatatggc tgagattgag aaattcgata agtcgaaact gaagaagaca gagatgcaag      60

<210> SEQ ID NO 49
<211> LENGTH: 60
<212> TYPE: DNA
<213> ORGANISM: Homo sapiens

<400> SEQUENCE: 49
ctgtgaaggg cagattcacc atctccacag acaactcaaa gaacacgctc tacctgcaaa      60

<210> SEQ ID NO 50
<211> LENGTH: 60
<212> TYPE: DNA
<213> ORGANISM: Homo sapiens

<400> SEQUENCE: 50
ctatattggc gagggcgaca tgaagatgca ctgctgcgtg ccgcctata tctccgacta       60

<210> SEQ ID NO 51
<211> LENGTH: 60
<212> TYPE: DNA
<213> ORGANISM: Homo sapiens

<400> SEQUENCE: 51
tttgggaagt cagccatgaa gcacatggtc atcttgttca ctcgcaaaga agagttggag      60

<210> SEQ ID NO 52
<211> LENGTH: 60
<212> TYPE: DNA
<213> ORGANISM: Homo sapiens

<400> SEQUENCE: 52
acgttacaac tgagttagaa gaatataagg aagcctttgc agcagcattg aaagctaaca      60

<210> SEQ ID NO 53
<211> LENGTH: 60
<212> TYPE: DNA
<213> ORGANISM: Homo sapiens

<400> SEQUENCE: 53
atgaactcga tgctaagcag ggtagatggt atgtggtaca aacaaattat gaccgttgga      60
```

<210> SEQ ID NO 54
<211> LENGTH: 60
<212> TYPE: DNA
<213> ORGANISM: Homo sapiens

<400> SEQUENCE: 54
gcagcaccac ttgagatttc cagaggaccc agacctttgt tcattctaaa gagactgata        60

<210> SEQ ID NO 55
<211> LENGTH: 60
<212> TYPE: DNA
<213> ORGANISM: Homo sapiens

<400> SEQUENCE: 55
acgatggtac ccagacagtc aggatggtgt cacatttta tggaaatgga gatatttgtg        60

<210> SEQ ID NO 56
<211> LENGTH: 60
<212> TYPE: DNA
<213> ORGANISM: Homo sapiens

<400> SEQUENCE: 56
tcagggaacc aaacccagaa ttcggtgcaa aagccaaaca tcttggtggg atttgataaa        60

<210> SEQ ID NO 57
<211> LENGTH: 60
<212> TYPE: DNA
<213> ORGANISM: Homo sapiens

<400> SEQUENCE: 57
gccaagaaca cgctgtatct gcaaatgaac agtctgagag ccgaggacac ggctgtgtat        60

<210> SEQ ID NO 58
<211> LENGTH: 60
<212> TYPE: DNA
<213> ORGANISM: Homo sapiens

<400> SEQUENCE: 58
tcatatacat taagttgagc catatgtaat cactgtgttt gtaggttaga aacagctgag        60

<210> SEQ ID NO 59
<211> LENGTH: 60
<212> TYPE: DNA
<213> ORGANISM: Homo sapiens

<400> SEQUENCE: 59
cctctccatg tccaggaaac ttgtaaccac ccttttctaa cagcaataaa gaggtgtcct        60

<210> SEQ ID NO 60
<211> LENGTH: 60
<212> TYPE: DNA
<213> ORGANISM: Homo sapiens

<400> SEQUENCE: 60
gacgtcattt gagaaaatga aagaaaatcc catgacaaat cgttctacag tttccaaatc        60

<210> SEQ ID NO 61
<211> LENGTH: 60
<212> TYPE: DNA
<213> ORGANISM: Homo sapiens

<400> SEQUENCE: 61

```
tgcctaaggg tggctgaaat actaaaacac tatcttacag caagtgaaca ggggctacct    60
```

<210> SEQ ID NO 62
<211> LENGTH: 60
<212> TYPE: DNA
<213> ORGANISM: Homo sapiens

<400> SEQUENCE: 62

```
agggtctcca atttaggctt tcaacattat ctctaaagaa ggttatacat tatgtcggct    60
```

<210> SEQ ID NO 63
<211> LENGTH: 60
<212> TYPE: DNA
<213> ORGANISM: Homo sapiens

<400> SEQUENCE: 63

```
ggacatggaa atgagaatag gttaaatggt gcaggtacct catagccagc tctacacaga    60
```

<210> SEQ ID NO 64
<211> LENGTH: 60
<212> TYPE: DNA
<213> ORGANISM: Homo sapiens

<400> SEQUENCE: 64

```
tgctgagttg ggttttcctt gctgctattt taaaggtgt ccagtgtgag gtgcagctgg    60
```

<210> SEQ ID NO 65
<211> LENGTH: 60
<212> TYPE: DNA
<213> ORGANISM: Homo sapiens

<400> SEQUENCE: 65

```
gttgagggtt ttacattgct gtattcaaaa aattattggt tgcaatgttg ttcacgctac    60
```

<210> SEQ ID NO 66
<211> LENGTH: 60
<212> TYPE: DNA
<213> ORGANISM: Homo sapiens

<400> SEQUENCE: 66

```
catacggttt tgtttggagg atggcttctg ctgctaaaaa tacaaaagtt tggaaaccgc    60
```

<210> SEQ ID NO 67
<211> LENGTH: 60
<212> TYPE: DNA
<213> ORGANISM: Homo sapiens

<400> SEQUENCE: 67

```
gagcccattt ctgtgagacc ctgtatttca aatttgcagc tgaaaggtgc ttgtacctct    60
```

<210> SEQ ID NO 68
<211> LENGTH: 60
<212> TYPE: DNA
<213> ORGANISM: Homo sapiens

<400> SEQUENCE: 68

```
tagtcggggg gtggctgcca gggggcaagg agaaagcacc gacaatcttt gattactgaa    60
```

<210> SEQ ID NO 69
<211> LENGTH: 60
<212> TYPE: DNA
<213> ORGANISM: Homo sapiens

<400> SEQUENCE: 69
ccatcagcag cctgcagtct gaagattttg cagtttatta ctgtcagcag tataataact    60

<210> SEQ ID NO 70
<211> LENGTH: 60
<212> TYPE: DNA
<213> ORGANISM: Homo sapiens

<400> SEQUENCE: 70
agttctcttt atcgccaaaa tcacgccaaa taataacggg acctatgcct gttttgtctc    60

<210> SEQ ID NO 71
<211> LENGTH: 60
<212> TYPE: DNA
<213> ORGANISM: Homo sapiens

<400> SEQUENCE: 71
tctgtgaatg gaactgaagt gaacgtgaat atgctgacta tatcctggaa gcatttttat    60

<210> SEQ ID NO 72
<211> LENGTH: 60
<212> TYPE: DNA
<213> ORGANISM: Homo sapiens

<400> SEQUENCE: 72
aacattgcca aagggtggca agacgtgaca gcaacatctg cttacaagaa gacatctgaa    60

<210> SEQ ID NO 73
<211> LENGTH: 60
<212> TYPE: DNA
<213> ORGANISM: Homo sapiens

<400> SEQUENCE: 73
aggcgcagaa cagagcgtta cttgataaca gcgttccatc tttgtgttgt agcagatgaa    60

<210> SEQ ID NO 74
<211> LENGTH: 60
<212> TYPE: DNA
<213> ORGANISM: Homo sapiens

<400> SEQUENCE: 74
tattccatga agtttagtat ttggttgaca tagtgctctt caaattcatc ccattaccct    60

<210> SEQ ID NO 75
<211> LENGTH: 60
<212> TYPE: DNA
<213> ORGANISM: Homo sapiens

<400> SEQUENCE: 75
tcaacccttg gaataacagt ctagctgatt gttccaccaa agaatccagc ctgctgctta    60

<210> SEQ ID NO 76
<211> LENGTH: 60
<212> TYPE: DNA
<213> ORGANISM: Homo sapiens

<400> SEQUENCE: 76
acggcttttc tattgctgta tgatacagaa ctcttttggc ataaatattt gtgttcccag    60

<210> SEQ ID NO 77
<211> LENGTH: 60
<212> TYPE: DNA
<213> ORGANISM: Homo sapiens

<400> SEQUENCE: 77
atttctttct tagttgttgg cactcttagg tcttagtatg gatttatgtg tttgtgtgtg    60

<210> SEQ ID NO 78
<211> LENGTH: 60
<212> TYPE: DNA
<213> ORGANISM: Homo sapiens

<400> SEQUENCE: 78
atgatgaaca gagttatgat tcctatgata acagctatag cacccccagcc caaagtggtg    60

<210> SEQ ID NO 79
<211> LENGTH: 60
<212> TYPE: DNA
<213> ORGANISM: Homo sapiens

<400> SEQUENCE: 79
ctctaggtcc attttcctaa ccacaagata aagatgttac attgtcaaag cttgccgtag    60

<210> SEQ ID NO 80
<211> LENGTH: 60
<212> TYPE: DNA
<213> ORGANISM: Homo sapiens

<400> SEQUENCE: 80
aaagagcctg ggtgtttggg tcagataaat gaagatcaaa ctccagctcc agcctcattt    60

<210> SEQ ID NO 81
<211> LENGTH: 60
<212> TYPE: DNA
<213> ORGANISM: Homo sapiens

<400> SEQUENCE: 81
tgctcccacg cctgcttctt aaggtccctg ctcggccggt gtaaatatgt ttcaccctgt    60

<210> SEQ ID NO 82
<211> LENGTH: 60
<212> TYPE: DNA
<213> ORGANISM: Homo sapiens

<400> SEQUENCE: 82
aatgcattga agctgttgag aaaagaggtc tagatgttga tggaatatat cgagttagtg    60

<210> SEQ ID NO 83
<211> LENGTH: 60
<212> TYPE: DNA
<213> ORGANISM: Homo sapiens

<400> SEQUENCE: 83
ttatagtggg ataattttac atcttaaata tttctttcta ctactgtaag ctctactttg    60

<210> SEQ ID NO 84
<211> LENGTH: 60
<212> TYPE: DNA
<213> ORGANISM: Homo sapiens

<400> SEQUENCE: 84
gaaagctcct aagctcctga tctatgatgc ctccagtttg gaaagtgggg tcccatcaag    60

<210> SEQ ID NO 85
<211> LENGTH: 60
<212> TYPE: DNA
<213> ORGANISM: Homo sapiens

<400> SEQUENCE: 85
ccattctatg agtggctgga actcaagtct gaatggcaga aaggcgccta cctcaaggac        60

<210> SEQ ID NO 86
<211> LENGTH: 60
<212> TYPE: DNA
<213> ORGANISM: Homo sapiens

<400> SEQUENCE: 86
aggcaggctt tttggtgcta ggccctggga ctggaagtcg cccagcccgt atttatgtaa        60

<210> SEQ ID NO 87
<211> LENGTH: 60
<212> TYPE: DNA
<213> ORGANISM: Homo sapiens

<400> SEQUENCE: 87
gacataccag tctttagctg gtgctatggt ctgttcttta gttctagttt gtatcccctc        60

<210> SEQ ID NO 88
<211> LENGTH: 60
<212> TYPE: DNA
<213> ORGANISM: Homo sapiens

<400> SEQUENCE: 88
aatcccacta atcctgatga ggctgacaaa gttggggctg agaacacaat cacctattca        60

<210> SEQ ID NO 89
<211> LENGTH: 60
<212> TYPE: DNA
<213> ORGANISM: Homo sapiens

<400> SEQUENCE: 89
aaatcgacac tgtggattga ctttcccggt cactatataa agcaaataaa cttaaaacac        60

<210> SEQ ID NO 90
<211> LENGTH: 60
<212> TYPE: DNA
<213> ORGANISM: Homo sapiens

<400> SEQUENCE: 90
atgccatatg tacagtcttg actatttctg agtcatctag tggctccaat ttgctccagg        60

<210> SEQ ID NO 91
<211> LENGTH: 60
<212> TYPE: DNA
<213> ORGANISM: Homo sapiens

<400> SEQUENCE: 91
ttttctggga aatgactttt ctgggaaatg acagtttctt tgacatattt tctttgccca        60

<210> SEQ ID NO 92
<211> LENGTH: 60
<212> TYPE: DNA
<213> ORGANISM: Homo sapiens

<400> SEQUENCE: 92
tctttatcaa agacaaccaa aagttacaac agttcagagt agcacatgag gatttcatgt        60

<210> SEQ ID NO 93
<211> LENGTH: 60
<212> TYPE: DNA

<213> ORGANISM: Homo sapiens

<400> SEQUENCE: 93
tctgttggtg tagatgcgcg tcatccttct ttcttcctct acagaagtgg tgtctactat    60

<210> SEQ ID NO 94
<211> LENGTH: 60
<212> TYPE: DNA
<213> ORGANISM: Homo sapiens

<400> SEQUENCE: 94
tttgcttgcc aaacttagct ttgccagtga tagtcaatat taaagtgtac ttttttcccc    60

<210> SEQ ID NO 95
<211> LENGTH: 60
<212> TYPE: DNA
<213> ORGANISM: Homo sapiens

<400> SEQUENCE: 95
gtattctgca cgagaaggta cactggtccc aaagtgtaaa gctttaagag tcatttatat    60

<210> SEQ ID NO 96
<211> LENGTH: 60
<212> TYPE: DNA
<213> ORGANISM: Homo sapiens

<400> SEQUENCE: 96
ggaatttctc atgaggagaa agtaaagttt ctgggcgaca attaccttga ggaaggccct    60

<210> SEQ ID NO 97
<211> LENGTH: 60
<212> TYPE: DNA
<213> ORGANISM: Homo sapiens

<400> SEQUENCE: 97
cagttgcttg atcaggtgga acagattcag aaggagcagg attaccaaag gtatcgtgaa    60

<210> SEQ ID NO 98
<211> LENGTH: 60
<212> TYPE: DNA
<213> ORGANISM: Homo sapiens

<400> SEQUENCE: 98
cccacatgca tgtctgccta tgcactgaag agctcttggc ccggcagggc cccccataaa    60

<210> SEQ ID NO 99
<211> LENGTH: 60
<212> TYPE: DNA
<213> ORGANISM: Homo sapiens

<400> SEQUENCE: 99
ctgtgaggaa cctccttacc ctgttctgga atcgctgcca gactgtagct tttaatttaa    60

<210> SEQ ID NO 100
<211> LENGTH: 60
<212> TYPE: DNA
<213> ORGANISM: Homo sapiens

<400> SEQUENCE: 100
acagcatcaa tagaaagtca tctttgagat aatttaaccc tgcctctcag agggttttct    60

<210> SEQ ID NO 101
<211> LENGTH: 60

<212> TYPE: DNA
<213> ORGANISM: Homo sapiens

<400> SEQUENCE: 101
taggtgatta tatctttggt accgtattga gaacccactc tccctccttg gaccaactct    60

<210> SEQ ID NO 102
<211> LENGTH: 60
<212> TYPE: DNA
<213> ORGANISM: Homo sapiens

<400> SEQUENCE: 102
catcactggt ctccaggctg aggacgaggc tgattattac tgcagctcat atacaagcag    60

<210> SEQ ID NO 103
<211> LENGTH: 60
<212> TYPE: DNA
<213> ORGANISM: Homo sapiens

<400> SEQUENCE: 103
ttattggcag cagttttata aagtccgtca tttgcatttg aatgtaaggc tcagtaaatg    60

<210> SEQ ID NO 104
<211> LENGTH: 60
<212> TYPE: DNA
<213> ORGANISM: Homo sapiens

<400> SEQUENCE: 104 ccttttggc atcctggctt gcctccagtt ttaggtcctt tagtttgctt ctgtaagcaa    60

<210> SEQ ID NO 105
<211> LENGTH: 60
<212> TYPE: DNA
<213> ORGANISM: Homo sapiens

<400> SEQUENCE: 105
cccgggagtg ttgcaagtta aactgatgaa aagacgttta gtatttaatt gctcctcatg    60

<210> SEQ ID NO 106
<211> LENGTH: 60
<212> TYPE: DNA
<213> ORGANISM: Homo sapiens

<400> SEQUENCE: 106
ctaacagcca gccactgccc tggaggacca gggggagagt ttggagtgaa gtttaatgtt    60

<210> SEQ ID NO 107
<211> LENGTH: 60
<212> TYPE: DNA
<213> ORGANISM: Homo sapiens

<400> SEQUENCE: 107
taccctatgt tgaacaagaa aggaccggta cccgctgcca ccaatggctg caccggtgat    60

<210> SEQ ID NO 108
<211> LENGTH: 60
<212> TYPE: DNA
<213> ORGANISM: Homo sapiens

<400> SEQUENCE: 108
tgcccggaaa aatgattaaa gcattcagtg gaagtatatc tattttgta ttttgcaaaa    60

<210> SEQ ID NO 109

```
<211> LENGTH: 60
<212> TYPE: DNA
<213> ORGANISM: Homo sapiens

<400> SEQUENCE: 109
aagatagcag ccccgtcaag cgggagtgga gaccaccaca ccctccaaac aaagcaacaa      60

<210> SEQ ID NO 110
<211> LENGTH: 60
<212> TYPE: DNA
<213> ORGANISM: Homo sapiens

<400> SEQUENCE: 110
gccacatgca gggttcagaa tagctttcaa catgtttgac actgatggca atgagatggt      60

<210> SEQ ID NO 111
<211> LENGTH: 60
<212> TYPE: DNA
<213> ORGANISM: Homo sapiens

<400> SEQUENCE: 111
tcggcaccct cagaggggga tgagtgggac cgcatgatct cggacatcag cagcgacatt      60

<210> SEQ ID NO 112
<211> LENGTH: 60
<212> TYPE: DNA
<213> ORGANISM: Homo sapiens

<400> SEQUENCE: 112
aacaaggcca cactggtgtg tctcatgaat gacttctatc tgggaatctt gacggtgacc      60

<210> SEQ ID NO 113
<211> LENGTH: 60
<212> TYPE: DNA
<213> ORGANISM: Homo sapiens

<400> SEQUENCE: 113
caccctatgg tccagggaga attcaatcac actctcttcc tcctccttat ggcccaggtt      60

<210> SEQ ID NO 114
<211> LENGTH: 60
<212> TYPE: DNA
<213> ORGANISM: Homo sapiens

<400> SEQUENCE: 114
gatctcttta ggatgactgt attttttcagt tgccgataca gcttttttgtc ctctaactgt      60

<210> SEQ ID NO 115
<211> LENGTH: 60
<212> TYPE: DNA
<213> ORGANISM: Homo sapiens

<400> SEQUENCE: 115
actgagaaca tttgcagcca cacatgtaca tatgtgtaca caggtagaca gatggacaca      60

<210> SEQ ID NO 116
<211> LENGTH: 60
<212> TYPE: DNA
<213> ORGANISM: Homo sapiens

<400> SEQUENCE: 116
atttcttgtg ggtctcctat taccagcttc taaatgaatg ttgtttttga cccagtttgt      60
```

```
<210> SEQ ID NO 117
<211> LENGTH: 60
<212> TYPE: DNA
<213> ORGANISM: Homo sapiens

<400> SEQUENCE: 117
ttactgaagc tatgctgggc aattctggca atcattaaag tgcatagatt tctatcttaa    60

<210> SEQ ID NO 118
<211> LENGTH: 60
<212> TYPE: DNA
<213> ORGANISM: Homo sapiens

<400> SEQUENCE: 118
taagctttgg aagagattac acatgatgtc tttttcttag agattcacag tgcatgttag    60

<210> SEQ ID NO 119
<211> LENGTH: 60
<212> TYPE: DNA
<213> ORGANISM: Homo sapiens

<400> SEQUENCE: 119
atatatatat ctctctattt tcacactcca ctttggaact acccaggagc cagcgccctc    60

<210> SEQ ID NO 120
<211> LENGTH: 60
<212> TYPE: DNA
<213> ORGANISM: Homo sapiens

<400> SEQUENCE: 120
tgtttgtact gatactagac catttagagc ccaatttgtg gtctaccttc agcaagtgtt    60

<210> SEQ ID NO 121
<211> LENGTH: 60
<212> TYPE: DNA
<213> ORGANISM: Homo sapiens

<400> SEQUENCE: 121
tggttctgtg cccgtctctg agacagtctc tgtgtggaat ttgccttaaa ctgaagtaaa    60

<210> SEQ ID NO 122
<211> LENGTH: 60
<212> TYPE: DNA
<213> ORGANISM: Homo sapiens

<400> SEQUENCE: 122
cgagacccac cttcctcttc ctttagcagc tgggaaattg ggggcgttta tggcgccccg    60

<210> SEQ ID NO 123
<211> LENGTH: 60
<212> TYPE: DNA
<213> ORGANISM: Homo sapiens

<400> SEQUENCE: 123
agtgaccaag ccaacactct ggtggacctt tccaagatgc agaatgtcat gtatgactta    60

<210> SEQ ID NO 124
<211> LENGTH: 60
<212> TYPE: DNA
<213> ORGANISM: Homo sapiens

<400> SEQUENCE: 124
ggagacctcc ctaccaagtg atgaaagtgt tgaaaaactt aataacaaat gcttgttggg    60
```

```
<210> SEQ ID NO 125
<211> LENGTH: 60
<212> TYPE: DNA
<213> ORGANISM: Homo sapiens

<400> SEQUENCE: 125
agaaccaacc tcccatcctg aatcgcctgg caaaaatctt ctacttcctg ggaaagcagg        60

<210> SEQ ID NO 126
<211> LENGTH: 60
<212> TYPE: DNA
<213> ORGANISM: Homo sapiens

<400> SEQUENCE: 126
tataattact ttagctgcac taacagtaca atgcttgtta atggttaata taggcagggc        60

<210> SEQ ID NO 127
<211> LENGTH: 60
<212> TYPE: DNA
<213> ORGANISM: Homo sapiens

<400> SEQUENCE: 127
tgcacaggga agctagaggt ggatacacgt gttgcaagta taaaagcatc actgggattt        60

<210> SEQ ID NO 128
<211> LENGTH: 60
<212> TYPE: DNA
<213> ORGANISM: Homo sapiens

<400> SEQUENCE: 128
ctgacttagg gttagaatgg cccaatgatc ctacaacttt ttgatgctat ttcatttgat        60

<210> SEQ ID NO 129
<211> LENGTH: 60
<212> TYPE: DNA
<213> ORGANISM: Homo sapiens

<400> SEQUENCE: 129
aggacttggg tcaacatgga ttagaagagg attttatgtt ataaagagg attttcccac         60

<210> SEQ ID NO 130
<211> LENGTH: 60
<212> TYPE: DNA
<213> ORGANISM: Homo sapiens

<400> SEQUENCE: 130
acggaagcgc agccaaaaag agctgctcaa ctacgcctgg cagcatcgag agagcaagat        60

<210> SEQ ID NO 131
<211> LENGTH: 60
<212> TYPE: DNA
<213> ORGANISM: Homo sapiens

<400> SEQUENCE: 131
gatcaagaga atatttcaga gttttggttt acacatcaag aaacagacac acatacctag       60

<210> SEQ ID NO 132
<211> LENGTH: 60
<212> TYPE: DNA
<213> ORGANISM: Homo sapiens

<400> SEQUENCE: 132
tcaatggtcc tgcaagtcca gctttaaatc aaggttcata ggaaaagaca taaatgagga      60
```

<210> SEQ ID NO 133
<211> LENGTH: 60
<212> TYPE: DNA
<213> ORGANISM: Homo sapiens

<400> SEQUENCE: 133 gacgccccc agactcacac gggggcttat ttattgcttt atttatttac ttattcattt    60

<210> SEQ ID NO 134
<211> LENGTH: 60
<212> TYPE: DNA
<213> ORGANISM: Homo sapiens

<400> SEQUENCE: 134
gtgagctaac atttgctaag cactgaattt gtctcaggca ccgtgcaagg ctctttacaa    60

<210> SEQ ID NO 135
<211> LENGTH: 60
<212> TYPE: DNA
<213> ORGANISM: Homo sapiens

<400> SEQUENCE: 135
aacagtagca taggacccta ccctctgggc caagtcaaag acattctgac atcttagtat    60

<210> SEQ ID NO 136
<211> LENGTH: 60
<212> TYPE: DNA
<213> ORGANISM: Homo sapiens

<400> SEQUENCE: 136
gagagtgagc atatcagaga ggcaaattct taaagaatga tttttaaaat cagctctagg    60

<210> SEQ ID NO 137
<211> LENGTH: 60
<212> TYPE: DNA
<213> ORGANISM: Homo sapiens

<400> SEQUENCE: 137
tttgcttttt cttcctttgg gatgtggaag ctacagaaat atttataaaa catagcttt    60

<210> SEQ ID NO 138
<211> LENGTH: 60
<212> TYPE: DNA
<213> ORGANISM: Homo sapiens

<400> SEQUENCE: 138
ctctggttgc tatatctcat caggaaattc agataatggc aaagaggatc tggagtctga    60

<210> SEQ ID NO 139
<211> LENGTH: 60
<212> TYPE: DNA
<213> ORGANISM: Homo sapiens

<400> SEQUENCE: 139
ctcttgttat catcaggttc acattaaaaa cagatactta caaactgact tgaagcacag    60

<210> SEQ ID NO 140
<211> LENGTH: 60
<212> TYPE: DNA
<213> ORGANISM: Homo sapiens

<400> SEQUENCE: 140
acaggaaacc aagggctccc ctgtggctgc agcagctctt tcagccaagc ccataaaact    60

<210> SEQ ID NO 141
<211> LENGTH: 60
<212> TYPE: DNA
<213> ORGANISM: Homo sapiens

<400> SEQUENCE: 141
gtctcaacca agtgtctgaa gtgaactttg cattgaataa attttttgcca tggaaagaac    60

<210> SEQ ID NO 142
<211> LENGTH: 60
<212> TYPE: DNA
<213> ORGANISM: Homo sapiens

<400> SEQUENCE: 142
gttcccagag atgacaaatg gagaagaaag gccatcagag caaatttggg ggtttctcaa    60

<210> SEQ ID NO 143
<211> LENGTH: 60
<212> TYPE: DNA
<213> ORGANISM: Homo sapiens

<400> SEQUENCE: 143
acactacaaa gtcatcttga gtattttaaa tcggtttgtg tagttaggtt tcccaacatc    60

<210> SEQ ID NO 144
<211> LENGTH: 60
<212> TYPE: DNA
<213> ORGANISM: Homo sapiens

<400> SEQUENCE: 144
cactaaaaac atgttttgat gctgtgtgct tttggctggg cctcgggctc caggccctgg    60

<210> SEQ ID NO 145
<211> LENGTH: 60
<212> TYPE: DNA
<213> ORGANISM: Homo sapiens

<400> SEQUENCE: 145
acgagctgct gatcaaagga cttggactaa agtctgatga acttcccaat cagatgagca    60

<210> SEQ ID NO 146
<211> LENGTH: 60
<212> TYPE: DNA
<213> ORGANISM: Homo sapiens

<400> SEQUENCE: 146
gtgatgaacc ccttggaaac cctctcaata actaactgcc ggctttcgga aggggatgtg    60

<210> SEQ ID NO 147
<211> LENGTH: 60
<212> TYPE: DNA
<213> ORGANISM: Homo sapiens

<400> SEQUENCE: 147
atgaagtcat gcgtttaatc acattcgagt gtttcagtgc ttcgcagatg tccttgatgc    60

<210> SEQ ID NO 148
<211> LENGTH: 60
<212> TYPE: DNA
<213> ORGANISM: Homo sapiens

<400> SEQUENCE: 148

```
tttttttcttt tgaagagttt taagaagttg taacttttttg tgtcttgtca tgtcagagaa    60

<210> SEQ ID NO 149
<211> LENGTH: 60
<212> TYPE: DNA
<213> ORGANISM: Homo sapiens

<400> SEQUENCE: 149
cagtcgccca agcagacagc cctggcaaat gcctgactca gtgaccagtg cctgtgagca    60

<210> SEQ ID NO 150
<211> LENGTH: 60
<212> TYPE: DNA
<213> ORGANISM: Homo sapiens

<400> SEQUENCE: 150
tcatcgtcgt gggctgcaag actgacctgc gcaaggacaa atcactggtg aacaagctcc    60

<210> SEQ ID NO 151
<211> LENGTH: 60
<212> TYPE: DNA
<213> ORGANISM: Homo sapiens

<400> SEQUENCE: 151
tggtgatggt actcctttt gcagtggaca caggactata tttctctgtg aagacaaaca    60

<210> SEQ ID NO 152
<211> LENGTH: 60
<212> TYPE: DNA
<213> ORGANISM: Homo sapiens

<400> SEQUENCE: 152
ctttggagaa cttttccgaa cacacttctt tctcaacgca ggaaacctct gcaacctcaa    60

<210> SEQ ID NO 153
<211> LENGTH: 60
<212> TYPE: DNA
<213> ORGANISM: Homo sapiens

<400> SEQUENCE: 153
attgatcaga gaccacgaaa agaaatttgt gcttcaccga agaaaaatat ctaaacatcg    60

<210> SEQ ID NO 154
<211> LENGTH: 60
<212> TYPE: DNA
<213> ORGANISM: Homo sapiens

<400> SEQUENCE: 154
tgctggtttt tcagttttca ggagtgggtt gatttcagca cctacagtgt acagtcttgt    60

<210> SEQ ID NO 155
<211> LENGTH: 60
<212> TYPE: DNA
<213> ORGANISM: Homo sapiens

<400> SEQUENCE: 155
gcattttcgt acatttttaag caaactaggt taacaacaac atagcctagt caaacttctc    60

<210> SEQ ID NO 156
<211> LENGTH: 60
<212> TYPE: DNA
<213> ORGANISM: Homo sapiens
```

<400> SEQUENCE: 156
gttcgaggtg aagaaggagc ctcccgaggc cgagcgcttc tgccaccgcc tgccgccagg    60

<210> SEQ ID NO 157
<211> LENGTH: 60
<212> TYPE: DNA
<213> ORGANISM: Homo sapiens

<400> SEQUENCE: 157
caagcttcct tctttctaac ccccagactt tggcctctga gtgaaatgtc tctctttgcc    60

<210> SEQ ID NO 158
<211> LENGTH: 60
<212> TYPE: DNA
<213> ORGANISM: Homo sapiens

<400> SEQUENCE: 158
ttgagggaaa gctacttgat caaacatccg atagtcacaa atttgaaacc gtgcttcaga    60

<210> SEQ ID NO 159
<211> LENGTH: 60
<212> TYPE: DNA
<213> ORGANISM: Homo sapiens

<400> SEQUENCE: 159
aagcagaata gatgtttgtt tttctagtgg ttataccaag ctatacttcc tgttttcacg    60

<210> SEQ ID NO 160
<211> LENGTH: 60
<212> TYPE: DNA
<213> ORGANISM: Homo sapiens

<400> SEQUENCE: 160
ttcagagtag ctcactttag tcctgtaact ttattgggtg atattttgtg ttcagtgtaa    60

<210> SEQ ID NO 161
<211> LENGTH: 60
<212> TYPE: DNA
<213> ORGANISM: Homo sapiens

<400> SEQUENCE: 161
atgaacacaa aggggaaga ggagaggcac cggtatacat tctctaggcc ttttagaaaa    60

<210> SEQ ID NO 162
<211> LENGTH: 60
<212> TYPE: DNA
<213> ORGANISM: Homo sapiens

<400> SEQUENCE: 162
ctgaaacggc aagtcagtgt atcgatttct agtgctgtga agtcagcccc tgaagaaaat    60

<210> SEQ ID NO 163
<211> LENGTH: 60
<212> TYPE: DNA
<213> ORGANISM: Homo sapiens

<400> SEQUENCE: 163
ccacatgcag ggatgcaccc acaatgtacc aaagcaggct gggcccaggg ttctatttat    60

<210> SEQ ID NO 164
<211> LENGTH: 60
<212> TYPE: DNA
<213> ORGANISM: Homo sapiens -continued

<400> SEQUENCE: 164
tttgaatcct ctggtatcaa tacgtattat agggttttag agatctgtgg gtcaaatgat    60

<210> SEQ ID NO 165
<211> LENGTH: 60
<212> TYPE: DNA
<213> ORGANISM: Homo sapiens

<400> SEQUENCE: 165
tgttccaact gtttaaaatt gatcagggac catgaaaaga aacttgtgct tcaccgaaga    60

<210> SEQ ID NO 166
<211> LENGTH: 60
<212> TYPE: DNA
<213> ORGANISM: Homo sapiens

<400> SEQUENCE: 166
ctccagggaa ggggctggag tgggtttcat acattagtag tagtagtagt accatatact    60

<210> SEQ ID NO 167
<211> LENGTH: 60
<212> TYPE: DNA
<213> ORGANISM: Homo sapiens

<400> SEQUENCE: 167
tccaagccaa caaggctaca ctggtgtgtc tcatgaatga cttttatccg ggaatcttga    60

<210> SEQ ID NO 168
<211> LENGTH: 60
<212> TYPE: DNA
<213> ORGANISM: Homo sapiens

<400> SEQUENCE: 168
ccgcaggaac cctgaggcct aggggagctg ttgagccttc agtgtctgca tgtgggaagt    60

<210> SEQ ID NO 169
<211> LENGTH: 60
<212> TYPE: DNA
<213> ORGANISM: Homo sapiens

<400> SEQUENCE: 169
atgctgttct ttagtagcaa ctaaaatgtg tcttgctgtc atttatattc cttttcccag    60

<210> SEQ ID NO 170
<211> LENGTH: 60
<212> TYPE: DNA
<213> ORGANISM: Homo sapiens

<400> SEQUENCE: 170
taatgtaatg gcatctatat tcagttgaag tgttttgatg tgcatgtgta cttcctaagg    60

<210> SEQ ID NO 171
<211> LENGTH: 60
<212> TYPE: DNA
<213> ORGANISM: Homo sapiens

<400> SEQUENCE: 171
atgccattac ctgcacattt tggatatctc tggttgtgtc ttgcttactg accaaatcct    60

<210> SEQ ID NO 172
<211> LENGTH: 60
<212> TYPE: DNA

<213> ORGANISM: Homo sapiens

<400> SEQUENCE: 172
agtagccagc agctcccaga acctcttctt ccttcttggc taactcttc cagttaggat    60

<210> SEQ ID NO 173
<211> LENGTH: 60
<212> TYPE: DNA
<213> ORGANISM: Homo sapiens

<400> SEQUENCE: 173
ttgaggttgt ctgagtcttg ggtctatgcc ttgaaaaaag ctgaattatt ggacagtctc    60

<210> SEQ ID NO 174
<211> LENGTH: 60
<212> TYPE: DNA
<213> ORGANISM: Homo sapiens

<400> SEQUENCE: 174
gggaattaaa tatgtgagtc ctcttttaa tggtgctttt tgtaaccttt aatgctgagg    60

<210> SEQ ID NO 175
<211> LENGTH: 60
<212> TYPE: DNA
<213> ORGANISM: Homo sapiens

<400> SEQUENCE: 175
actcattctt tgaatgttct cattcttttg tatcatgtga cttattaaaa tcagtttcta    60

<210> SEQ ID NO 176
<211> LENGTH: 60
<212> TYPE: DNA
<213> ORGANISM: Homo sapiens

<400> SEQUENCE: 176
aactgcttac tcaacactac cacctttcc ttatactgta tatgattatg gcctacaatg    60

<210> SEQ ID NO 177
<211> LENGTH: 60
<212> TYPE: DNA
<213> ORGANISM: Homo sapiens

<400> SEQUENCE: 177
gatgaactag agctatccaa tatggtgatt ggatggttca aacttttccc accttcctcc    60

<210> SEQ ID NO 178
<211> LENGTH: 60
<212> TYPE: DNA
<213> ORGANISM: Homo sapiens

<400> SEQUENCE: 178 gtttatatg ctggaatcca atgcagagtt ggtttgggac tgtgatcaag acaccttta    60

<210> SEQ ID NO 179
<211> LENGTH: 60
<212> TYPE: DNA
<213> ORGANISM: Homo sapiens

<400> SEQUENCE: 179
ccatgggact tttgtgagtc aggcgggaga ccattttatg tttattttct ttagtgtata    60

<210> SEQ ID NO 180
<211> LENGTH: 60

<212> TYPE: DNA
<213> ORGANISM: Homo sapiens

<400> SEQUENCE: 180
ggatttattt atagcttaac taagaatttc aaatttctac cacaacactg aaataaagtt   60

<210> SEQ ID NO 181
<211> LENGTH: 60
<212> TYPE: DNA
<213> ORGANISM: Homo sapiens

<400> SEQUENCE: 181
taagaaacat caaccaggtt gtcaagcaga gatctctgac cccttctccc atgaacatcc   60

<210> SEQ ID NO 182
<211> LENGTH: 60
<212> TYPE: DNA
<213> ORGANISM: Homo sapiens

<400> SEQUENCE: 182
ggccaaaaag ttcacagtca aatggggagg ggtattcttc atgcaggaga ccccaggccc   60

<210> SEQ ID NO 183
<211> LENGTH: 60
<212> TYPE: DNA
<213> ORGANISM: Homo sapiens

<400> SEQUENCE: 183
gaccctcgct ctctgtctcc agcagttctc tcgaatactt tgaatgttgt gtaacagtta   60

<210> SEQ ID NO 184
<211> LENGTH: 60
<212> TYPE: DNA
<213> ORGANISM: Homo sapiens

<400> SEQUENCE: 184
aatgctgtta tttttttccag atttacctgc cattgaaatt ttaaggagtt ctgtaatttc   60

<210> SEQ ID NO 185
<211> LENGTH: 60
<212> TYPE: DNA
<213> ORGANISM: Homo sapiens

<400> SEQUENCE: 185
tgccaacgga aggttcttca acaactttgc tgcaaaacat gtacatttca aggctgagca   60

<210> SEQ ID NO 186
<211> LENGTH: 60
<212> TYPE: DNA
<213> ORGANISM: Homo sapiens

<400> SEQUENCE: 186
gaagaattcg ccaagtattt aaagttgcct gtttcagatg tcttgagaca acttttttgca   60

<210> SEQ ID NO 187
<211> LENGTH: 60
<212> TYPE: DNA
<213> ORGANISM: Homo sapiens

<400> SEQUENCE: 187
ctgtctcatc ttgatagtca ttttcatgat cacaaaattt ttccaggata gacatagagc   60

<210> SEQ ID NO 188

<210> SEQ ID NO 188
<211> LENGTH: 60
<212> TYPE: DNA
<213> ORGANISM: Homo sapiens

<400> SEQUENCE: 188
tgctgtgatt gtatccgaag tagtcctcgt gagaaaagat aatgagatga cgtgagcagc    60

<210> SEQ ID NO 189
<211> LENGTH: 60
<212> TYPE: DNA
<213> ORGANISM: Homo sapiens

<400> SEQUENCE: 189
aggaagagtc aacagacttt agcaaaatcc ttttatttga ttcatgcata actcctgatg    60

<210> SEQ ID NO 190
<211> LENGTH: 60
<212> TYPE: DNA
<213> ORGANISM: Homo sapiens

<400> SEQUENCE: 190
agccttccca agacatggat tccttcccag ggagacaaag ccctgtcagg agcacagcat    60

<210> SEQ ID NO 191
<211> LENGTH: 60
<212> TYPE: DNA
<213> ORGANISM: Homo sapiens

<400> SEQUENCE: 191
ttcatgtctg tgaagctttt aaacattaca cttgagatca gtcatgactt gatattcagg    60

<210> SEQ ID NO 192
<211> LENGTH: 60
<212> TYPE: DNA
<213> ORGANISM: Homo sapiens

<400> SEQUENCE: 192
tcctcaccca cctcttcact ctgaatcctc atgaggcttc tcagccctgg atttcctgct    60

<210> SEQ ID NO 193
<211> LENGTH: 60
<212> TYPE: DNA
<213> ORGANISM: Homo sapiens

<400> SEQUENCE: 193
tgttattgaa gatgatagga ttgatgacgt gctgaaaaat atgaccgaca aggcacctcc    60

<210> SEQ ID NO 194
<211> LENGTH: 60
<212> TYPE: DNA
<213> ORGANISM: Homo sapiens

<400> SEQUENCE: 194
tgtaaccata tttgcatttg aaggtattct catcaagaaa cttctacgac agcaaattgc    60

<210> SEQ ID NO 195
<211> LENGTH: 60
<212> TYPE: DNA
<213> ORGANISM: Homo sapiens

<400> SEQUENCE: 195
tcttgtgtat ttattacatt ttcacgtgtc ttcacgcatc tcttgaattg gaaattgtgc    60

<210> SEQ ID NO 196
<211> LENGTH: 60
<212> TYPE: DNA
<213> ORGANISM: Homo sapiens

<400> SEQUENCE: 196
caaagtggca taaaaaacat gtggttacac agtgtgaata aagtgctgcg gagcaagagg    60

<210> SEQ ID NO 197
<211> LENGTH: 60
<212> TYPE: DNA
<213> ORGANISM: Homo sapiens

<400> SEQUENCE: 197
ttgcagtaat gatatttatt aaaaacccat aactaccagg ataatgata cctcccaccc     60

<210> SEQ ID NO 198
<211> LENGTH: 60
<212> TYPE: DNA
<213> ORGANISM: Homo sapiens

<400> SEQUENCE: 198
gaggggctta ttctgcctga gacacttcct ctcactaaga cagaggaaca aattctgaaa    60

<210> SEQ ID NO 199
<211> LENGTH: 60
<212> TYPE: DNA
<213> ORGANISM: Homo sapiens

<400> SEQUENCE: 199
ggtactagtt tgtatgtatg tttaaagtat gtattgacca tgagatttcc cagtgtttgg    60

<210> SEQ ID NO 200
<211> LENGTH: 60
<212> TYPE: DNA
<213> ORGANISM: Homo sapiens

<400> SEQUENCE: 200
actcggttct ccaggcctga ttccccgact ccatccttt tcagggttat ttaaaaatct     60

<210> SEQ ID NO 201
<211> LENGTH: 60
<212> TYPE: DNA
<213> ORGANISM: Homo sapiens

<400> SEQUENCE: 201
atgaccaagt gaaggaacta atggactgta ttgaggatct gttgatggag aaaaatggtg    60

<210> SEQ ID NO 202
<211> LENGTH: 60
<212> TYPE: DNA
<213> ORGANISM: Homo sapiens

<400> SEQUENCE: 202
gttggaccac aaactatgca cagaagtttc aggggaaggt caccatgacc aaggacacgt    60

<210> SEQ ID NO 203
<211> LENGTH: 60
<212> TYPE: DNA
<213> ORGANISM: Homo sapiens

<400> SEQUENCE: 203
gctgtgcacc ttcatgtggt ccgaaatata agccgagctc agcatcttgc cacacacgtg    60

<210> SEQ ID NO 204
<211> LENGTH: 60
<212> TYPE: DNA
<213> ORGANISM: Homo sapiens

<400> SEQUENCE: 204
ctcataagtg gggctatact gtgaagggca ttcagaaata caaagcaaag gttatttccg    60

<210> SEQ ID NO 205
<211> LENGTH: 60
<212> TYPE: DNA
<213> ORGANISM: Homo sapiens

<400> SEQUENCE: 205
aacacaggtc tattgactca cacacatgtt ttaagatgga aaactttact tctgttcttg    60

<210> SEQ ID NO 206
<211> LENGTH: 60
<212> TYPE: DNA
<213> ORGANISM: Homo sapiens

<400> SEQUENCE: 206
ccaacgcgca cggccgcgct ttcttcgccg ccgccttcca ccgcgtcggg ccgccgctgc    60

<210> SEQ ID NO 207
<211> LENGTH: 60
<212> TYPE: DNA
<213> ORGANISM: Homo sapiens

<400> SEQUENCE: 207
caaaataaga actatagagt tagacgggaa aacaatcaag cttcaaatat gggacacagc    60

<210> SEQ ID NO 208
<211> LENGTH: 60
<212> TYPE: DNA
<213> ORGANISM: Homo sapiens

<400> SEQUENCE: 208
catttctaac aagcatcttc ttaaccaact ttatgcacag tgtatgtttg taagtgcttc    60

<210> SEQ ID NO 209
<211> LENGTH: 60
<212> TYPE: DNA
<213> ORGANISM: Homo sapiens

<400> SEQUENCE: 209
ttgactacca ttttcctgtg tacttcatct atttgtgtac aaaatgatgt cgttttgagg    60

<210> SEQ ID NO 210
<211> LENGTH: 60
<212> TYPE: DNA
<213> ORGANISM: Homo sapiens

<400> SEQUENCE: 210
ttatcatggg aaagtattct cttttcaaga agttctttga ttctgtaata actagaacaa    60

<210> SEQ ID NO 211
<211> LENGTH: 60
<212> TYPE: DNA
<213> ORGANISM: Homo sapiens

<400> SEQUENCE: 211
gtatgtcttg agaaagaaat cacagaagca tttctcacca atactctttg gcttaaaatg    60

<210> SEQ ID NO 212
<211> LENGTH: 60
<212> TYPE: DNA
<213> ORGANISM: Homo sapiens

<400> SEQUENCE: 212
aagcgctgcc ggcagggctc cgcgacctcg gcctcctccg ccgggccgca ctcagcagcc    60

<210> SEQ ID NO 213
<211> LENGTH: 60
<212> TYPE: DNA
<213> ORGANISM: Homo sapiens

<400> SEQUENCE: 213
cgggcacatg gacatgggcg ccgaggccct gcccggcccc gacgaggccg ccgctgccgc    60

<210> SEQ ID NO 214
<211> LENGTH: 60
<212> TYPE: DNA
<213> ORGANISM: Homo sapiens

<400> SEQUENCE: 214
cattcaaaga atactagaat ggtagcacta cccggccgga gccgcccacc gtcttgggtc    60

<210> SEQ ID NO 215
<211> LENGTH: 60
<212> TYPE: DNA
<213> ORGANISM: Homo sapiens

<400> SEQUENCE: 215
acggagcctc gggctacggt cccgccggct cacttgcccc gctgcccggc agctccggag    60

<210> SEQ ID NO 216
<211> LENGTH: 60
<212> TYPE: DNA
<213> ORGANISM: Homo sapiens

<400> SEQUENCE: 216
accttaatta cactcccgca acacagccat tattttattg tctagctcca gttatctgta    60

<210> SEQ ID NO 217
<211> LENGTH: 60
<212> TYPE: DNA
<213> ORGANISM: Homo sapiens

<400> SEQUENCE: 217
tggggacagc ttcttcctag gtgaggaaaa tacaggtcat gaagttcctg gcaaagattt    60

<210> SEQ ID NO 218
<211> LENGTH: 60
<212> TYPE: DNA
<213> ORGANISM: Homo sapiens

<400> SEQUENCE: 218
agaaatgaag cccggcccac acccgacacc agccctgctg cttcctaact tattgcctgg    60

<210> SEQ ID NO 219
<211> LENGTH: 60
<212> TYPE: DNA
<213> ORGANISM: Homo sapiens

<400> SEQUENCE: 219

```
cccgccccac gagtgggtct tcgcagggcc ccctctgacg cacacgggga ccagccacgc    60
```

\<210\> SEQ ID NO 220
\<211\> LENGTH: 60
\<212\> TYPE: DNA
\<213\> ORGANISM: Homo sapiens

\<400\> SEQUENCE: 220

```
cctcagtgat gcattagatc tctaataaag tctgtatata catgtacact ttgatcctgc    60
```

\<210\> SEQ ID NO 221
\<211\> LENGTH: 60
\<212\> TYPE: DNA
\<213\> ORGANISM: Homo sapiens

\<400\> SEQUENCE: 221

```
agacggtcag ctctcatgct tgctgtatac tatgactcac caggtattgt cagtatcctt    60
```

\<210\> SEQ ID NO 222
\<211\> LENGTH: 60
\<212\> TYPE: DNA
\<213\> ORGANISM: Homo sapiens

\<400\> SEQUENCE: 222

```
tcaaccacag cggggacctg aaccacctcc ccggccacac gttcgcggcc cagcagcaaa    60
```

\<210\> SEQ ID NO 223
\<211\> LENGTH: 60
\<212\> TYPE: DNA
\<213\> ORGANISM: Homo sapiens

\<400\> SEQUENCE: 223

```
tgtggaagat actttgaaat cactttctac tttgttagta aagttctgtc tttccagagc    60
```

\<210\> SEQ ID NO 224
\<211\> LENGTH: 60
\<212\> TYPE: DNA
\<213\> ORGANISM: Homo sapiens

\<400\> SEQUENCE: 224

```
ctcatctgtg ctgaaagacg ctgaaactgc ctgggatgtt ttcgggaaca agaatgtata    60
```

\<210\> SEQ ID NO 225
\<211\> LENGTH: 60
\<212\> TYPE: DNA
\<213\> ORGANISM: Homo sapiens

\<400\> SEQUENCE: 225

```
tacgtgtgcg accgctgcgc caagcgcttc acccgccgct cggacttggt cacccaccag    60
```

\<210\> SEQ ID NO 226
\<211\> LENGTH: 60
\<212\> TYPE: DNA
\<213\> ORGANISM: Homo sapiens

\<400\> SEQUENCE: 226

```
acacgtctgt ttagcccgca attggaaagg atatatgtgg caatattaac ctggtacatg    60
```

\<210\> SEQ ID NO 227
\<211\> LENGTH: 60
\<212\> TYPE: DNA
\<213\> ORGANISM: Homo sapiens

\<400\> SEQUENCE: 227 ctatttgcga cacgaactgt gcccaatgtg tgcccaagga caaggctatt aacaaattca    60

<210> SEQ ID NO 228
<211> LENGTH: 60
<212> TYPE: DNA
<213> ORGANISM: Homo sapiens

<400> SEQUENCE: 228
cttcggagca accttcaaga gatctttcta cctgcctttc catgtcatga gaggaagaaa    60

<210> SEQ ID NO 229
<211> LENGTH: 60
<212> TYPE: DNA
<213> ORGANISM: Homo sapiens

<400> SEQUENCE: 229
aaagcgcctc ctccgccgct cccgctcggg ggacgtgctg gccaagaacc ctgtggtgcg    60

<210> SEQ ID NO 230
<211> LENGTH: 60
<212> TYPE: DNA
<213> ORGANISM: Homo sapiens

<400> SEQUENCE: 230
catccctcac cccaccaagg accacactgt gaagtgataa ctgccttgaa ccccccttttg   60

<210> SEQ ID NO 231
<211> LENGTH: 60
<212> TYPE: DNA
<213> ORGANISM: Homo sapiens

<400> SEQUENCE: 231
cgttgcttta gggcaggatt ctattttgag ggaaaagaca gtatccttat tacctttttgt   60

<210> SEQ ID NO 232
<211> LENGTH: 60
<212> TYPE: DNA
<213> ORGANISM: Homo sapiens

<400> SEQUENCE: 232
tgaaccagtc tgtaagattt ttgttagcag aagaatttta cctattgcat ggaaagatgc    60

<210> SEQ ID NO 233
<211> LENGTH: 60
<212> TYPE: DNA
<213> ORGANISM: Homo sapiens

<400> SEQUENCE: 233
acgaatgtac taccgaagga aagaccacaa ggttgggtat gaaactttct cttctccaga    60

<210> SEQ ID NO 234
<211> LENGTH: 60
<212> TYPE: DNA
<213> ORGANISM: Homo sapiens

<400> SEQUENCE: 234
cttttagctg tttaactttg taagatgcaa agaggttgga tcaagtttaa atgactgtgc    60

<210> SEQ ID NO 235
<211> LENGTH: 60
<212> TYPE: DNA
<213> ORGANISM: Homo sapiens

```
<400> SEQUENCE: 235
tgggaaacat gcgtgtgacc tccacagcta cctcttctat ggactggttg ttgccaaaca    60

<210> SEQ ID NO 236
<211> LENGTH: 60
<212> TYPE: DNA
<213> ORGANISM: Homo sapiens

<400> SEQUENCE: 236
gggtcccacg aatttgctgg ggaatctcgt ttttcttctt aagacttttg ggacatggtt    60
```

PROGNOSTIC GENE EXPRESSION SIGNATURE FOR NON SMALL CELL LUNG CANCER PATIENTS

This application is the U.S. National Phase of, and Applicants claim priority from, International Application Number PCT/NL2008/050342 filed 2 Jun. 2008 and European Patent Application No. 07109466.8 filed 1 Jun. 2007, each of which are incorporated herein by reference.

BACKGROUND OF THE INVENTION

Field

The present invention relates to the field of cancer prognosis and diagnosis. More particular, the invention relates to a method for typing an RNA sample of an individual suffering from non-small cell lung cancer. The invention furthermore relates to a set of genes or probes for use in typing an RNA sample of said individual.

Lung cancer accounts for about 15% of all diagnosed cancers in human and causes the most cancer-related deaths in both men and women (source: Cancer facts and Figures 2007, American Cancer Society). The three main types of primary lung cancers are mesothelioma, small cell lung cancer, and non-small cell lung cancer. Mesothelioma is a rare type of cancer which affects the covering of the lung (the pleura). It is often caused by exposure to asbestos. Small cell lung cancer (SCLC), also called oat cell lung cancer, is characterized by the presence of small cells that are almost entirely composed of a nucleus. SCLC frequently occurs in (ex)smokers and is quite rare for people that never smoked. SCLC tends to spread early in development of the tumor and is often treated with chemotherapy rather than surgery. Non-small cell lung cancer (NSCLC) is the most common form of lung cancer and is diagnosed in about 85% of all lung cancer patients. NSCLC represents a diverse group of cancers with the main groups being squamous cell carcinoma, adenocarcinoma, and large cell carcinoma. Other, minor groups comprise pleomorphic carcinoma, carcinoid tumor, salivary gland carcinoma, and unclassified carcinoma.

Adenocarcinoma is the most common subtype of NSCLC, accounting for 50% to 60% of NSCLC. It is a form which starts near the gas-exchanging surface of the lung. Most cases of the adenocarcinoma are associated with smoking.

However, among non-smokers and in particular female non-smokers, adenocarcinoma is the most common form of lung cancer. A subtype of adenocarcinoma, the bronchioalveolar carcinoma, is more common in female non-smokers and may have different responses to treatment. Squamous cell carcinoma, accounting for 20% to 25% of NSCLC, also starts in the larger breathing tubes but grows slower meaning that the size of these tumours varies on diagnosis. Large-cell carcinoma accounts for about 10% to 15% of NSCLC. It can start in any part of the lung. It tends to grow and spread quickly.

Known risk factors for developing NSCLC are smoking, actively or passively, exposure to air pollution, and exposure to radiation. When smoking is combined with other risk factors, the risk of developing lung cancer is increased.

There are multiple tests and procedures to detect, diagnose, and stage non-small cell lung cancer. Performing a chest X-ray is often the first step if a patient reports symptoms that may be suggestive of lung cancer. This may reveal an obvious mass, widening of the mediastinum (suggestive of spread to lymph nodes there), atelectasis (collapse), consolidation (infection) and pleural effusion. If there are no X-ray findings but the suspicion is high (e.g. a heavy smoker with blood-stained sputum), bronchoscopy and/or a CT scan may provide the necessary information. In any case, bronchoscopy or CT-guided biopsy is nearly always performed to identify the tumor type and to determine the stage.

If investigations have confirmed lung cancer, scan results; and often positron emission tomography (PET) are used to determine whether the disease is localized and amenable to surgery or whether it has spread to the point it cannot be cured surgically.

Prognosis and treatment options depend on the stage of the cancer, the type of cancer, and the patient's general health. Early stage cancer is primarily treated by surgery, which is aimed at removing all cancer cells. Surgery can lead to the removal of all or part of a lung, depending on the location and size of the cancer.

Alternative treatment is provided by radiation therapy, or radiotherapy, comprising three-dimensional conformal radiation therapy and brachytherapy; and chemotherapy including photodynamic therapy.

In general, small-cell lung cancer (SCLC) is most commonly treated by chemotherapy in an attempt to slow or halt its spread beyond the lungs. Early stage non-small-cell lung cancer (NSCLC) is first treated by surgery and additional radiation therapy and chemotherapy to slow tumor growth and relieve symptoms, if required.

After surgery, if lymph nodes are positive in the resected lung tissues (stage II) or the mediastinum (peri-tracheal region, stage III), adjuvant chemotherapy may improve survival by up to 15%. However, the benefit of adjuvant chemotherapy for patients with stage I NSCLC is still controversial. Trials of preoperative chemotherapy in resectable NSCLC have been inconclusive (source: Clinical Evidence: concise, BMJ Publishing Group, London. 2006. ISBN 1-90554501206 ISSN 1465-9225). In the NCI Canada study JBR.10 (Pepe C. et al., J Clin Oncol. 2007; 25(12): 1553-61) patients with stage IB to IIB NSCLC were treated with vinorelbine and cisplatin chemotherapy and showed a significant survival benefit of 15% over 5 years. However subgroup analysis of patients in stage IB showed that chemotherapy did not result in any significant survival gain. Similarly, while the Italian ANITA study showed a survival benefit of 8% over 5 years with vinorelbine and cisplatin chemotherapy in stages IB to IIIA, subgroup analysis also showed no benefit in the IB stage (Douillard, J U. et al., Lancet Oncol 2006; 7(9): 719-27).

A Cancer and Leukemia Group B (CALGB) study (protocol 9633), related to a randomized trial of carboplatin and paclitaxel in stage IB NSCLC, reported no survival advantage at the June 2006 American Society of Clinical Oncology meeting. However, subgroup analysis suggested benefit for tumors greater than 4 centimeters. For patients with resected stage II-IIIA NSCLC, standard practice is to offer adjuvant third generation platinum-based chemotherapy (e.g. cisplatin and vinorelbine).

Chemotherapeutic drugs that are used in lung cancer treatment comprise platinum alkylators, podophyllin alkaloids, vinca alkaloids, anthracyclines, topoisomerase inhibitors, taxanes, antimetabolites, tyrosine kinase inhibitors, and folate antagonists in recent years, various molecular targeted therapies have been developed for the treatment of advanced lung cancer. Gefitinib (Iressa) targets the epidermal growth factor receptor (EGF-R) that is expressed in many cases of NSCLC. However it was not shown to increase survival, although females, Asians, non-smokers and those with the adenocarcinoma cell type appear to benefit from gefitinib.

Another drug called erlotinib (Tarceva), which also inhibits EGF-R, increases survival in lung cancer patients and has recently been approved by the FDA for second-line treatment of advanced non-small cell lung cancer.

The most common treatment for early stage SCLC is surgery if the cancer is confined to a single nodule. Surgery can be combined with either cisplatin or carboplatin together with etoposide. Chemotherapy in combination with radiation therapy improves the outcome of the therapy. Late stage SCLC is also treated by a combination of either cisplatin or carboplatin and etoposide. Other chemotherapeutic drugs, such as cyclophosphamide, doxorubicin, vincristine, ifosfamide, topotecan, paclitaxel, methotrexate, vinorelbine, gemcitabine, irinotecan and docetaxel in various combinations, are prescribed if SCLC becomes resistant to the aforementioned drugs. Metastasis to the brain, which often occurs in SCLC is treated by radiation therapy.

Treatment of NSCLC is primarily determined by the stage of the cancer. Stage 0 cancer, in which the cancer has not spread beyond the inner lining of the lung, is often curable by surgery alone. Treatment of stage 1 cancer, which has not spread to the lymph nodes, is often also limited to surgery, either lobectomy or segmentectomy. The 5-year survival rate of patients with stage 1 is 55-70%. For stage 2 cancer, in which the cancer has spread to some lymph nodes, nowadays surgery is almost always followed by chemotherapy. Stage 3 cancer, in which the cancer has spread to nearby tissue or to distant lymph nodes, and stage 4 cancer, in which the cancer has spread to distant organs, are treated by a combination of chemotherapy and radiation therapy. Surgery is sometimes performed to remove one or more localized cancer nodules.

Chemotherapy, including adjuvant therapy, usually causes side effects, such as nausea, vomiting, loss of appetite, loss of hair, mouth sores, and severe diarrhea. For all patients, the risk of cancer recurrence has to be weighted against the severe side effects caused by aggressive treatment. This especially accounts for stage 1 NSCLC patients, where the cancer has spread beyond the inner lining of the lung, but yet has not reached the lymph nodes. Patients with an increased risk for cancer recurrence will benefit from adjuvant therapy, while patients with a reduced risk will unnecessary suffer from the severe side effects caused by adjuvant therapy. Therefore, there is a need for a method of typing NSCLC patients to determine their risk of cancer recurrence.

DESCRIPTION OF THE INVENTION

Therefore, the invention provides a method for typing, a sample, preferably a RNA sample, of an individual suffering from non-small cell lung cancer or suspected of suffering there from, the method comprising providing a tissue sample from said individual comprising non-small cell lung cancer cells or suspected to comprise non-small cell lung cancer cells; preparing RNA from said tissue sample; determining RNA levels for a set of genes in said RNA; and typing said sample on the basis of the levels of RNA determined for said set of genes; wherein said set of genes comprises at least two of the genes listed in Table 3.

A level of RNA refers to the amount of RNA that is present in a sample, preferably relative to other RNA in said sample. Said level of RNA is a measure of the level of expression of a gene in cell of said tissue sample. It is preferred that said level of RNA refers to the amount of mRNA transcripts from a gene in a sample, preferably relative to other mRNA such as total mRNA.

The genes listed in Table 3 were identified and validated as being differentially expressed in non-small cell lung cancer samples. Non-small cell lung cancer samples were randomly divided into a training set and a validation set. In a first series of experiments, genes were identified of which the RNA level differs between a sample from an individual with a high risk for cancer recurrence versus a sample from an individual with a low risk of cancer recurrence, using the training set of cancer samples. The resulting genes were validated in a second series of experiments using the independent validation set of non small cell lung cancer samples. A gene set comprising at least two of the genes listed in Table 3 provides a prognostic signature for typing a sample of an individual suffering from non-small cell lung cancer as having a low risk or an enhanced risk of cancer recurrence. Prognostic information that can be obtained by a method of the invention comprises three possible endpoints, which are time from surgery to distant metastases, time of disease-free survival, and time of overall survival. Kaplan-Meier plots (Kaplan and Meier. J Am Stat Assoc 53: 457-481 (1958)) can be used to display time-to-event curves for any or all of these three endpoints.

Typing refers to assessing a risk of recurrence of said non-small cell lung cancer. Said typing is intended to provide prognostic information to aid in clinical evaluation of NSCLC patients. In this respect, no recurrence within a relevant time interval is defined as "low risk", and recurrence within said relevant time interval is defined as "high risk". A relevant time interval is at least 1 year, more preferred at least two years, more preferred at least three years, more preferred at least five years, or more preferred at least ten years.

A method of the invention is particularly suited to differentiate between a high or low risk of recurrence within three years.

Cancer recurrence refers to a recurrence of the cancer in the same place as the original cancer or elsewhere in the body. A local recurrence refers to a cancer that has returned in or very close to the same place as the original cancer, while a distant recurrence means the cancer has spread, or metastasized, to organs or tissues distant from the site of the original cancer.

Said tissue sample can be derived from all or part of a cancerous growth, or of a tumor suspected to be cancerous, depending on the size of the cancerous growth. A cancerous growth can be removed by surgical treatment including lobectomy, bilobectomy or pneumonectomy, with or without part of a bronchial tube. Said tissue sample can also be derived by biopsy, comprising aspiration biopsy, needle biopsy, incisional biopsy, and excisional biopsy. It is preferred that at least 10% of the cells in a tissue sample are NSCLC cells, more preferred at least 20%, and most preferred at least 30%. Said percentage of tumor cells can be determined by analysis of a stained section, for example hematoxylin and eosin-stained section, from the cancerous growth. Said analysis can be performed or confirmed by a pathologist.

Said individual suffering from NSCLC, or suspected of suffering from NSCLC, can be an individual suffering from stage 0 cancer, in which the cancer has macroscopically not spread beyond the inner lining of the lung, and which is often curable by surgery alone. Said individual can be suffering from stage 1 cancer, which has not spread to the lymph nodes; stage 2 cancer, in which the cancer has spread to some lymph nodes; stage cancer, in which the cancer has spread to nearby tissue or to distant lymph nodes; or stage 4 cancer, in which the cancer has spread to distant organs.

It is preferred that said individual suffers from early stage NSCLC, or suspected of suffering there from. Early stage NSCLC is stage 0 cancer, stage 1 cancer, or stage 2 cancer.

In a preferred embodiment, said individual is suffering from stage 1 NSCLC, or suspected of suffering there from.

A method of the invention is preferably used to determine a risk for said patient for recurrence of the cancer. This risk may further be combined with other prognostic factors such as age, sex, tumor diameter and smoking history. A determined risk can be used by a clinician to make a decision about which patients may benefit from additional chemotherapy, and which patients are not likely to benefit from additional chemotherapy.

RNA prepared from said tissue sample preferably represents a quantitative copy of genes expressed at the time of collection of a tissue sample from the cancer. This can be achieved by processing and storing said tissue sample under protective conditions that preserve the quality of the RNA. Examples of such preservative conditions are fixation using e.g. formaline, the use of RNase inhibitors such as RNAsin™ (Pharmingen) or RNAsecure™ (Ambion), and the use of preservative solutions such as RNAlater™ (Ambion) and RNARetain™ (Assuragen). It is further preferred that said preservative condition allows storage and transport of said tissue sample at room temperature. A preferred preservative condition is the use of RNARetain™ (Assuragen).

Said RNA sample can be isolated from said tissue sample by any technique known in the art, including but not limited to Trizol (Invitrogen; Carlsbad, Calif.), RNAqueous® Technology (Qiagen; Venlo, the Netherlands), Total RNA Isolation method (Agilent; Santa Clara, Calif.), and Maxwell™ 16 Total RNA Purification Kit (Promega; Madison, Wis.). A preferred RNA isolation procedure involves the use of RNAqueous® Technology (Qiagen; Venlo, the Netherlands).

For each of the genes listed in Table 3, a relative level of expression in a sample from an individual with a low risk of cancer recurrence was compared to the average level of expression in a reference sample comprising a mixture of non-small cell lung cancer samples. Said relative level of expression is either increased in a low risk NSCLC sample, as indicated with a positive number in the second column of Table 3, or said relative level of expression is decreased in a low risk NSCLC sample, as indicated with a negative number in the second column of Table 3.

In a preferred embodiment, one of said at least two genes is increased in a low risk NSCLC sample, compared to the average level of expression of said gene in a reference sample, while a second gene from said at least two genes is decreased in a low risk NSCLC sample compared to the average level of expression of said gene in a reference sample.

It is furthermore preferred that said set of genes comprises at least three of the genes hated in Table 3, more preferred four of the genes listed in Table 3, more preferred five of the genes listed in Table 3, more preferred six of the genes listed in Table 3, more preferred seven of the genes listed in Table 3, more preferred eight of the genes listed in Table 3, more preferred nine of the genes listed in Table 3, more preferred ten of the genes listed in Table 3, more preferred fifteen of the genes listed in Table 3, more preferred twenty of the genes listed in Table 3, more preferred thirty of the genes listed in Table 3, more preferred forty of the genes listed in Table 3, more preferred sixty of the genes listed in Table 3, more preferred seventy of the genes listed in Table 3, more preferred seventy-two of the genes listed in Table 3, more preferred eighty of the genes listed in Table 3, more preferred ninety of the genes listed in Table 3, more preferred hundred of the genes listed in Table 3, more preferred two-hundred of the genes listed in Table 3, more preferred all of the genes listed in Table 3.

It is furthermore preferred to select genes that are increased in a low risk NSCLC sample, compared to the average level of expression of said gene in a reference sample, as well as genes that are decreased in a low risk NSCLC sample compared to the average level of expression of said gene in a reference sample.

Figure 9:
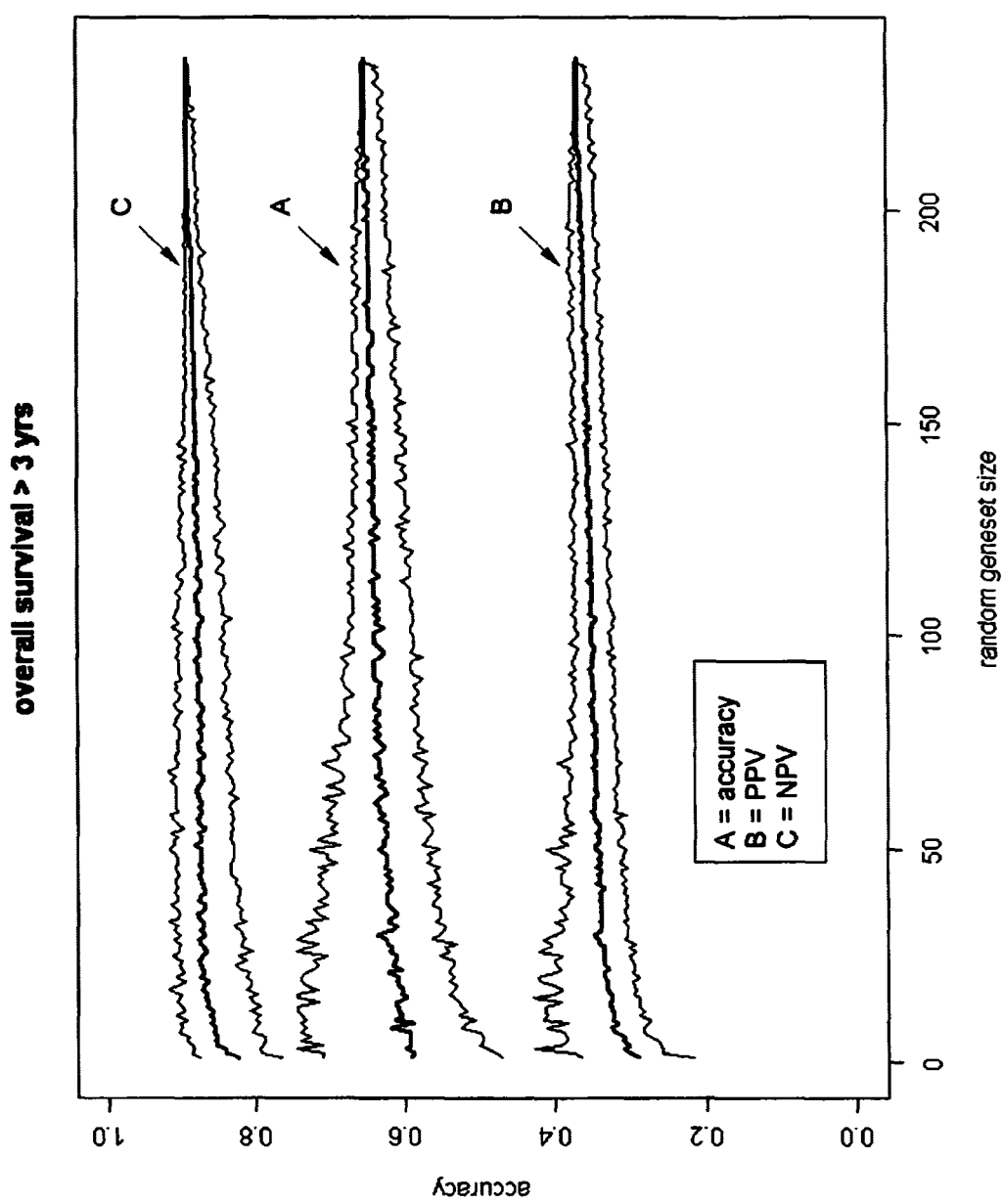

It is particularly preferred that said set of genes comprises at least four of the genes listed in Table 3 resulting in an average accuracy of 0.598837; more preferred at least nine of the genes listed in Table 3 resulting in an average accuracy of 0.6046512; more preferred at least forty-nine of the genes listed in Table 3 resulting in an average accuracy of 0.6337209; more preferred at least ninety of the genes listed in Table 3 resulting in an average accuracy of 0.6453488; more preferred all of the genes listed in Table 3 resulting in an average accuracy of 0.651163; as indicated in FIG. 9.

The genes listed in Table 3 can be rank ordered. Ranking can be based on a correlation with overall survival time, or on a correlation with recurrence free survival time, or on a correlation with differential expression between tumor samples from low-risk and high-risk patients, or based on the selection percentages of the genes during the multiple samples approach (Michiel et al., Lancet 365: 488-92 (2005)), as is known to a skilled person. Ranking of the genes listed in Table 3 was performed according to their selection percentages during the multiple samples approach, in which the top-ranked genes represent the genes that were most often selected for development of the prognostic signature.

Figure 8:
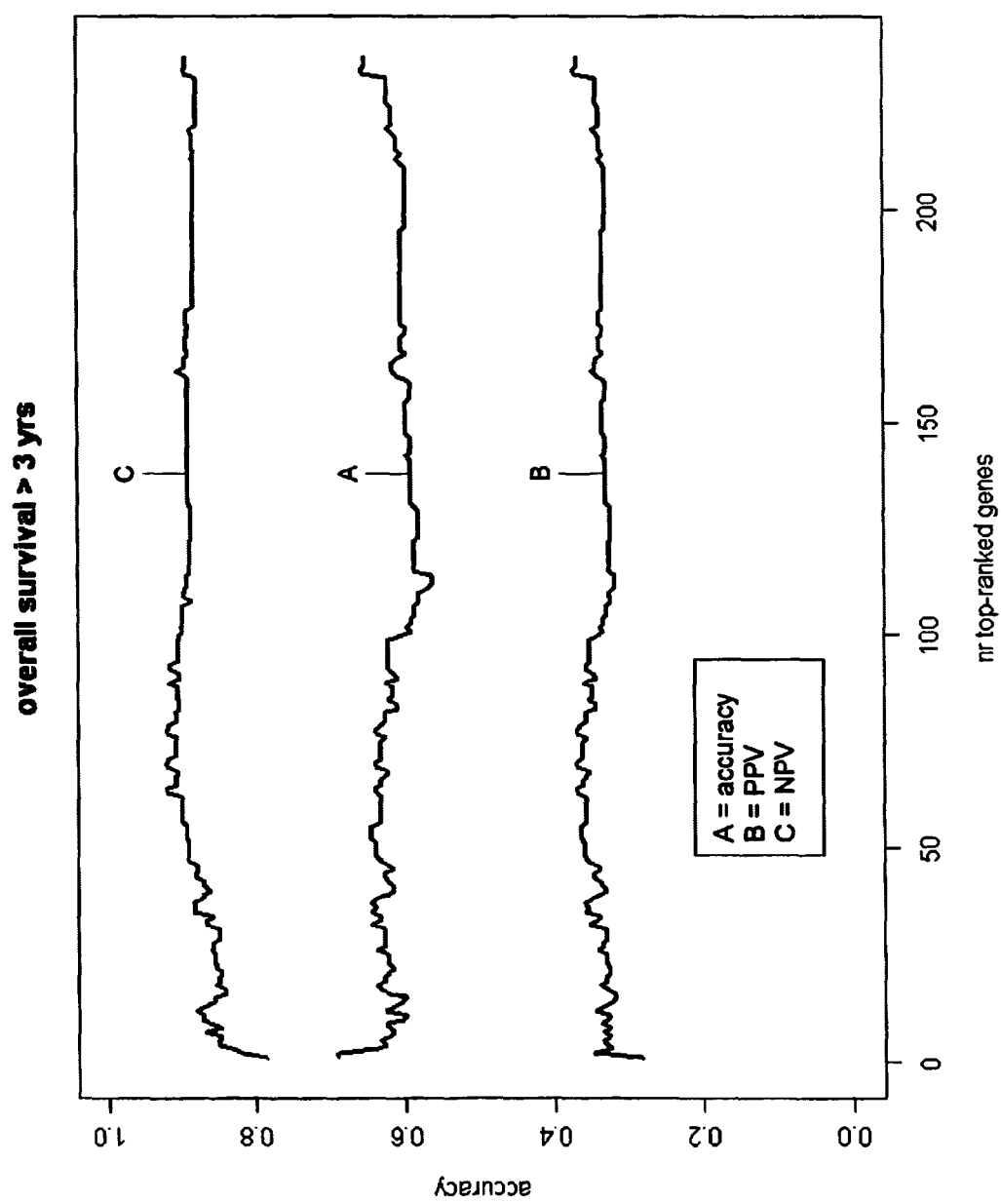

A preferred set of genes for use in a method of the invention comprises the first two rank-ordered genes listed in Table 3 resulting in negative predictive value of 0.7857143; more preferred the first eight rank-ordered genes listed in Table 3 resulting in negative predictive value of 0.8681319; more preferred the first thirty-six rank-ordered genes listed in Table 3 resulting in negative predictive value of 0.8829787; more preferred the first fifty-seven rank-ordered genes listed in Table 3 resulting in negative predictive value of 0.8977273; and most preferred the first seventy-two rank-ordered genes listed in Table 3 resulting in negative predictive value of 0.9166667, as indicated in FIG. 8.

It is furthermore preferred that a set of genes for use in a method of the invention comprises at least two of the genes listed in Table 3, whereby one of said at least two genes is Ref Seq number XM_04626. In a more preferred embodiment, a set of genes according to the invention comprises Ref Seq number XM_04626 and Ref Seq number NM_052966; more preferred Ref Seq number XM_04626, Ref Seq number NM_052966, and Ref Seq number NM_002664; more preferred Ref Seq number XM_04626, Ref Seq number NM_052966, Ref Seq number NM_002664, and Ref Seq number NM_004310; more preferred Ref Seq number XM_04626, Ref Seq number NM_052966, Ref Seq number NM_002664, Ref Seq number NM_004310, and Ref Seq number NM_004288; more preferred Ref Seq number NM_04626, Ref Seq number NM_052966, Ref Seq number NM_002664, Ref Seq number NM_004310, Ref Seq number NM_004288 and Ref Seq number NM_003195; more preferred Ref Seq number NM_04626, Ref Seq number NM_052966, Ref Seq number NM_002664, Ref Seq number NM_004310, Ref Seq number NM_004288, Ref Seq number NM_003195, and Ref Seq number NM_024560; more preferred Ref Seq number NM_04626, Ref Seq number NM_052966, Ref Seq number NM_002664, Ref Seq number NM_004310, Ref Seq number NM_004288, Ref Seq number NM_003195, Ref Seq number NM_024560 and Ref Seq number NM_014358; more preferred Ref Seq number NM_04626, Ref Seq number NM_052966, Ref Seq number NM_002664, Ref Seq number NM_004310, Ref Seq number NM_004288, Ref Seq number NM_003195, Ref Seq number NM_024560, Ref Seq number NM_014358, and Ref Seq number NM_201286; more preferred Ref Seq number NM_04626, Ref Seq number NM_052966, Ref Seq number NM_002664, Ref Seq number NM_004310, Ref Seq number NM_004288, Ref Seq number NM_003195, Ref Seq number NM_024560, Ref Seq number NM_014358, Ref Seq number NM_201286, and Ref Seq number NM_172006.

The genes listed in Table 3 can be identified by the gene name or by the unique identifier according to the NCBI Reference Sequences (Refseq), as provided in Table 3. Preferably, said genes can be identified by a part of the sequence of said gene which is provided in Table 3.

The RNA level of at least two of the genes listed in Table 3 can be determined by any method known in the art, including but not limited to Northern blotting, ribonuclease protection assay, multiplex technologies such as Locked Nucleic Acid-modified capture probes and multi-analyte profiling beads, quantitative polymerase chain reaction (qPCR), and microarray-mediated analyses. If required, an RNA sample can be reverse-transcribed by known methods, such as by random primed or by oligo (dT) primed reverse transcriptase reaction, into copy-DNA prior to determination of the expression level. qPCR comprises end point polymerase reaction and real-time polymerase reaction. Alternatives to PCR, such as strand-displacement amplification, branched DNA, loop-mediated isothermal amplification and nucleic-acid sequence based amplification are specifically included in this embodiment.

In a preferred method according to the invention, RNA levels are determined by means of an array or microarray.

(Micro)array-mediated analyses to determine RNA levels of at least two of the genes listed in Table 3 in a RNA sample comprises the use of a probe on a solid surface to determine the levels of a specific RNA that is present in a RNA from a tissue sample. Said probe can be a desoxyribonucleic acid (DNA) molecule such as a genomic DNA or fragment thereof, a ribonucleic acid molecule, a cDNA molecule or fragment thereof, a PCR product, a synthetic oligonucleotide, or any combination thereof. Said probe can be a derivative or variant of a nucleic acid molecule, such as, for example, a peptide nucleic acid molecule.

Said probe is specific for a gene listed in Table 3. A probe can be specific when it comprises a continuous stretch of nucleotides that are completely complementary to a nucleotide sequence of a RNA product of said gene, or a cDNA product thereof. A probe can also be specific when it comprises a continuous stretch of nucleotides that are partially complementary to a nucleotide sequence of a RNA product of said gene, or a cDNA product thereof. Partially means that a maximum of 5% from the nucleotides in a continuous stretch of at least 20 nucleotides differs from the corresponding nucleotide sequence of a RNA product of said gene. The term complementary is known in the art and refers to a sequence that is related by base-pairing rules to the sequence that is to be detected. It is preferred that the sequence of the probe is carefully designed to minimize nonspecific hybridization to said probe. It is preferred that the probe is or mimics a single stranded nucleic acid molecule. The length of said complementary continuous stretch of nucleotides can vary between 15 bases and several kilo bases, and is preferably between 20 bases and 1 kilobase, more preferred between 40 and 100 bases, and most preferred 60 nucleotides.

To determine the RNA level of at least two of the genes listed in Table 3, the RNA sample is preferably labeled, either directly or indirectly, and contacted with probes on the array under conditions that favor duplex formation between a probe and a complementary molecule in the labeled RNA sample. The amount of label that remains associated with a probe after washing of the microarray can be determined and is used as a measure for the level of RNA of a nucleic acid molecule that is complementary to said probe.

Systemic bias can be introduced during the handling of the sample in a microarray experiment. To reduce systemic bias, the determined RNA levels are preferably corrected for background non-specific hybridization and normalized using, for example, Feature Extraction software (Agilent Technologies). Other methods that are or will be known to a person of ordinary skill in the art, such as a dye swap experiment (Martin-Magniette et al., Bioinformatics 21:1995-2000 (2005)) which can be performed to normalize differences introduced by dye bias, can, also be applied.

In a preferred method according to the invention, the determination of the RNA levels comprises normalizing the determined levels of RNA of said set of genes in said sample.

Normalization corrects for variation due to inter-array differences in overall performance, which can be due to for example inconsistencies in array fabrication, staining and scanning, and variation between labeled RNA samples, which can be due for example to variations in purity. Conventional methods for normalization of array data include global analysis, which is based on the assumption that the majority of genetic markers on an array are not differentially expressed between samples [Yang et al., Nucl Acids Res 30: 15 (2002)]. Alternatively, the array may comprise specific probes that are used for normalization. These probes preferably detect RNA products from housekeeping genes such as glyceraldehyde-3-phosphate dehydrogenase and 18S rRNA levels, of which the RNA level is thought to be constant in a given cell and independent from the developmental stage or prognosis of said cell. Said specific probes preferably are specific for genes of which the RNA level varies over a wide range of levels.

In a preferred embodiment, a method of the invention further comprises comparing an RNA level at least two of the genes listed in Table 3 to an RNA level of said genes in a reference sample.

The reference sample can be an RNA sample isolated from a lung tissue from a healthy individual, or from so called normal adjacent tissue from an individual suffering from NSCLC, or an RNA sample from a relevant cell line or mixture of cell lines. Said reference sample can also be an RNA sample from a cancerous growth of an individual suffering from NSCLC. Said individual suffering from NSCLC can have an increased risk of cancer recurrence, or a low risk of cancer recurrence.

It is preferred that said reference sample is an RNA sample from an individual suffering from non-small cell lung cancer and having a low risk of cancer recurrence. In a more preferred embodiment, said reference sample is a pooled RNA sample from multiple tissue samples comprising NSCLC cells from individuals suffering from non-small cell lung cancer and having a low risk of cancer recurrence. It is preferred that said multiple tissue sample comprise more than 10 tissue samples, more preferred more than 20 tissue samples, more preferred more than 30 tissue samples, more preferred more than 40 tissue samples, most preferred more than 50 tissue samples.

Comparison of a sample with a reference sample can be performed in various ways. Preferably a coefficient is determined that is a measure of the similarity of dissimilarity of a sample with said reference sample. A number of different coefficients can be used for determining a correlation between the RNA expression level in an RNA sample from an individual and a reference sample. Preferred methods are parametric methods which assume a normal distribution of the data. One of these methods is the Pearson product-moment correlation coefficient, which is obtained by dividing the covariance of the two variables by the product of their standard deviations. Preferred methods comprise cosine-angle, un-centered correlation and, more preferred, cosine correlation (Fan et al., Conf Proc IEEE Eng Med Biol Soc. 5:4810-3 (2005)).

Preferably, said correlation with a reference sample is used to produce an overall similarity score for the set of genes that are used. A similarity score is a measure of the average correlation of RNA levels of a set of genes in an RNA sample from an individual and a reference sample. Said similarity score is a numerical value between +1, indicative of a high correlation between the RNA expression level of the set of genes in the RNA sample of the individual and the reference sample, and −1, which is indicative of an inverse correlation and therefore indicative of having an increased risk of cancer recurrence (van 't Veer et al., Nature 415: 484-5 (2002)).

In particularly preferred embodiment, an arbitrary threshold is determined for said similarity score. RNA samples that score below said threshold are indicative of an increased risk of cancer recurrence, while samples that score above said threshold are indicative of a low risk of cancer recurrence.

A similarity score and or a resultant of said score, which is a measurement of increased risk or low risk of cancer recurrence, is preferably displayed or outputted to a user interface device, a computer readable storage medium, or a local or remote computer system.

In another aspect, the invention provides a set of probes for typing a sample of an individual suffering from NSCLC, or suspected of suffering therefrom, wherein said set of probes comprises probes that are specific for at least two of the genes listed in Table 3.

The RNA level of a set of genes comprising at least two of the genes listed in Table 3 was found to be discriminative between an RNA sample from an individual suffering from NSCLC and having an increased risk for recurrence of said cancer, and an RNA sample from an individual suffering from NSCLC and having a reduced risk for recurrence of said cancer.

It is preferred that said set probes comprises probes that are specific for at least three of the genes listed in Table 3, more preferred four of the genes listed in Table 3, more preferred five of the genes listed in Table 3, more preferred six of the genes listed in Table 3, more preferred seven of the genes listed in Table 3, more preferred eight of the genes listed in Table 3, more preferred nine of the genes listed in Table 3, more preferred ten of the genes listed in Table 3, more preferred fifteen of the genes listed in Table 3, more preferred twenty of the genes listed in Table 3, more preferred thirty of the genes listed in Table 3, more preferred forty of the genes listed in Table 3, more preferred sixty of the genes listed in Table 3, more preferred seventy of the genes listed in Table 3, more preferred seventy-two of the genes listed in Table 3, more preferred eighty of the genes listed in Table 3, more preferred ninety of the genes listed in Table 3, more preferred hundred of the genes listed in Table 3, more preferred two-hundred of the genes listed in Table 3, more preferred all of the genes listed in Table 3.

Preferably said set of probes comprises probes specific for not more than 227 different genes, more preferred not more than 150 different genes, more preferred not more than 72 different genes of the genes listed in Table 3.

In yet another aspect, the invention provides the use of a set of probes that are specific for a set of genes of the invention for determining a risk for an individual suffering of NSCLC or suspected of suffering from said cancer, for recurrence of said cancer.

According to this aspect, the invention provides the use of set of probes that are specific for a set of genes of the invention for discriminating between NSCLC cells with a low versus a high metastasizing potential by determining a nucleic acid level of expression of said set of marker genes in an RNA sample from a patient suffering from NSCLC or suspected of suffering from said cancer.

The invention furthermore provides an array comprising between 2 and 12.000 probes of which two or more probes are specific for at least two of the genes listed in Table 3. The invention furthermore provides the use of an array according to the invention for typing of NSCLC cells.

The invention also provides a set of primers for typing a sample of an individual suffering from non-small cell lung cancer or suspected of suffering there from, whereby said set of primers comprises primers specific for at least two of the genes listed in Table 3.

Said set of primer can be used for determining an RNA level for said at least two of the genes listed in Table 3 in a sample. Known methods for determining an RNA level comprise amplification methods, including but not limited to polymerase chain reaction such as multiplex PCR and multiplex ligation-dependent probe amplification, and nucleic acid sequence-based amplification.

Preferably said set of primers comprises primers specific for less than 227 different genes, more preferred not more than 150 different genes, more preferred not more than 72 different genes of the genes listed in Table 3.

According to this aspect, the invention further provides the use of a set of primers according to the invention for determining a risk for an individual suffering of NSCLC for recurrence of said cancer. The invention also provides the use of a set of primers according to the invention for discriminating between NSCLC cells with a low versus a high metastasizing potential.

In a further aspect, the invention provides a method of classifying a sample from an individual suffering from NSCLC, or suspected of suffering from NSCLC, comprising classifying a sample as derived from an individual having a poor prognosis or a good prognosis by a method comprising providing a sample from said individual; determining a level of RNA for a set of genes comprising at least two of the genes listed in Table 3 in said sample; determining a similarity value for the level of RNA in said sample and a level of RNA for said set of genes in a patient having no recurrent disease within three years of initial diagnosis; and classifying said individual as having a poor prognosis if said similarity value is below a first similarity threshold value, and classifying said individual as having a good prognosis if said similarity value exceeds said first similarity threshold value.

Said reference sample is preferably a sample from normal lung tissue, from normal adjacent tissue, from a cell line or mixture of cell lines, or a relevant sample from an individual suffering from NSCLC. Preferably, a reference sample is from an individual suffering from non-small cell lung cancer and having a low risk of cancer recurrence. In a more preferred embodiment, said reference sample is a pooled RNA sample from multiple tissue samples comprising NSCLC cells from individuals suffering from non-small cell lung cancer and having a low risk of cancer recurrence.

A reference sample can also comprise a sample from an individual suffering from non-small cell lung cancer and having an increased risk of cancer recurrence. In that instance, the invention similarly provides a method of classifying an individual suffering from NSCLC, or suspected of suffering from NSCLC, comprising classifying a sample as derived from an individual having a poor prognosis or a good prognosis by a method comprising providing a sample from said individual; determining a level of RNA for a set of genes comprising at least two of the genes listed in Table 3 in said sample; determining a similarity value for the level of RNA in said sample and a level of RNA for said set of genes in a patient having recurrent disease within three years of initial diagnosis; and classifying said individual as having a good prognosis if said similarity value is below a first similarity threshold value, and classifying said individual as having a poor prognosis if said similarity value exceeds said first similarity threshold value.

LEGEND OF THE FIGURES

FIG. 1: Kaplan-Meier plot survival estimates of overall survival of patients with a good (low-risk) profile and of patients with a poor (high-risk) profile, as identified using a leave-one-out training approach.

Figure 2:
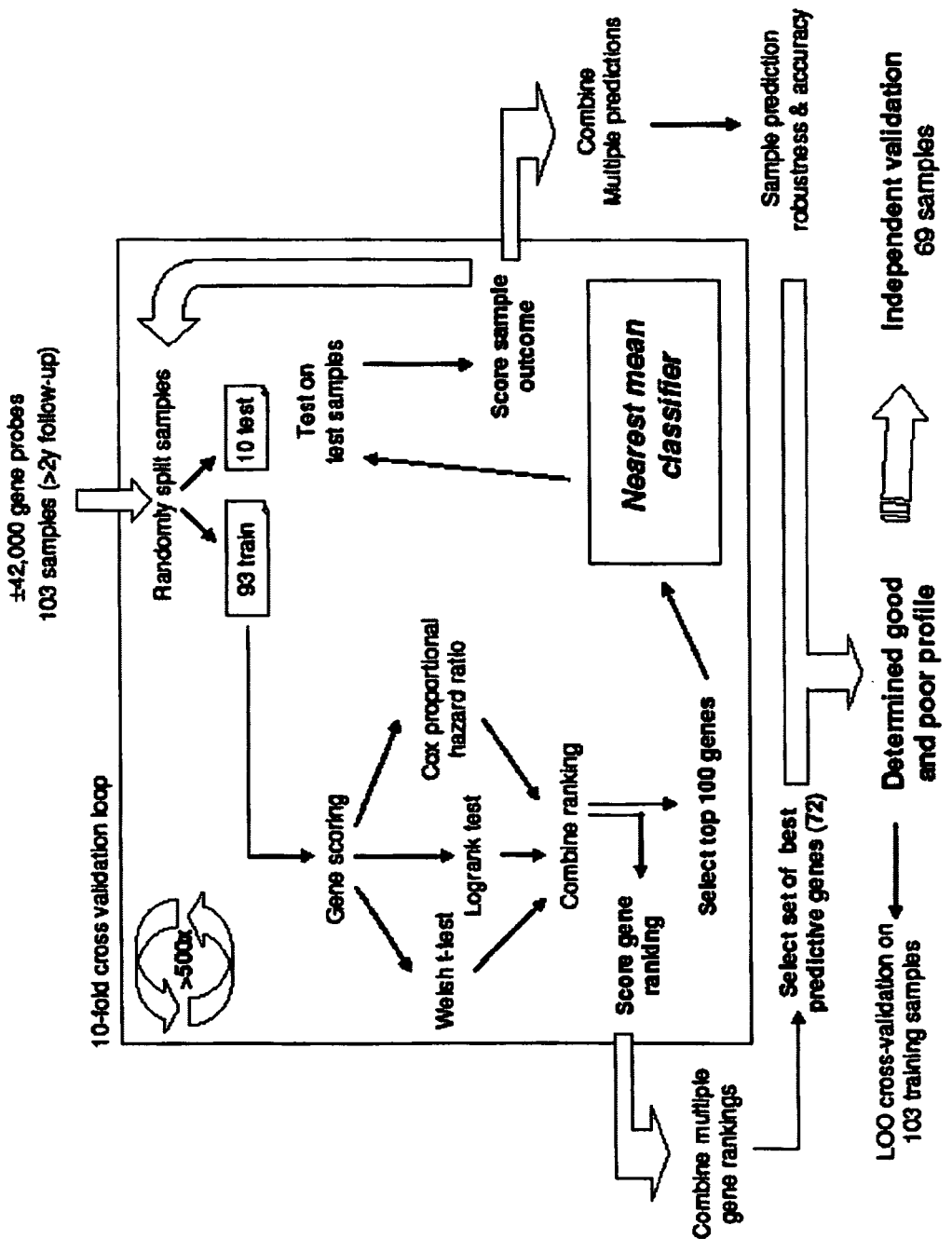

FIG. 2: Schematic overview of the multiple samples procedure that was used for development of a robust nearest mean classifier. A 10-fold cross validation loop was used to identify genes which expression ratios correlate with overall and recurrence free survival time.

Figure 3:
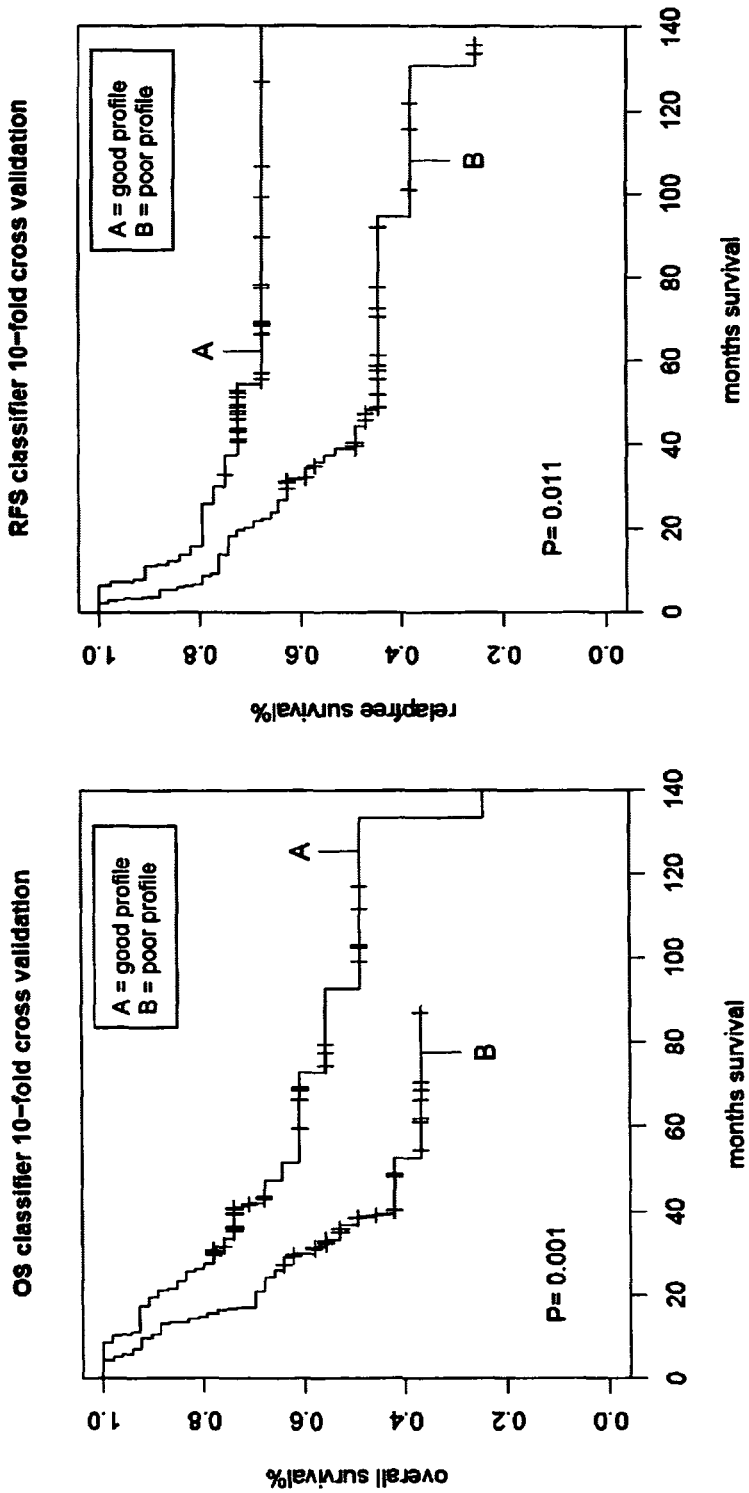

FIG. 3: Kaplan-Meier plot survival estimates of overall survival (OS) and relapse-free survival (RFS) based on the multiple sampling outcomes of the test samples.

Figure 4:
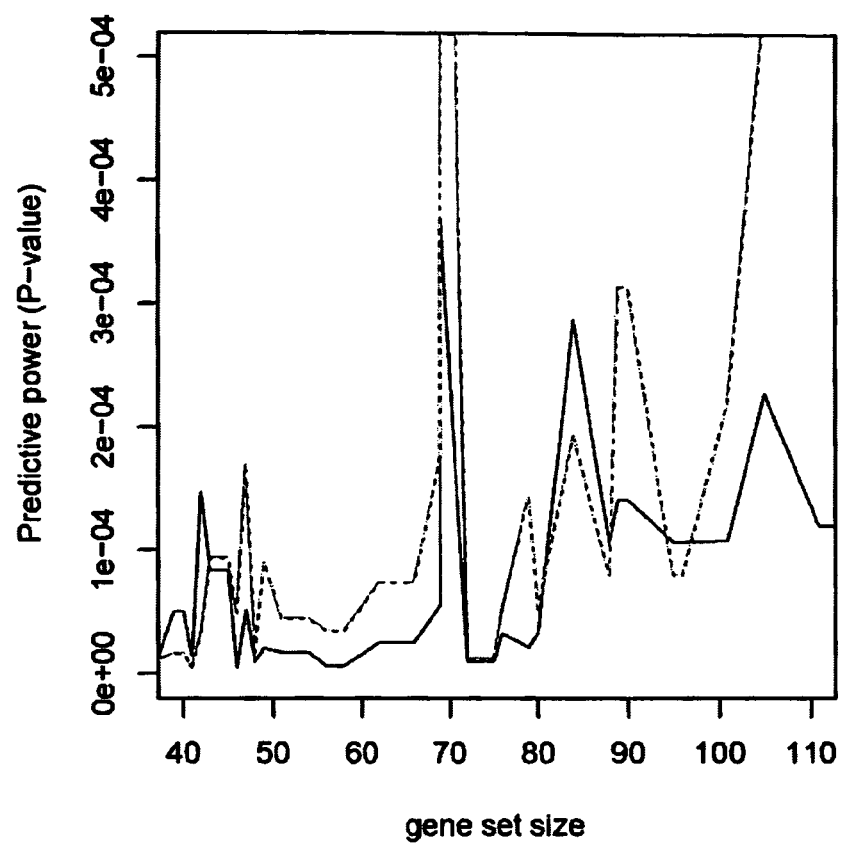

FIG. 4: Prognostic power (P-values) of the nearest mean classifier using different gene set sizes. The highest power (lowest p-values) for both overall survival (black line) and relapse free survival (blue line) is reached upon using a gene set size of 72 genes.

Figure 5:
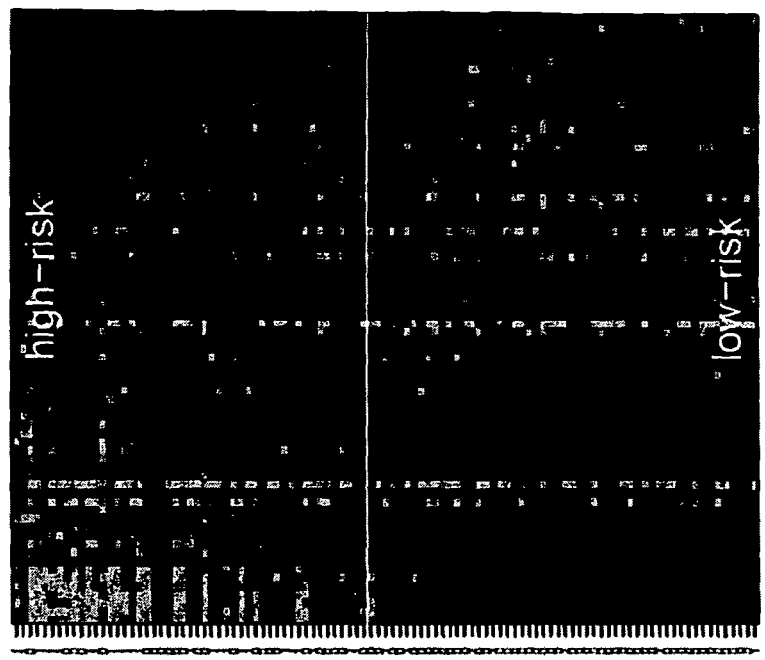
Figure 5:
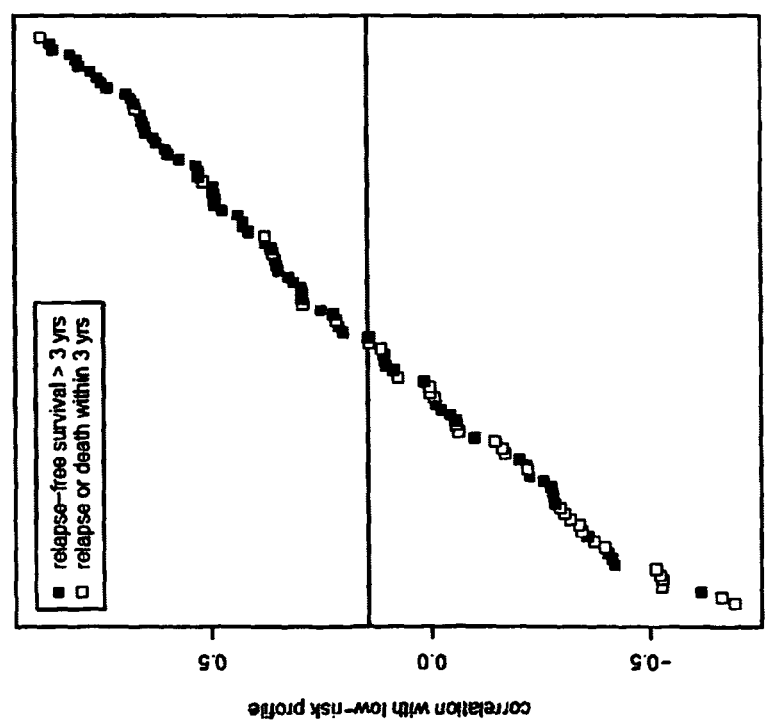

FIG. 5: Left panel; Classifier prognostic low-risk correlation outcome (leave-one-out cross validation) of 103 training samples. Correlations above −0.145 indicate samples with a low-risk profile and correlation below −0.145 indicate samples with a high-risk profile. The samples are colored according to their true survival status. Right panel, visualization of the 72-gene prognostic signature. Each row represents one sample and each column represents one gene. Samples are labeled according to their true survival status (1: relapse or death with 3 years; 0: relapse-free survival for at least 3 years). Red indicates up regulation of a gene, green indicates down regulation of a gene.

Figure 6:
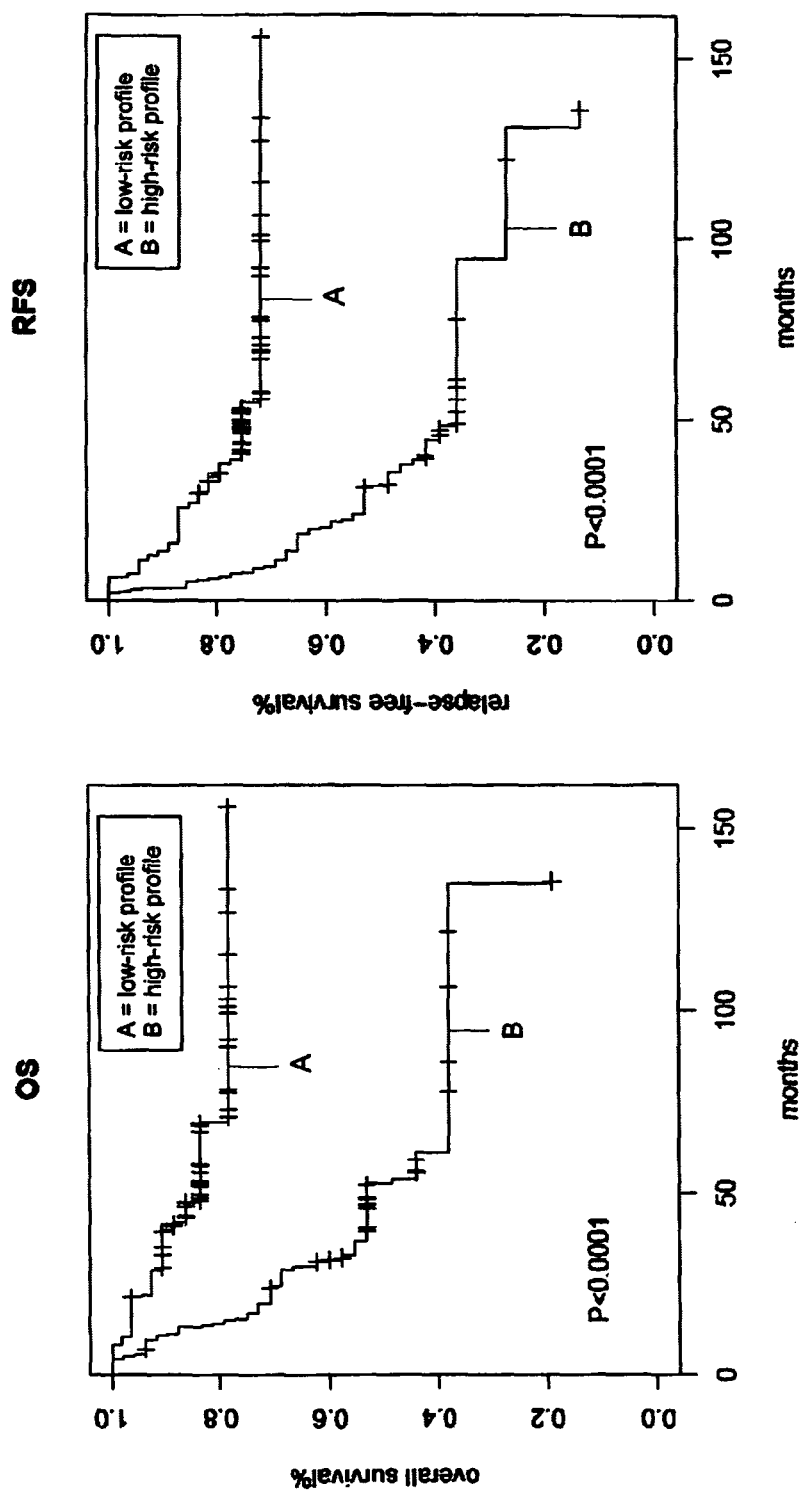

FIG. 6: Kaplan-Meier plot survival estimates of overall survival (OS) and relapse-free survival (RFS) of the 103 training samples with a low-risk 72-gene profile and of patients with a high-risk 72-gene profile.

Figure 7A:
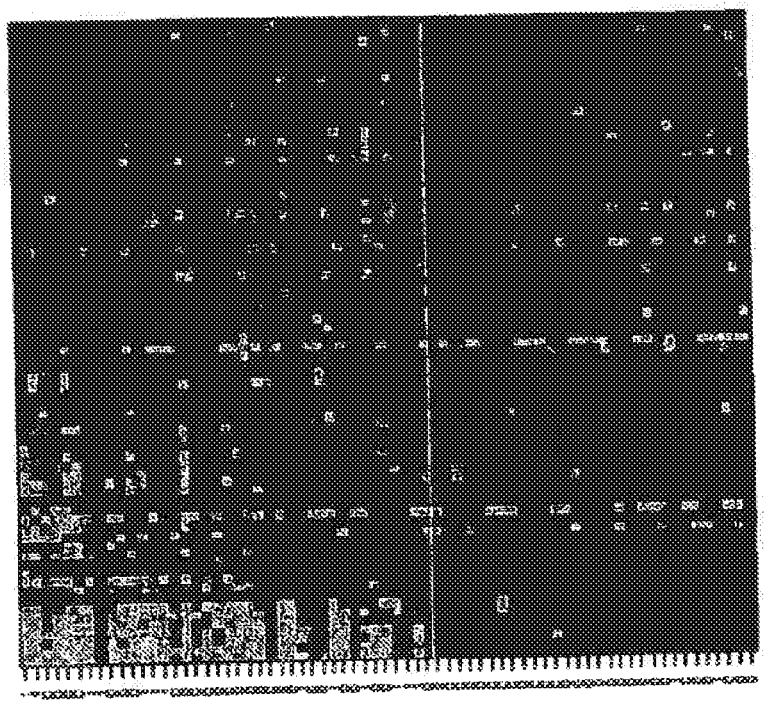
Figure 7B:
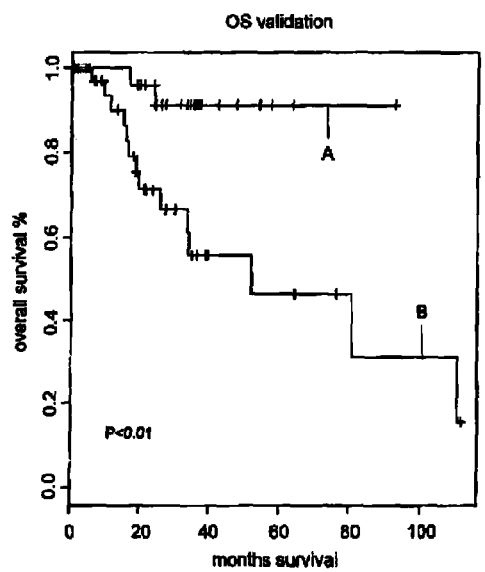
Figure 7C:
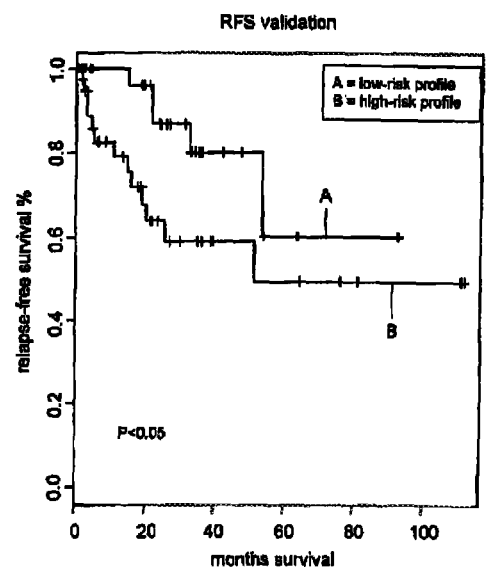

FIG. 7: Validation of the 72-gene signature on 69 independent samples. FIG. 7a; as right panel in FIG. 5 for the 69 independent validation samples. FIGS. 7b and 7c; as FIG. 6 for the independent validation samples.

FIG. 8: Performance of ranked subset from the 237 genes with prognostic value for overall survival for 3 years after diagnosis. Negative predictive value (NPV), positive predictive value (PPV) and total accuracy are calculated for increasing ranked subset of the 237 genes (top 2, top 3, top 4, . . . top 230, all 231 genes).

FIG. 9: Prognostic performance of random subsets of different size from the total set of 237 genes. For all different subset sizes (2, 3, 4, . . . , 236, 237) the mean value and 95% confidence interval were calculated for the negative predictive value (NPV), positive predictive value (PPV) and total accuracy.

Figure 10:
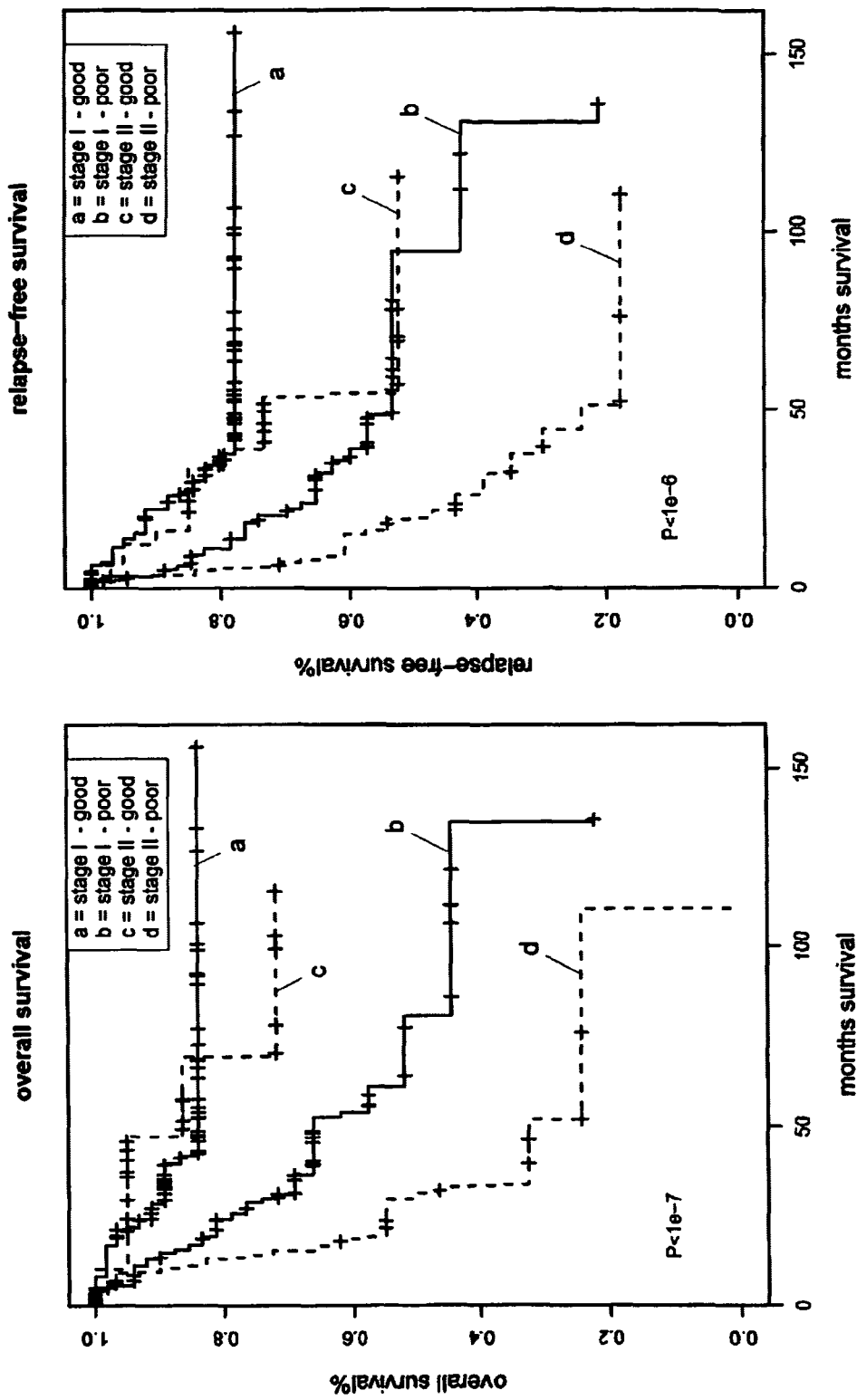

FIG. 10: Kaplan-Meier plot survival estimates of overall survival (OS) and relapse-free survival (RFS) of 172 non small cell lung cancer patients based on a classification by the 72-gene signature (good profile or poor profile) and by tumor staging (stage I or stage II).

Example 1

Non small cell lung cancer samples were analyzed on Agilent 44K array against a lung reference pool that consisted of a pool of RNA from 65 NSCLC samples. A total of 103 samples were used for training the predictive signature and 69 as an independent validation set. The samples originated from 5 different European institutes and included mainly squamous cell carcinomas and adenocarcinomas. An overview of the sample and patient characteristics is given in Table 1. All samples were taken with informed consent of the patients according to the ethical standards of the Helsinki Declaration. RNA isolation and cRNA labeling followed standard protocols (Glas et al., BMC Genomics 2006; 7: 278). Hybridization was performed on Agilent platform (Agilent 44K arrays) according to standard procedures described by the manufacturer and as described elsewhere (Glas et al., BMC Genomics 2006; 7: 278). R and Bioconductor packages, available from the Bioconductor project, were used for statistical analyses of the data.

A leave-one-out cross validation procedure for development of a nearest-mean classifier did not result in a signature that could be validated using this type of cross validation procedure (FIG. 1). In accordance with the hierarchical clustering, this finding indicated that the gene expression data of the analyzed samples did not harbor a very consistent and striking gene expression pattern that correlated with overall survival. Apparently, due to the large heterogeneity in gene expression between tumor samples from good-outcome and from poor-outcome patients, exclusion of a single sample for training of the signature is not sufficient to identify an unbiased gene signature that also works on independent additional test samples. Instead it required a more robust multiple sampling procedure to identify an unbiased set of survival predictive signature genes.

A 10-fold cross validation procedure was used for a more robust and less biased identification of predictive genes (FIG. 2). Ten percent of the training samples were randomly removed from the training set and for all genes a cox-proportion hazard ratio was calculated together with a Log-rank survival score and a p-value for discriminatory power between those patients with and without a survival (or relapse) event (Welsh t-test). The three survival statistics were combined into a single score which was used to rank the genes according to their association with overall (or relapse-free) survival. Next, the top-ranked genes were used for prediction of the 10 left-out samples using a nearest-mean classifier. By repeating this 10-fold cross validation procedure at least 500 times, we determined the unbiased performance of the classifiers, which were all based on different training sets. The multiple classifiers as obtained from, the different training sets were trained towards prediction of overall survival (OS) (P=0.001, FIG. 3A) as well as the classifiers for prediction of relapse-free survival (RFS) (P=0.011, FIG. 3B) showed a significant performance for accurate prediction of the test samples and indicated that the 10-fold cross validation procedure was not biased toward the used training samples. More importantly, this multiple sampling approach allowed us to identify those predictive genes that were most stably selected for building the signatures. These stably selected genes are most favorable for an optimal unbiased predictive signature.

To develop a classifier with optimal performance for prediction of overall survival (OS) as well as relapse-free survival (RFS), the gene selection scores generated by the multiple samples procedure for OS and RFS were ranked and genes with a high ranking in both survival analyses were selected. Starting with a minimal list of the 40 highest ranked genes, the set of predictive genes was gradually expanded to determine the optimal gene set size with the highest predictive accuracy (both for OS and RFS) on all training samples (FIG. 4). The strongest predictive power was reached with a set of 72 predictive genes, corresponding to the highest rank-ordered seventy-two genes listed in Table 3. Investigation of the 72-gene signature performance by leave-one-out cross validation on the training samples (FIG. 5A) indicated that an optimal prediction was achieved based on the sample correlations with the good-outcome profile (FIG. 5B, threshold; 0.145). An average low-risk profile was calculated for the 72-gene signature (Table 2, second column) which served as the low-risk profile for further validation of the classifier. High and low risk training samples showed a clear difference in gene expression of the 72 signature genes (FIG. 5C). Survival analysis of the training samples confirmed that the patients of whom the lung tumor samples show a low-risk profile have a significant better survival rate for overall survival (OS) and for relapse-free survival (RFS) time than patients with high-risk tumor profile (P<0.0001) (FIG. 6).

The predictive signature was validated on an independent set of 69 validation samples (Table 1). The gene expression profiles of the validation samples indicated that the predictive signature is also present in independent samples (FIG. 7A). Survival analysis of the independent validation samples confirmed the discriminatory power of the 72-gene signature for identification of low- and high-risk NSCLC patients (FIG. 7B-C). The somewhat lower significance on the validation set was (partially) caused by the relative high number of censoring events within 3 years after diagnosis (lost for follow-up; other caused of death) (see also Table 1).

The sensitivity, specificity, negative predictive value (NPV), positive predictive value and overall accuracy of the classifier (Table 2) confirm the finding that the classifier is able to discriminate between patients with a low and high risk for disease progression, especially towards prediction of low-risk patients (NPV of 9.3 percent on the validation set). The median overall survival time of low-risk and high-risk patients is 47 and 31 months, respectively (P<1e-4, Wilcoxon rank-sum test) and the median relapse-free survival time for both patients groups is 47 versus 24 months, respectively (P<1e-5) (Table 4).

Example 2

To determine the minimal number of signature genes that are needed for an accurate prognostic signature, the set of 237 genes was ranked according to the prognostic power of the individual genes and the set of 237 genes was sequentially reduced till a gene set comprising only the two top ranked genes. For each different gene set size (i.e. comprising from 2 genes up to 237 genes) the negative predictive value (NPV), positive predictive value (PPV) and total accuracy were determined for prognosis off overall survival for at least 3 years. FIG. 8 shows that the predictive power of the signature decreases only marginally in case of a lower number of ranked signature genes; a prognostic signature that comprises of only the top 2 genes has a NPV of 80 percent and a total accuracy of 70 percent. Thus, a small number of top-ranked genes already showed a high accuracy in prediction of low-risk patients (overall survival NPV of 83%).

We further analyzed the performance of a random subset of 2 or more genes selected from the set of 237 genes. Random subsets were selected with different sizes ranging from 2 genes up to all 237 genes. In total, hundred random, computer generated subsets were selected if possible for each different size and for each different subset the NPV, PPV and total accuracy was calculated. Subsequently, the mean performance and the 95 percent confidence interval were calculated for each different subset size. The data shown in FIG. 9 indicate that random subsets of two or more of the 237 signature genes show only a marginal drop of the predictive performance (FIG. 9). This result confirmed that the predictive value of the signature genes does not drop substantially, also in cases when only a small number of genes are used within the prognostic signature. However, the 95% confidence interval of the predictive performances does increase upon use of smaller signatures. This is explained by the fact that random selection of a small number of genes from the total 237 gene set will results in a much larger variation in prognostic outcome than selection of a large subset. Despite this increase in variation, the negative predictive value of the prognostic signature subsets remains between 80-90 percent. These results indicate that, although the highest performance is achieved using the complete set of 72 genes corresponding to the highest rank-ordered seventy-two genes listed in Table 3, the use of only 2 genes already results in an accurate predictive signature.

Example 3

To test whether the classifier predicted survival independently of the other two prognostic factors, tumor type and tumor grade (FIG. 1), a univariate and a multivariate analysis were performed (Table 4). In a univariate analysis, the 72-gene signature was the most significant prognostic factor with a hazard ratio of 4.83 (95% CI: 2.47-9.44, P=4.1e-6) for OS and a hazard ratio if 4.86 (95% CI: 2.40-9.50, P=3.70-6) for RFS. In a multivariate analysis with the other two prognostics factor, the predictive power of the signature remained similar (hazard ratios of 4.70 and 4.61 for overall and relapse-free survival, respectively, Table 4). This specified that the prognostic 72-gene classifier predicted survival outcome independently of the other two factors. The multivariate analysis indicated that tumor grading has an added predictive value on top of the gene classifier (Table 4). A combination of tumor grading (grade I or II) and the signature outcome (low-risk or high-risk) resulted in highly significant overall survival classification (P=6.2e-8, FIG. 10A) and relapse-free survival prediction (P=3.3e-7, FIG. 10B).

Tables

TABLE 1

|  | Training set (103) | | Validation set (69) | |
| --- | --- | --- | --- | --- |
|  |  | (%) |  | (%) |
| Gender |  |  |  |  |
| male | 77 | 75 | 51 | 82 |
| female | 26 | 25 | 18 | 29 |
| Age at diagnosis |  |  |  |  |
| median |  | 62 |  | 67 |
| range |  | 41-77 |  | 22-79 |
| Hospital |  |  |  |  |
| NKI | 30 | 29 | 6 | 10 |
| Heidelberg | 18 | 17 | 14 | 23 |

TABLE 1-continued

|  | Training set (103) | (%) | Validation set (69) | (%) |
|---|---|---|---|---|
| Bailystok | 12 | 12 | 1 | 2 |
| Gdansk | 32 | 31 | 27 | 44 |
| Vumc | 11 | 11 | 21 | 34 |
| Smoking |  |  |  |  |
| current smoker | 45 | 44 | 30 | 48 |
| former smoker | 44 | 43 | 28 | 45 |
| non-smoker | 3 | 3 | 3 | 5 |
| unknown | 11 | 11 | 8 | 13 |
| Histology |  |  |  |  |
| large cell carcinoma | 8 | 8 | 2 | 3 |
| squamous cell carcinoma | 57 | 55 | 35 | 56 |
| adenocarcinoma | 33 | 32 | 23 | 37 |
| other | 5 | 5 | 9 | 15 |
| Stage |  |  |  |  |
| I | 72 | 70 | 45 | 44 |
| II | 31 | 30 | 24 | 23 |
| Follow-up period (months) |  |  |  |  |
| median |  | 46 |  | 24 |
| range |  | 4-156 |  | 0.5-111 |
| Status |  |  |  |  |
| alive/censored | 59 | 57 | 33 | 53 |
| dead lung cancer | 35 | 34 | 16 | 26 |
| dead other | 9 | 9 | 20 | 32 |
| Relapse-free survival time (months) |  |  |  |  |
| median |  | 43 |  | 22 |
| range |  | 2-156 |  | 0.5-111 |
| Overall survival time (months) |  |  |  |  |
| median |  | 46 |  | 24 |
| range |  | 4.3-156 |  | 0.5-111 |
| Treatment before surgery |  |  |  |  |
| yes | 5 | 5 | 2 | 3 |
| no | 96 | 93 | 58 | 94 |
| unknown | 2 | 2 | 9 | 15 |

TABLE 2

Performance of the 72-gene classifier

| | Sensitivity* | Specificity* | NPV* | PPV* | Accuracy* | P-value[a] |
|---|---|---|---|---|---|---|
| Training | 78 | 66 | 87 | 51 | 70 | 2.4E−05 |
| Validation | 87 | 52 | 93 | 34 | 59 | 0.006 |
| Overall | 81 | 60 | 89 | 43 | 75 | 3.7E−07 |

| | | Months | P-value[b] |
|---|---|---|---|
| Training | | | |
| median OS** | low-risk group | 52 | 3.6E−04 |
| | high-risk group | 33 | |
| median RFS** | low-risk group | 52 | 7.7E−05 |
| | high-risk group | 32 | |
| Validation | | | |
| median OS** | low-risk group | 33 | 0.02 |
| | high-risk group | 23 | |
| median RFS** | low-risk group | 33 | 0.01 |
| | high-risk group | 21 | |
| Overall | | | |
| median OS** | low-risk group | 47 | 2.4E−05 |
| | high-risk group | 31 | |
| median RFS** | low-risk group | 47 | 5.5E−06 |
| | high-risk group | 24 | |

*based on 3-year relapse-free survival
**disregarded patients that died of other other causes than lung cancer
NPV negative predictive value
PPV positive predictive value
OS overall survival time (months)
RFS relapse-free survival time (months)
[a]Log-rank test
[b]Wilcoxon rank sum test

TABLE 3

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 1 | C3orf41 | XM_046264 | chromosome 3 open reading frame 41 | -0.477 | GTCAATGCTGGGAAGACAGGAGAAAAGCTT AATTCTTGACATTTAAATACCAGTTTTCCA |
| 2 | C1orf24 | NM_052966 | chromosome 1 open reading frame 24 | 0.278 | AAAGGTCCAAGGGAATTTAATCTGGAAGAG AACATATGCCAATTTTTAAACTATGACAGC |
| 3 | PLEK | NM_002664 | pleckstrin | 0.329 | TGAGAAAGACAGCACCCATTGAAACAGATA TGTGTGTGAAAGTATATTTTTCAATTCCAG |
| 4 | RHOH | NM_004310 | ras homolog gene family, member H | 0.418 | AAAGCTTGGTGTTTTCTCTGGGTACACCCC AAGCAGCGTCTCCTTTTGGATACAGTTATT |
| 5 | PSCDBP | NM_004288 | pleckstrin homology, Sec7 and coiled-coil domains, binding protein | 0.570 | TTCATCGTGCTGTGGAAGAGGAAGAAAGTC GCTTTTGACGGATTGTGGTGTCCTTTCAAA |
| 6 | TCEA2 | NM_003195 | transcription elongation factor A(SII), 2 | -0.236 | ATCGAGGAATGCATCTTCCGGGACGTTGGA AACACAGACATGAAGTATAAGAACCGTGTA |
| 7 | FLJ21963 | NM_024560 | NA | -0.202 | GCAAGATCCCCCGATCAGCTTTATCTGCCA TTGTCAATGGCAAGCCATACAAGATAACTT |
| 8 | CLEC4E | NM_014358 | C-type lectin domain family 4, member E | 0.317 | GCAAAATTGGAATGATGTAACCTGTTTCCT ACATTATTTTCGGATTTGTGAAATGGTAGG |
| 9 | USP51 | NM_201286 | ubiquitin specific peptidase 51 | -0.458 | AAAGCAGCACCATTTAGCTGTAGACCTTTA TCATGGGTCATATATTGCTTCATGTGTAA |
| 10 | WFDC10B | NM_172006 | WAP four-disulfide core domain 10B | 0.380 | GCGACCCAGCATAGATCTATGCATCCACCA CTGTTCATATTTCCAAAAGTGTGAAACAAA |
| 11 | IGH@ | NA | immunoglobulin heavy locus | 0.219 | CGTGAGGATGCTTGGCACGTACCCCGTGTA CATACTTCCCAGGCACCCAGCATGGAAATA |
| 12 | SLC4A3 | NM_005070 | solute carrier family 4, anion exchanger, member 3 | -0.269 | GATGCTGAACCAAACTTCGATGAGGATGGC CAGGATGAGTACAATGAGCTGCACATGCCA |
| 13 | CD53 | NM_000560 | CD53 molecule | 0.627 | ACCATAGGGCTATGATCTGCAGTAGTTCTG TGGTGAAGAGACTTGTTTCATCTCCGGAAA |
| 14 | LOC401431 | NM_001008745 | NA | -0.466 | AGGTCTGATGCAGTAGCTTTTACTATTGGT GGAAATCGATGTTTTTCCTTGAAAGTCTA |
| 15 | SCFV | XM_941394 | NA | 0.597 | GGGGCTGGAATGGGTGGCAGTTATATCACA TGATGGAAGTAATAAATACTACGCAGACTC |
| 16 | THRAP2 | NM_015335 | thyroid hormone receptor associated protein 2 | -0.171 | AACTTCCTACCACTCACCCTAGCATTACTT ATATGATATGTCTCCATACCCATTACAATC |
| 17 | PRDM13 | NM_021620 | PR domain containing 13 | -0.981 | TAATGACTGCTGTACAGTGGGTATAGTATT TTGGTTTTGGTTCCAGATTGTGCAATCTTT |
| 18 | OBSL1 | XM_051017 | obscurin-like 1 | -0.455 | TTTGCATTCCATTGCATATTTCCAAGTCGG CTTTGCTATAAACACAAATATTCTCCAGAA |
| 19 | C7orf40 | NA | chromosome 7 open reading frame 40 | -0.322 | CTGTGTTAATACACCTAGTGAGGAGTGGAG CTGAATTTGAATGCAAGCCTTGGCACCTTA |
| 20 | TAGAP | NM_054114 | T-cell activation GTPase activating protein | 0.425 | GGCCATACGCCATGCCATAGCTTGTGCTAT CTGTAAATATGAGACTTGTAAAGAACTGCC |
| 21 | MGC11271 | NM_024323 | NA | -0.229 | TTGCAAATTTTAGGGTCCTGAGCCAAGTAT GGATGGTTCAGAATTTGTTTCTTTCCTGGA |
| 22 | IGLV6-57 | | immunoglobulin lambda variable 6-57 | 0.768 | AACTCTGCCTCCCTCACCATCTCTGGACTG AGGACTGAGGACGAGGCTGACTACTACTGT |
| 23 | CD38 | NM_001775 | CD38 molecule | 0.649 | TGAAAATCCTGAGGATTCATCTTGCACAT CTGAGATCTGAGCCAGTCGCTGTGGTTGTT |
| 24 | FKBP9 | NM_007270 | FK506 binding protein 9, 63 kDa | -0.217 | TACTGATGTAGCCCTGAGGTAGTTCATGAA AATGCTGTGCACTCATTCCATGGAATAAAT |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 25 | ADAMTSL2 | NM_014694 | ADAMTS-like 2 | -0.322 | GGCCCAGGGCCCACAGCCAGCGGTGGAGGT GTCTTGCTCCGGGCCCGTAGCCCACGCCCT |
| 26 | CD48 | NM_001778 | CD48 molecule | 0.470 | CATCATGAGGGTGTTGAAAAAGACTGGGAA TGAGCAAGAATGGAAGATCAAGCTGCAAGT |
| 27 | GNPTAB | NM_024312 | N-acetylglucosamine-1-phosphate transferase, alpha and beta subunits | 0.484 | CAGCAATCATTGCAGACTAACTTTATTAGG AGAAGCCTATGCCAGCTGGGAGTGATTGCT |
| 28 | DHRS8 | NM_016245 | dehydrogenase/reductase (SDR family) member 8 | 0.293 | CACCTAGTTTTCTGAAAACTGATTTACCAG GTTTAGGTTGATGTCATCTAATAGTGCCAG |
| 29 | LOC388886 | NM_207644 | NA | -0.302 | CTACTGACTTGTGATGCTCTCAAGCACATG ATAGTGGGCGATGAAGGTCAAGGAGGACTC |
| 30 | CNIH3 | NM_152495 | cornichon homolog 3 (Drosophila) | -0.457 | CTCCCATCTGAAACCTGTGACTCAGGTTTA TGAATGGTGTTTGTGTAGCAACACATTGTG |
| 31 | PSMA6 | NM_002791 | proteasome (prosome, macropain) subunit, alpha type, 6 | 0.016 | TAGCAGAGAGAGACTAAACATTGTCGTTAG TTTACCAGATCCGTGATGCCACTTACCTGT |
| 32 | CCRK | NM_001039803 | cell cycle related kinase | -0.165 | AGGATGAGCGTGAGCCAGAAGCAGCTGTGT ATTTAAGGAAACAAGCGTTCCTGGAATTAA |
| 33 | SHROOM1 | NM_133456 | shroom family member 1 | -0.281 | GTCTCTGCTTTTCCCTTGAGGGATTGGGGA GGACCCAGTCCAGGCCTTTCTAAGATACTC |
| 34 | GPSM1 | NM_015597 | G-protein signalling modulator 1 (AGS3-like, C. elegans) | -0.428 | GTCTGTGCCATGTTGTCAATGGGTCCTTTC CAACCCAAGAGGTACATTTGTTTTTCTGTT |
| 35 | TRO | NM_001039705 | trophinin | -0.397 | CCCCATGTTTACAGATACCGCTAATAAATT GCAGTAGTCCTTCCCATGGAGCCAAAGTAC |
| 36 | GSTT2 | NM_000854 | glutathione S-transferase theta 2 | -0.614 | GTAACATGAAGAACACTCAAAAATTGGCAA ATGTCATCAGTGTTTTAAACAGAATAAAGA |
| 37 | NQO2 | NM_000904 | NAD(P)H dehydrogenase, quinone 2 | 0.099 | TCACAGTGTCTGATTTGTATGCCATGAACT TTGAGCCGAGGGCCACAGACAAAGATATCA |
| 38 | EAF2 | NM_018456 | ELL associated factor 2 | 0.706 | CAGGATTCCTGATATAGATGCCAGTCATAA TAGATTTCGAGACAACAGTGGCCTTCTGAT |
| 39 | MUM1L1 | NM_152423 | melanoma associated antigen (mutated) 1-like 1 | -0.034 | ATGATATAAATGCCAACTGGCAAGTCATTC CAAACTGCTTGAAGGAGTAGATGAACCAGA |
| 40 | MUC4 | NM_004532 | mucin 4, cell surface associated | 0.396 | TGGGGCGAGCACTGTGAGCACCTGAGCATG AAACTCGACGCGTTCTTCGGCATCTTCTTT |
| 41 | C13orf21 | NM_001010897 | chromosome 13 open reading frame 21 | -0.150 | CCTCTGAACGATCACTGGTTTACTTTGTAT GGATACATCTCTCCTCCATTAGAATTGAT |
| 42 | PABPC1 | NM_002568 | poly(A) binding protein, cytoplasmic 1 | 0.040 | CAGAACTTCTTCATATGCTCAAGTCTCCAG AGTCACTCCATTCTAAGGTTGATGAAGCTG |
| 43 | PLA2G7 | NM_005084 | phospholipase A2, group VII (platelet-activating factor acetylhydrolase, plasma) | 0.494 | AAAGCATTTAGGACTTCATAAAGATTTTGA TCAGTGGGACTGCTTGATTGAAGGAGATGA |
| 44 | PARK2 | NM_004562 | Parkinson disease (autosomal recessive, juvenile) 2, parkin | 0.421 | GATGTTTTAATTCCAAACCGGATGAGTGGT GAATGCCAATCCCCACACTGCCCTGGGACT |
| 45 | AOAH | NM_001637 | acyloxyacyl hydrolase (neutrophil) | 0.157 | TTTACAAACTTCAATCTTTTCTACATGGAT TTTGCCTTCCATGAAATCATACAGGAGTGG |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 46 | IGL@ | | immunoglobulin lambda locus | 0.357 | CCCAAGGCATCAAGCCCTCTTCCCGTGCAC TCAATAAACCCTCAATAAATATTCTCATTT |
| 47 | LOC642480 | XM_925983 | NA | 0.097 | GCTGGTAAAATCATTGGTATGTTGTTGGAG ATTGGTAATTTGGAACTCCTTCATATGCTT |
| 48 | TMSB4X | NM_021109 | thymosin, beta 4, X-linked | 0.760 | CCGATATGGCTGAGATTGAGAAATTCGATA AGTCGAAACTGAAGAAGACAGAGATGCAAG |
| 49 | LOC390712 | XM_372630 | NA | 0.855 | CTGTGAAGGGCAGATTGACCATCTCCACAG ACAACTCAAAGAACACGCTGTACCTGCAAA |
| 50 | ACOT8 | NM_005469 | acyl-CoA thioesterase 8 | -0.132 | CTATATTGGCGAGGGCGACATGAAGATGCA CTGCTGCGTGGGCGCCTATATCTCCGACTA |
| 51 | GIMAP7 | NM_153236 | GTPase, IMAP family member 7 | 0.334 | TTTGGGAAGTCAGCCATGAAGCACATGGTC ATCTTGTTCACTCGCAAAGAAGAGTTGGAG |
| 52 | LOC375010 | XM_927556 | NA | -0.365 | ACGTTACAACTGAGTTAGAAGAATATAAGG AAGCCTTTGCAGCAGCATTGAAAGCTAACA |
| 53 | ASAH1 | NM_004315 | N-acylsphingosine amidohydrolase (acid ceramidase) 1 | 0.790 | ATGAACTCGATGCTAAGCAGGGTAGATGGT ATGTGGTACAAACAAATTATGACCGTTGGA |
| 54 | TRIM45 | NM_025188 | tripartite motif-containing 45 | -0.033 | GCAGCACCACTTGAGATTTCCAGAGGACCC AGACCTTTGTTCATTCTAAAGAGACTGATA |
| 55 | C2orf30 | NM_015701 | chromosome 2 open reading frame 30 | 0.567 | ACGATGGTACCCAGACAGTCAGGATGGTGT CACATTTTTATGGAAATGGAGATATTTGTG |
| 56 | EXT2 | NM_000401 | exostoses (multiple) 2 | -0.135 | TCAGGGAACCAAACCCAGAATTCGGTGCAA AAGCCAAACATCTTGGTGGGATTTGATAAA |
| 57 | IFI6 | NM_002038 | interferon, alpha-inducible protein 6 | 0.788 | GCCAAGAACACGCTGTATCTGCAAATGAAC AGTCTGAGAGCCGAGGACACGGCTGTGTAT |
| 58 | KCNE3 | NM_002038 | potassium voltage-gated channel, Isk-related family, member 3 | 0.084 | TCATATACATTAAGTTGAGCCATATGTAAT CACTGTGTTTGTAGGTTAGAAACAGCTGAG |
| 59 | CTSF | NM_003793 | cathepsin F | -0.179 | CCTCTCCATGTCCAGGAAACTTGTAACCAC CCTTTTCTAACAGCAATAAAGAGGTGTCCT |
| 60 | SULT1C1 | NM_001056 | sulfotransferase family, cytosolic, 1C, member 1 | 0.043 | GACGTCATTTGAGAAAATGAAAGAAAATCC CATGACAAATCGTTCTACAGTTTCCAAATC |
| 61 | RASL11b | NM_023940 | RAS-like, family 11, member B | -0.228 | TGCCTAAGGGTGGCTGAAATACTAAAACAC TATCTTACAGCAAGTGAACAGGGGCTACCT |
| 62 | LOC148898 | NM_001008896 | NA | -0.108 | AGGGTCTCCAATTTAGGCTTTCAACATTAT CTCTAAAGAAGGTTATACATTATGTCGGCT |
| 63 | HMGCL | NM_000191 | 3-hydroxymethyl-3-methylglutaryl-Coenzyme A lyase (hydroxymethylglutaricaciduria) | 0.014 | GGACATGGAAATGAGAATAGGTTAAATGGT GCAGGTACCTCATAGCCAGCTCTACACAGA |
| 64 | IGHA1 | | immunoglobulin heavy constant alpha 1 | 0.940 | TGCTGAGTTGGGTTTTCCTTGCTGCTATTT TAAAAGGTGTCCAGTGTGAGGTGCAGCTGG |
| 65 | C1QTNF3 | NM_030945 | C1q and tumor necrosis factor related protein 3 | -0.180 | GTTGAGGGTTTTACATTGCTGTATTCAAAA AATTATTGGTTGCAATGTTGTTCACGCTAC |
| 66 | NKI | | 0 | -0.292 | CATACGGTTTTGTTTGGAGGATGGCTTCTG CTGCTAAAAATACAAAAGTTTGGAAACCGC |
| 67 | IL11RA | NM_004512 | interleukin 11 receptor, alpha | -0.076 | GAGCCCATTTCTGTGAGACCCTGTATTTCA AATTTGCAGCTGAAAGGTGCTTGTACCTCT |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 68 | ADRA2C | NM_000683 | adrenergic, alpha-2C-, receptor | -0.685 | TAGTCGGGGGGTGGCTGCCAGGGGGCAAGG AGAAAGCACCGACAATCTTTGATTACTGAA |
| 69 | IGKC | | immunoglobulin kappa constant | 0.943 | CCATCAGCAGCCTGCAGTCTGAAGATTTTG CAGTTTATTACTGTCAGCAGTATAATAACT |
| 70 | CEACAM5 | NM_004363 | carcinoembryonic antigen-related cell adhesion molecule 5 | -0.252 | AGTTCTCTTTATCGCCAAAATCACGCCAAA TAATAACGGGACCTATGCCTGTTTTGTCTC |
| 71 | PURB | NM_033224 | purine-rich element binding protein B | -0.108 | TCTGTGAATGGAACTGAAGTGAACGTGAAT ATGCTGACTATATCCTGGAAGCATTTTTAT |
| 72 | TPD52 | NM_001025252 | tumor protein D52 | 0.181 | AACATTGCCAAAGGGTGGCAAGACGTGACA GCAACATCTGCTTACAAGAAGACATCTGAA |
| 73 | SLAMF1 | NM_003037 | signaling lymphocytic activation molecule family member 1 | 0.432 | AGGCGCAGAACAGAGCGTTACTTGATAACA GCGTTCCATCTTTGTGTTGTAGCAGATGAA |
| 74 | GCH1 | NM_000161 | GTP cyclohydrolase 1 (dopa-responsive dystonia) | 0.191 | TATTCCATGAAGTTTAGTATTTGGTTGACA TAGTGCTCTTCAAATTCATCCCATTACCCT |
| 75 | KLRB1 | NM_002258 | killer cell lectin-like receptor subfamily B, member 1 | 0.243 | TCAACCCTTGGAATAACAGTTCAGCTGATT GTTCCACCAAAGAATCCAGCCTGCTGCTTA |
| 76 | TRIB2 | NM_021643 | tribbles homolog 2 (Drosophila) | 0.064 | ACGGCTTTTCTATTGCTGTATGATACAGAA CTCTTTTGGCATAAATATTTGTGTTCCCAG |
| 77 | DNAJB9 | NM_012328 | (DnaJ (Hsp40) homolog, subfamily B, member 9 | 0.430 | ATTTCTTTCTTAGTTGTTGGCACTCTTAGG TCTTAGTATGGATTTATGTGTTTGTGTGTG |
| 78 | KHDRBS3 | NM_006558 | KH domain containing, RNA binding, signal transduction associated 3 | -0.436 | ATGATGAAGAGAGTTATGATTCCTATGATA ACAGCTATAGCACCCCAGCCCAAAGTGGTG |
| 79 | TUB | NM_003320 | tubby homolog (mouse) | 0.045 | CTCTAGGTCCATTTTCCTAACCACAAGATA AAGATGTTACATTGTCAAAGCTTGCCGTAG |
| 80 | VNN2 | NM_004665 | vanin 2 | 0.358 | AAAGAGCCTGGGTGTTTGGGTCAGATAAAT GAAGATCAAACTCCAGCTCCAGCCTCATTT |
| 81 | PDLIM4 | NM_003687 | PDZ and LIM domain 4 | -0.240 | TGCTCCCACGCCTGCTTCTTAAGGTCCCTG CTCGGCCGGTGTAAATATGTTTCACCCTGT |
| 82 | ARHGAP15 | NM_018460 | Rho GTPase activating protein 15 | 0.460 | AATGCATTGAAGCTGTTGAGAAAAGAGGTC TAGATGTTGATGGAATATATCGAGTTAGTG |
| 83 | SLC16A12 | NM_213606 | solute carrier family 16, member 12 (monocarboxylic acid transporter 12) | -0.111 | TTATAGTGGGATAATTTTACATCTTAAATA TTTCTTTCTACTACTGTAAGCTCTACTTTG |
| 84 | IGKV1D-13 | | immunoglobulin kappa variable 1D-13 | 1.032 | GAAAGCTCCTAAGCTCCTGATCTATGATGC CTCCAGTTTGGAAAGTGGGGTCCCATCAAG |
| 85 | TBRG4 | NM_004749 | transforming growth factor beta regulator 4 | -0.247 | CCATTCTATGAGTGGCTGGAACTCAAGTCT GAATGGCAGAAAGGCGCCTACCTCAAGGAC |
| 86 | MEGF6 | NM_001409 | multiple EGF-like-domains 6 | -0.446 | AGGCAGGCTTTTTGGTGCTAGGCCCTGGGA CTGGAAGTCGCCCAGCCCGTATTTATGTAA |
| 87 | FCRLM1 | NM_032738 | Fc receptor-like and mucin-like 1 | 0.477 | GACATACCAGTCTTTAGCTGGTGCTATGGT CTGTTCTTTAGTTCTAGTTTGTATCCCCTC |
| 88 | FCGR2B | NM_001002273 | Fc fragment of IgG, low affinity IIb, receptor (CD32) | 0.323 | AATCCCACTAATCCTGATGAGGCTGACAAA GTTGGGGCTGAGAACACAATCACCTATTCA |
| 89 | C1orf24 | NM_052966 | chromosome 1 open reading frame 24 | 0.126 | AAATCGACACTGTGGATTGACTTTCCCGGT CACTATATAAAGCAAATAAACTTAAAACAC |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 90 | ANKRD38 | NM_181712 | ankyrin repeat domain 38 | -0.307 | ATGCCATATGTACAGTCTTGACTATTTCTG AGTCATCTAGTGGCTCCAATTTGCTCCAGG |
| 91 | POU2AF1 | NM_006235 | POU domain, class 2, associating factor 1 | 0.937 | TTTTCTGGGAAATGACTTTTCTGGGAAATG ACAGTTTCTTTGACATATTTTCTTTGCCCA |
| 92 | LOC441212 | NM_001039754 | NA | -0.325 | TCTTTATCAAAGACAACCAAAAGTTACAAC AGTTCAGAGTAGCACATGAGGATTTCATGT |
| 93 | CTSS | NM_004079 | cathepsin S | 0.445 | TCTGTTGGTGTAGATGCGCGTCATCCTTCT TTCTTCCTCTACAGAAGTGGTGTCTACTAT |
| 94 | L3MBTL | NM_015478 | l(3)mbt-like (Drosophila) | 0.004 | TTTGCTTGCCAAACTTAGCTTGCCAGTGAT AGTCAATATTAAAGTGTACTTTTTTCCCC |
| 95 | CDKN1C | NM_000076 | cyclin-dependent kinase inhibitor 1C (p57, Kip2) | -0.239 | GTATTCTGCACGAGAAGGTACACTGGTCCC AAAGTGTAAAGCTTTAAGAGTCATTTATAT |
| 96 | AMPD1 | NM_000036 | adenosine monophosphate deaminase 1 (isoform M) | 0.395 | GGAATTTCTCATGAGGAGAAAGTAAAGTTT CTGGGCGACAATTACCTTGAGGAAGGCCCT |
| 97 | TMED4 | NM_182547 | transmembrane emp24 protein transport domain containing 4 | -0.117 | CAGTTGCTTGATGAGGTGGAACAGATTCAG AAGGAGCAGGATTACCAAAGGTATCGTGAA |
| 98 | LAMB2 | NM_002292 | laminin, beta 2 (laminin S) | -0.227 | CCCACATGCATGTCTGCCTATGCACTGAAG AGCTCTTGGCCCGGCAGGGCCCCCCATAAA |
| 99 | DTX3 | NM_178502 | deltex 3 homolog (Drosophila) | -0.212 | CTGTGAGGAACCTCCTTACCCTGTTCTGGA ATCGCTGCGAGACTGTAGCTTTTAATTTAA |
| 100 | MAP2K6 | NM_002758 | mitogen-activated protein kinase kinase 6 | 0.036 | ACAGCATCAATAGAAAGTCATCTTTGAGAT AATTTAACCCTGCCTCTCAGAGGGTTTTCT |
| 101 | PDGFRB | NM_002609 | platelet-derived growth factor receptor, beta polypeptide | 0.719 | TAGGTGATTATATCTTTGGTACCGTATTGA GAACCCACTCTCCCTCCTTGGACCAACTCT |
| 102 | IGLV2-14 | | immunoglobulin lambda variable 2-14 | 0.968 | CATCACTGGTCTCCAGGCTGAGGACGAGGC TGATTATTACTGCAGCTCATATACAAGCAG |
| 103 | ANKH | NM_054027 | ankylosis, progressive homolog (mouse) | -0.166 | TTATTGGCAGCAGTTTTATAAAGTCCGTCA TTTGCATTTGAATGTAAGGCTCAGTAAATG |
| 104 | XBP1 | NM_005080 | X-box binding protein 1 | 0.644 | CCTTTTTGGCATCCTGGCTTGCCTCCAGTT TTAGGTCCTTTAGTTTGCTTCTGTAAGCAA |
| 105 | LOC283174 | NA | NA | -0.115 | CCCGGGAGTGTTGCAAGTTAAACTGATGAA AAGACGTTTAGTATTTAATTGCTCCTCATG |
| 106 | PGM5 | NM_021965 | phosphoglucomutase 5 | 0.330 | CTAACAGCCAGCCACTGCCCTGGAGGACCA GGGGGAGAGTTTGGAGTGAAGTTTAATGTT |
| 107 | ISYNA1 | NM_016368 | NA | -0.247 | TACCCTATGTTGAACAAGAAAGGACCGGTA CCCGCTGCCACCAATGGCTGCACCGGTGAT |
| 108 | PGRMC1 | NM_006667 | progesterone receptor membrane component 1 | 0.161 | TGCCCGGAAAAATGATTAAAGCATTCAGTG GAAGTATATCTATTTTGTATTTTGCAAAA |
| 109 | IGL@ | | immunoglobulin lambda locus | 0.950 | AAGATAGCAGCCCCGTCAAGCGGGAGTGGA GACCACCACACCCTCCAAACAAAGCAACAA |
| 110 | EFHA2 | NM_181723 | EF-hand domain family, member A2 | -0.457 | GCCACATGCAGGGTTCAGAATAGCTTTCAA CATGTTTGACACTGATGGCAATGAGATGGT |
| 111 | CCM2 | NM_001029835 | cerebral cavernous malformation 2 | -0.009 | TCGGCACCCTCAGAGGGGGATGAGTGGGAC CGCATGATCTCGGACATCAGCAGCGACATT |
| 112 | CTA-246H3.1 | NM_001013618 | NA | 0.923 | AACAAGGCCACACTGGTGTGTCTCATGAAT GACTTCTATCTGGGAATCTTGACGGTGACC |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 113 | SMR3A | NM_012390 | submaxillary gland androgen regulated protein 3 homolog A (mouse) | 0.863 | CACCCTATGGTCCAGGGAGAATTCAATCAC ACTCTCTTCCTCCTCCTTATGGCCCAGGTT |
| 114 | TNFRSF17 | NM_001192 | tumor necrosis factor receptor superfamily, member 17 | 0.902 | GATCTCTTTAGGATGACTGTATTTTTCAGT TGCCGATACAGCTTTTTGTCCTCTAACTGT |
| 115 | PDE6B | NM_000283 | phosphodiesterase 6B, cGMP-specific, rod, beta (congenital stationary night blindness 3, autosomal dominant) | -0.156 | ACTGAGAACATTTGCAGCCACACATGTACA TATGTGTACACAGGTAGACAGATGGACACA |
| 116 | BEX2 | NM_032621 | brain expressed X-linked 2 | -1.281 | ATTTCTTGTGGGTCTCCTATTACCAGCTTC TAAATGAATGTTGTTTTTGACCCAGTTTGT |
| 117 | PTPN21 | NM_007039 | protein tyrosine phosphatase, non-receptor type 21 | 0.006 | TTACTGAAGCTATGCTGGGCAATTCTGGCA ATCATTAAAGTGCATAGATTTCTATCTTAA |
| 118 | LGR6 | NM_001017403 | leucine-rich repeat-containing G protein-coupled receptor 6 | -0.096 | TAAGCTTTGGAAGAGATTACACATGATGTC TTTTTCTTAGAGATTCACAGTGCATGTTAG |
| 119 | BAI2 | NM_001703 | brain-specific angiogenesis inhibitor 2 | -0.008 | ATATATATATCTCTCTATTTTCACACTCCA CTTTGGAACTACCCAGGAGCCAGCGCCCTC |
| 120 | FLJ25006 | NM_144610 | NA | 0.033 | TGTTTGTACTGATACTAGACCATTTAGAGC CCAATTTGTGGTCTACCTTCAGCAAGTGTT |
| 121 | CPNE5 | NM_020939 | copine V | 0.608 | TGGTTCTGTGCCCGTCTCTGAGACAGTCTC TGTGTGGAATTTGCCTTAAACTGAAGTAAA |
| 122 | LOC647115 | XM_930136 | NA | 0.507 | CGAGACCCACCTTCCTCTTCCTTTAGCAGC TGGGAAATTGGGGCGTTTATGGCGCCCCG |
| 123 | KCNN3 | NM_002249 | potassium intermediate/small conductance calcium-activated channel, subfamily N, member 3 | 0.495 | AGTGACCAAGCCAACACTCTGGTGGACCTT TCCAAGATGCAGAATGTCATGTATGACTTA |
| 124 | SLAMF7 | NM_021181 | SLAM family member 7 | 0.617 | GGAGACCTCCCTACCAAGTGATGAAAGTGT TGAAAAACTTAATAACAAATGCTTGTTGGG |
| 125 | TTC22 | NM_017904 | tetratricopeptide repeat domain 22 | 0.571 | AGAACCAACCTCCCATCCTGAATCGCCTGG CAAAAATCTTCTACTTCCTGGGAAAGCAGG |
| 126 | LIPA | NM_000235 | lipase A, lysosomal acid, cholesterol esterase (Wolman disease) | 0.195 | TATAATTACTTTAGCTGCACTAACAGTACA ATGCTTGTTAATGGTTAATATAGGCAGGGC |
| 127 | DHRS8 | NM_016245 | dehydrogenase/reductase (SDR family) member 8 | 0.044 | TGCACAGGGAAGCTAGAGGTGGATACACGT GTTGCAAGTATAAAAGCATCACTGGGATTT |
| 128 | SLC2A14 | NM_153449 | solute carrier family 2 (facilitated glucose transporter), member 14 | -0.263 | CTGACTTAGGGTTAGAATGGCCCAATGATC CTACAACTTTTTGATGCTATTTCATTTGAT |
| 129 | PRG1 | NM_002727 | proteoglycan 1, secretory granule | 0.337 | AGGACTGGGTCAACATGGATTAGAAGAGG ATTTTATGTTATAAAAGAGGATTTTCCCAC |
| 130 | dJ222E13.2 | NR_002184 | NA | -0.158 | ACGGAAGCGCAGCCAAAAAGAGCTGCTCAA CTACGCCTGGCAGCATCGAGAGAGCAAGAT |
| 131 | FYB | NM_001465 | FYN binding protein (FYB-120/130) | 0.248 | GATCAAGAGAATATTTCAGAGTTTTGGTTT ACACATCAAGAAACAGACACACATACCTAG |
| 132 | PTPRC | NM_002838 | protein tyrosine phosphatase, receptor type, C | 0.391 | TCAATGGTCCTGCAAGTCCAGCTTTAAATC AAGGTTCATAGGAAAAGACATAAATGAGGA |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 133 | ICAM5 | NM_003259 | intercellular adhesion molecule 5, telencephalin | -0.089 | GTGAGCTAACATTTGCTAAGCACTGAATTT GTCTCAGGCACCGTGCAAGGCTCTTTACAA |
| 134 | CCRL2 | NM_003965 | chemokine (C-C motif) receptor-like 2 | 0.172 | GTGAGCTAACATTTGCTAAGCACTGAATTT GTCTCAGGCACCGTGCAAGGCTCTTTACAA |
| 135 | CCR5 | NM_000579 | chemokine (C-C motif) receptor 5 | 0.177 | AACAGTAGCATAGGACCCTACCCTCTGGGC CAAGTCAAAGACATTCTGACATCTTAGTAT |
| 136 | CLIC2 | | chloride intracellular channel 2 | 0.276 | GAGAGTGAGCATATCAGAGAGGCAAATTCT TAAAGAATGATTTTTAAAATCAGCTCTAGG |
| 137 | WNT11 | NM_004626 | wingless-type MMTV integration site family, member 11 | -0.449 | TTTGCTTTTTCTTCCTTTGGGATGTGGAAG CTACAGAAATATTTATAAAACATAGCTTTT |
| 138 | SAMSN1 | NM_022136 | SAM domain, SH3 domain and nuclear localisation signals, 1 | 0.615 | CTCTGGTTGCTATATCTCATCAGGAAATTC AGATAATGGCAAGAGGATCTGGAGTCTGA |
| 139 | PRLR | NM_000949 | prolactin receptor | -0.087 | CTCTTGTTATCATCAGGTTCACATTAAAAA CAGATACTTACAAACTGACTTGAAGCACAG |
| 140 | LRRC18 | NM_001006939 | leucine rich repeat containing 18 | -0.271 | ACAGGAAACCAAGGGCTCCCCTGTGGCTGC AGCAGCTCTTTCAGCCAAGCCCATAAAACT |
| 141 | LOXL4 | NM_032211 | lysyl oxidase-like 4 | -0.227 | GTCTCAACCAAGTGTCTGAAGTGAACTTTG CATTGAATAAATTTTTGCCATGGAAAGAAC |
| 142 | CD3G | NM_000073 | CD3g molecule, gamma (CD3-TCR complex) | 0.109 | GTTCCCAGAGATGACAAATGGAGAAGAAAG GCCATCAGAGCAAATTTGGGGGTTTCTCAA |
| 143 | RAB2 | NM_002865 | RAB2, member RAS oncogene family | 0.345 | ACACTACAAAGTCATCTTGAGTATTTTAAA TCGGTTTGTGTAGTTAGGTTTCCCAACATC |
| 144 | NPDC1 | NM_015392 | neural proliferation, differentiation and control, 1 | -0.511 | CACTAAAAACATGTTTTGATGCTGTGTGCT TTTGGCTGGGCCTCGGGCTCCAGGCCCTGG |
| 145 | AMACR | NM_014324 | alpha-methylacyl-CoA racemase | -0.114 | ACGAGCTGCTGATCAAAGGACTTGGACTAA AGTCTGATGAACTTCCCAATCAGATGAGCA |
| 146 | PRAME | | preferentially expressed antigen in melanoma | 0.032 | GTGATGAACCCCTTGGAAACCCTCTCAATA ACTAACTGCCGGCTTTCGGAAGGGGATGTG |
| 147 | CCR2 | NM_000647 | chemokine (C-C motif) receptor 2 | 0.553 | ATGAAGTCATGCGTTTAATCACATTCGAGT GTTTCAGTGCTTCGCAGATGTCCTTGATGC |
| 148 | SLC25A22 | NM_024698 | solute carrier family 25 (mitochondrial carrier: glutamate), member 22 | -0.308 | TTTTTTCTTTTGAAGAGTTTTAAGAAGTTG TAACTTTTTGTGTCTTGTCATGTCAGAGAA |
| 149 | MC1R | NM_002386 | melanocortin 1 receptor (alpha melanocyte stimulating hormone receptor) | -0.401 | CAGTCGCCCAAGCAGACAGCCCTGGCAAAT GCCTGACTCAGTGACCAGTGCCTGTGAGCA |
| 150 | RHOD | NM_014578 | ras homolog gene family, member D | -0.091 | TCATCGTCGTGGGCTGCAAGACTGACCTGC GCAAGGACAAATCACTGGTGAACAAGCTCC |
| 151 | FCGR3B | NM_000570 | Fc fragment of IgG, low affinity IIIb, receptor (CD16b) | 0.368 | TGGTGATGGTACTCCTTTTTGCAGTGGACA CAGGACTATATTTCTCTGTGAAGACAAACA |
| 152 | SAMM50 | NM_015380 | sorting and assembly machinery component 50 homolog (S. cerevisiae) | -0.130 | CTTTGGAGAACTTTTCCGAACACACTTCTT TCTCAACGCAGGAAACCTCTGCAACCTCAA |
| 153 | PABPC3 | NM_030979 | poly(A) binding protein, cytoplasmic 3 | -0.071 | ATTGATCAGAGACCACGAAAAGAAATTTGT GCTTCACCGAAGAAAAATATCTAAACATCG |
| 154 | CXCR4 | NM_901008540 | chemokine (C-X-C motif) receptor 4 | 0.361 | TGCTGGTTTTTCAGTTTTCAGGAGTGGGTT GATTTCAGCACCTACAGTGTACAGTCTTGT |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 155 | TMEM154 | NM_152680 | transmembrane protein 154 | 0.072 | GCATTTTCGTACATTTTAAGCAAACTAGGT TAACAACAACATAGCCTAGTCAAACTTCTC |
| 156 | MAFA | NM_201589 | v-maf musculoaponeurotic fibrosarcoma onoogene homolog A (avian) | -0.224 | GTTCGAGGTGAAGAAGGAGCCTCCCGAGGC CGAGCGCTTCTGCCACCGCCTGCCGCCAGG |
| 157 | PAX8 | NM_003466 | paired box gene 8 | 0.590 | CAAGCTTCCTTCTTTCTAACCCCCAGACTT TGGCCTCTGAGTGAAATGTCTCTCTTTGCC |
| 158 | LIN7A | NM_004664 | lin-7 homolog A (C. elegans) | -0.265 | TTGAGGGAAAGCTACTTGATCAAACATCCG ATAGTCACAAATTTGAAACCGTGCTTCAGA |
| 159 | CRTAM | NM_019604 | cytotoxic and regulatory T cell molecule | 0.168 | AAGCAGAATAGATGTTTGTTTTTCTAGTGG TTATACCAAGCTATACTTCCTGTTTTCACG |
| 160 | SLC22A5 | NM_003060 | solute carrier family 22 (organic cation transporter), member 5 | 0.018 | TTCAGAGTAGCTCACTTTAGTCCTGTAACT TTATTGGGTGATATTTTGTGTTCAGTGTAA |
| 161 | LOC402176 | NM_001011538 | NA | 0.308 | ATGAACACAAAGGGGGAAGAGGAGAGGCAC CGGTATACATTCTCTAGGCCTTTTAGAAAA |
| 162 | EBI2 | NM_004951 | Epstein-Barr virus induced gene 2 (lymphocyte-specific G protein-coupled receptor) | 0.510 | CTGAAACGGCAAGTCAGTGTATCGATTTCT AGTGCTGTGAAGTCAGCCCCTGAAGAAAAT |
| 163 | REEP4 | NM_025232 | receptor accessory protein 4 | -0.231 | CCACATGCAGGGATGCACCCACAATGTACC AAAGCAGGCTGGGCCCAGGGTTCTATTTAT |
| 164 | KIAA1946 | NM_177454 | KIAA1946 | -0.627 | TTTGAATCCTCTGGTATCAATACGTATTAT AGGGTTTTAGAGATCTGTGGGTCAAATGAT |
| 165 | PABPC1 | NM_002568 | poly(A) binding protein, cytoplasmic 1 | -0.077 | TGTTCCAACTGTTTAAAATTGATCAGGGAC CATGAAAAGAAACTTGTGCTTCACCGAAGA |
| 166 | LOC652106 | XM_941436 | NA | 0.749 | CTCCAGGGAAGGGGCTGGAGTGGGTTTCAT ACATTAGTAGTAGTAGTAGTACCATATACT |
| 167 | IGLL1 | NM_020070 | immunoglobulin lambda-like polypeptide 1 | 0.916 | TCCAAGCCAACAAGGCTACACTGGTGTGTC TCATGAATGACTTTTATCCGGGAATCTTGA |
| 168 | MEG3 | NR_002766 | maternally expressed 3 | -1.459 | CCGCAGGAACCCTGAGGCCTAGGGGAGCTG TTGAGCCTTCAGTGTCTGCATGTGGGAAGT |
| 169 | PEPD | NM_000285 | peptidase D | -0.032 | ATGCTGTTCTTTAGTAGCAACTAAAATGTG TCTTGCTGTCATTTATATTCCTTTTCCCAG |
| 170 | OAT | NM_000274 | ornithine aminotransferase (gyrate atrophy) | 0.162 | TAATGTAATGGCATCTATATTCAGTTGAAG TGTTTTGATGTGCATGTGTACTTCCTAAGG |
| 171 | FBXL13 | NM_145032 | F-box and leucine-rich repeat protein 13 | -0.059 | ATGCCATTACCTGCACATTTTGGATATCTC TGGTTGTGTCTTGCTTACTGACCAAATCCT |
| 172 | IFI6 | NM_002038 | interferon, alpha-inducible protein 6 | 0.056 | AGTAGCCAGCAGCTCCCAGAACCTCTTCTT CCTTCTTGGCCTAACTCTTCCAGTTAGGAT |
| 173 | IL2RB | NM_000878 | interleukin 2 receptor, beta | 0.248 | TTGAGGTTGTCTGAGTCTTGGGTCTATGCC TTGAAAAAGCTGAATTATTGGACAGTCTC |
| 174 | PRKAB2 | NM_005399 | protein kinase, AMP-activated, beta 2 non-catalytic subunit | 0.111 | GGGAATTAAATATGTGAGTCCTCTTTTTAA TGGTGCTTTTTGTAACCTTTAATGCTGAGG |
| 175 | FKSG44 | NM_031904 | NA | 0.057 | ACTCATTCTTTGAATGTTCTCATTCTTTTG TATCATGTGACTTATTAAAATCAGTTTCTA |
| 176 | TPD52 | NM_001025252 | tumor protein D52 | 0.111 | AACTGCTTACTCAACACTACCACTTTTCC TTATACTGTATATGATTATGGCCTACAATG |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 177 | RIMS2 | NM_014677 | regulating synaptic membrane exocytosis 2 | -0.668 | GATGAACTAGAGCTATCCAATATGGTGATT GGATGGTTCAAACTTTTCCCACCTTCCTCC |
| 178 | APCDD1 | NM_153000 | adenomatosis polyposis coli down-regulated 1 | -0.621 | GTTTTATATGCTGGAATCCAATGCAGAGTT GGTTTGGGACTGTGATCAAGACACCTTTTA |
| 179 | Rgr | NM_153615 | NA | 0.121 | CCATGGGACTTTTGTGAGTCAGGCGGGAGA CCATTTTATGTTTATTTTCTTTAGTGTATA |
| 180 | C2orf27 | NM_013310 | chromosome 2 open reading frame 27 | -0.120 | GGATTTATTTATAGCTTAACTAAGAATTTC AAATTTCTACCACAACACTGAAATAAAGTT |
| 181 | TRAK1 | NM_001042646 | trafficking protein, kinesin binding 1 | 0.576 | TAAGAAACATCAACCAGGTTGTCAAGCAGA GATCTCTGACCCCTTCTCCCATGAACATCC |
| 182 | MMP11 | NM_005940 | matrix metallopeptidase 11 (stromelysin 3) | -0.602 | GGCCAAAAAGTTCACAGTCAAATGGGGAGG GGTATTCTTCATGCAGGAGACCCCAGGCCC |
| 183 | COL6A3 | NM_004369 | collagen, type VI, alpha 3 | 0.054 | GACCCTCGCTCTCTGTCTCCAGCAGTTCTC TCGAATACTTTGAATGTTGTGTAACAGTTA |
| 184 | UTX | NM_021140 | ubiquitously transcribed tetratricopeptide repeat, X chromosome | 0.182 | AATGCTGTTATTTTTTCCAGATTTACCTGC CATTGAAATTTTAAGGAGTTCTGTAATTTC |
| 185 | PCSK5 | NM_006200 | proprotein convertase subtilisin/kexin type 5 | -0.248 | TGCCAACGGAAGGTTCTTCAACAACTTTGC TGCAAAACATGTACATTTCAAGGCTGAGCA |
| 186 | AYTL1 | NM_017839 | acyltransferase like 1 | -0.057 | GAAGAATTCGCCAAGTATTTAAAGTTGCCT GTTTCAGATGTCTTGAGACAACTTTTTGCA |
| 187 | RNF13 | NM_007282 | ring finger protein 13 | 0.357 | CTGTCTCATCTTGATAGTCATTTTCATGAT CACAAAATTTTTCCAGGATAGACATAGAGC |
| 188 | CTA-126B4.3 | NM_015703 | NA | -0.285 | TGCTGTGATTGTATCCGAAGTAGTCCTCGT GAGAAAAGATAATGAGATGACGTGAGCAGC |
| 189 | LRAT | NM_004744 | lecithin retinol acyl-trans-ferase (phospha-tidylcholine-retinol O acyltransferase) | 0.130 | AGGAAGAGTCAACAGACTTTAGCAAAATCC TTTTATTTGATTCATGCATAACTCCTGATG |
| 190 | C9orf127 | NM_001042589 | chromosome 9 open reading frame 127 | -0.270 | AGCCTTCCCAAGACATGGATTCCTTCCCAG GGAGACAAAGCCCTGTCAGGAGCACAGCAT |
| 191 | LCOR | NM_032440 | ligand dependent nuclear receptor corepressor | -0.038 | TTCATGTCTGTGAAGCTTTTAAACATTACA CTTGAGATCAGTCATGACTTGATATTCAGG |
| 192 | SPN | NM_001030288 | sialophorin (leukosialin, CD43) | 0.682 | TCCTCACCCACCTCTTCACTCTGAATCCTC ATGAGGCTTCTCAGCCCTGGATTTCCTGCT |
| 193 | CAMK2N1 | NM_018584 | calcium/calmodulin-dependent protein kinase II inhibitor 1 | -0.750 | TGTTATTGAAGATGATAGGATTGATGACGT GCTGAAAAATATGACCGACAAGGCACCTCC |
| 194 | BCL2A1 | NM_004049 | BCL2-related protein A1 | -0.069 | TGTAACCATATTTGCATTTGAAGGTATTCT CATCAAGAACTTCTACGACAGCAAATTGC |
| 195 | TP53TG3 | NM_016212 | NA | -0.389 | TCTTGTGTATTTATTACATTTTCACGTGTC TTCACGCATCTCTTGAATTGGAAATTGTGC |
| 196 | CD247 | NM_000734 | CD247 molecule | 0.321 | CAAAGTGGCATAAAAAACATGTGGTTACAC AGTGTGAATAAAGTGCTGCGGAGCAAGAGG |
| 197 | MAP1B | NM_005909 | microtubule-associated protein 1B | -0.775 | TTGCAGTAATGATATTTATTAAAAACCCAT AACTACCAGGAATAATGATACCTCCCACCC |
| 198 | CREB3 | NM_006368 | cAMP responsive element binding protein 3 | -0.079 | GAGGGGCTTATTCTGCCTGAGACACTTCCT CTCACTAAGACAGAGGAACAAATTCTGAAA |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 199 | FLJ20054 | NM_019049 | NA | 0.206 | GGTACTAGTTTGTATGTATGTTTAAAGTAT GTATTGACCATGAGATTTCCCAGTGTTTGG |
| 200 | ACSL1 | NM_001995 | acyl-CoA synthetase long-chain family member 1 | 0.806 | ACTCGGTTCTCCAGGCCTGATTCCCCGACT CCATCCTTTTTCAGGGTTATTTAAAAATCT |
| 201 | GIMAP2 | NM_015660 | GTPase, IMAP family member 2 | 0.518 | ATGACCAAGTGAAGGAACTAATGGACTGTA TTGAGGATCTGTTGATGGAGAAAAATGGTG |
| 202 | IGHG1 | | immunoglobulin heavy constant gamma 1 (G1m marker) | 0.296 | GTTGGACCACAAACTATGCACAGAAGTTTC AGGGGAAGGTCACCATGACCAAGGACACGT |
| 203 | MAZ | NM_001042539 | MYC-associated zinc finger protein (purine-binding transcription factor) | -0.413 | GCTGTGCACCTTCATGTGGTCCGAAATATA AGCCGAGCTCAGCATCTTGCCACACACGTG |
| 204 | LOC648674 | XM_937741 | NA | 0.027 | CTCATAAGTGGGGCTATACTGTGAAGGGCA TTCAGAAATACAAAGCAAAGGTTATTTCCG |
| 205 | P2RY8 | NM_178129 | purinergic receptor P2Y, G-protein coupled, 8 | 0.483 | AACACAGGTCTATTGACTCACACACATGTT TTAAGATGGAAAACTTTACTTCTGTTCTTG |
| 206 | TMEM158 | NM_015444 | transmembrane protein 158 | -0.304 | CCAACGCGGACGGCCGCGCTTTCTTCGCCG CCGCCTTCCACCGCGTCGGGCGCCGCTGC |
| 207 | RAB1A | NM_004161 | RAB1A, member RAS oncogene family | 0.637 | CAAAATAAGAACTATAGAGTTAGACGGGAA AACAATCAAGCTTCAAATATGGGACACAGC |
| 208 | LOC399959 | NA | NA | 0.029 | CATTTCTAACAAGCATCTTCTTAACCAACT TTATGCACAGTGTATGTTTGTAAGTGCTTC |
| 209 | LMAN1 | NM_005570 | lectin, mannose-binding, 1 | 0.794 | TTGACTACCATTTTCCTGTGTACTTCATCT ATTTGTGTACAAAATGATGTCGTTTTGAGG |
| 210 | OPHN1 | NM_002547 | oligophrenin 1 | 0.096 | TTATCATGGGAAAGTATTCTCTTTTCAAGA AGTTCTTTGATTCTGTAATAACTAGAACAA |
| 211 | SGK3 | NM_001033578 | serum/glucocorticoid regulated kinase family, member 3 | 0.239 | GTATGTCTTGAGAAAGAAATCACAGAAGCA TTTCTCACCAATACTCTTTGGCTTAAAATG |
| 212 | DUSP15 | NM_001012644 | dual specificity phosphatase 15 | -0.314 | AAGCGCTGCCGGCAGGGCTCCGCGACCTCG GCCTCCTCCGCCGGGCCGCACTCAGCAGCC |
| 213 | DEAF1 | NM_021008 | deformed epidermal autoregulatory factor 1 (Drosophila) | -0.251 | CGGGCACATGGACATGGGCGCCGAGGCCCT GCCCGGCCCCGACGAGGCCGCCGCTGCCGC |
| 214 | NEUROG3 | NM_020999 | neurogenin 3 | 0.156 | CATTCAAAGAATACTAGAATGGTAGCACTA CCCGGCCGGAGCCGCCCACCGTCTTGGGTC |
| 215 | TLX2 | NM_016170 | T-cell leukemia homeobox 2 | -0.261 | ACGGAGCCTCGGGCTACGGTCCCGCCGGCT CACTTGCCCCGCTGCCCGGCAGCTCCGGAG |
| 216 | LAMC1 | NM_002293 | laminin, gamma 1 (formerly LAMB2) | 0.040 | ACCTTAATTACACTCCCGCAACACAGCCAT TATTTTATTGTCTAGCTCCAGTTATCTGTA |
| 217 | NKI | | | -0.145 | #N/A |
| 218 | BBS2 | NM_031885 | Bardet-Biedl syndrome 2 | 0.025 | TGGGGACAGCTTCTTCCTAGGTGAGGAAAA TACAGGTCATGAAGTTCCTGGCAAAGATTT |
| 219 | CKB | NM_001823 | creatine kinase, brain | -0.193 | AGAAATGAAGCCCGGCCCACACCCGACACC AGCCCTGCTGCTTCCTAACTTATTGCCTGG |
| 220 | LOC389199 | NM_203423 | NA | -0.310 | CCCGCCCCACGAGTGGGTCTTCGCAGGGCC CCTCTGACGCACACGGGGACCAGCCACGC |
| 221 | SALL1 | NM_002968 | sal-like 1 (Drosophila) | -0.373 | CCTCAGTGATGCATTAGATCTCTAATAAAG TCTGTATATACATGTACACTTTGATCCTGC |

TABLE 3-continued

NSCLC associated genes. Genes are ranked according to their association with recurrence-free survival. The low-risk profile column provides the log2 ratios of each classifier gene in a low-risk profile.

| SEQ ID NO: | Gene | Refseq | Description | low-risk profile | Sequence |
|---|---|---|---|---|---|
| 222 | ANKRD20A2 | NM_001012421 | ankyrin repeat domain 20 family, member A2 | -0.043 | AGACGGTCAGCTCTCATGCTTGCTGTATAC TATGACTCACCAGGTATTGTCAGTATCCTT |
| 223 | FOXC2 | NM_005251 | forkhead box C2 (MFH-1, mesenchyme forkhead 1) | -0.202 | TCAACCACAGCGGGGACCTGAACCACCTCC CCGGCCACACGTTCGCGGCCCAGCAGCAAA |
| 224 | SMEK2 | NM_020463 | NA | 0.259 | TGTGGAAGATACTTTGAAATCACTTTCTAC TTTGTTAGTAAAGTTCTGTCTTTCCAGAGC |
| 225 | CYP2R1 | NM_024514 | cytochrome P450, family 2, subfamily R, polypeptide 1 | 0.172 | CTCATCTGTGCTGAAAGACGCTGAAACTGC CTGGGATGTTTTCGGGAACAAGAATGTATA |
| 226 | ZNF205 | NM_001042428 | zinc finger protein 205 | -0.315 | TACGTGTGCGACCGCTGCGCCAAGCGCTTC ACCCGCCGCTCGGACTTGGTCACCCACCAG |
| 227 | ATP5L | NM_006476 | ATP synthase, H+ transporting, mitochondrial F0 complex, subunit G | 0.176 | ACACGTCTGTTTAGCCCGCAATTGGAAAGG ATATATGTGGCAATATTAACCTGGTACATG |
| 228 | FANCC | NM_000136 | Fanconi anemia, complementation group C | 0.016 | CTATTTGCGACACGAACTGTGCCCAATGTG TGCCCAAGGACAAGGCTATTAACAAATTCA |
| 229 | ZDHHC4 | NM_018106 | zinc finger, DHHC-type containing 4 | -0.128 | CTTCGGAGCAACCTTCAAGAGATCTTTCTA TCCTGCCTTCCATGTCATGAGAGGAAGAAA |
| 230 | PRR5 | NM_001017528 | proline rich 5 (renal) | -0.382 | AAAGCGCCTCCTCCGCCGCTCCCGCTCGGG GGACGTGCTGGCCAAGAACCCTGTGGTGCG |
| 231 | MIER2 | NM_017550 | mesoderm induction early response 1, family member 2 | 0.333 | CATCCCTCACCCCACCAAGGACCACACTGT GAAGTGATAACTGCCTTGAACCCCCCTTTG |
| 232 | NT5C2 | NM_012229 | 5'-nucleotidase, cytosolic II | 0.278 | CGTTGCTTTAGGGCAGGATTCTATTTTGAG GGAAAAGACAGTATCCTTATTACCTTTTGT |
| 233 | BEX1 | NM_018476 | brain expressed, X-linked 1 | -2.105 | TGAACCAGTCTGTAAGATTTTTGTTAGCAG AAGAATTTTACCTATTGCATGGAAAGATGC |
| 234 | OSTalpha | NM_152672 | NA | 0.038 | ACGAATGTACTACCGAAGGAAAGACCACAA GGTTGGGTATGAAACTTTCTCTTCTCCAGA |
| 235 | TMSL3 | NM_183049 | thymosin-like 3 | 0.557 | CTTTTAGCTGTTTAACTTTGTAAGATGCAA AGAGGTTGGATCAAGTTTAAATGACTGTGC |
| 236 | CCL3 | NM_002983 | chemokine (C-C motif) ligand 3 | 0.003 | TGGGAAACATGCGTGTGACCTCCACAGCTA CCTCTTCTATGGACTGGTTGTTGCCAAACA |
| 237 | CSF3 | NM_000759 | colony stimulating factor 3 (granulocyte) | 0.195 | GGGTCCCACGAATTTGCTGGGGAATCTCGT TTTTTCTCTTAAGACTTTTGGGACATGGTT |

TABLE 4

Univariate and multivariate analysis for overall and relapse-free survival

| | Cox-Ranked Univariate | | | Cox-Ranked Multivariate | | |
|---|---|---|---|---|---|---|
| | Hazard ratio | (95% CI) | P-value | Hazard ratio | (95% CI) | P-value |
| Overall survival | | | | | | |
| 72-gene classifier (low-risk vs. high-risk) | 4.83 | (2.47-9.44) | 4.1E-06 | 4.70 | (2.40-9.21) | 6.4E-06 |
| Histology (squamous, adeno or other) | 0.82 | (0.55-1.21) | 0.31 | 0.89 | (0.57-1.40) | 0.62 |
| Tumor Stage (Grade I vs. II) | 2.22 | (1.27-3.88) | 0.0049 | 2.13 | (1.21-3.73) | 0.0084 |

TABLE 4-continued

Univariate and multivariate analysis for overall and relapse-free survival

| | Cox-Ranked Univariate | | | Cox-Ranked Multivariate | | |
|---|---|---|---|---|---|---|
| | Hazard ratio | (95% CI) | P-value | Hazard ratio | (95% CI) | P-value |
| Relapse-free survival | | | | | | |
| 72-gene classifier (low-risk vs. high-risk) | 4.86 | (2.49-9.50) | 3.7E−06 | 4.61 | (2.36-9.03) | 8.4E−06 |
| Histology (squamous, adeno or other) | 0.79 | (0.53-1.18) | 0.25 | 0.87 | (0.55-1.37) | 0.54 |
| Tumor Stage (Grade I vs. II) | 2.27 | (1.30-3.97) | 0.004 | 2.08 | (1.19-3.64) | 0.011 |
| 72-gene classifier & Tumor Stage | | | | Overall survival | | 6.2E−08 |
| | | | | Relapse-free survival | | 3.3E−07 |

The invention claimed is:

1. A method for typing a sample of a human individual suffering from stage I or stage II non-small cell lung cancer (NSCLC) as indicating a low risk or high risk of recurrence of NSCLC within three years from identification of said NSCLC in said individual, the method comprising
a) providing a lung tissue sample from said individual comprising non-small cell lung cancer cells or suspected to comprise non-small cell lung cancer cells;
b) preparing RNA from said tissue sample;
c) determining RNA levels for a set of genes in said RNA; and
d typing said sample as indicating a low risk or high risk of recurrence of NSCLC within three years from identification of said NSCLC in said individual on the basis of the levels of RNA determined for said set of genes, wherein said set of genes comprises at least two of the genes indicated by SEQ ID NOS. 1-216 and 218-237 in Table 3.

2. The method according to claim 1, wherein typing said samples on the basis of the RNA levels determined for said set of genes comprises comparing the RNA levels of the genes indicated by SEQ ID NOS: 1-216 and 218-237 to the RNA levels of said genes in a reference sample.

3. The method according to claim 1, whereby one of said genes indicated by SEQ ID NOS: 1-216 and 218-237 is induced in a low risk NSCLC sample, compared to the average level of expression of said gene in a reference sample, while a second gene from said genes indicated by SEQ ID NOS: 1-216 and 218-237 is repressed in a low risk NSCLC sample compared to the average level of expression of said gene in a reference sample.

4. The method according to claim 1, whereby said set of genes comprises SEQ ID NOS: 1-72.

5. The method according to claim 1, further comprising normalizing the determined RNA levels of said set of genes in said sample.

6. A method of classifying a sample from a human individual suffering from non-small cell lung cancer (NSCLC), comprising
classifying a sample as derived from a human individual having a low risk of recurrence of NSCLC within three years from indentification of said NSCLC in said individual, or as derived from an individual having a high risk of recurrence of NSCLC within three years from identification of said NSCLC in said individual by a method comprising
providing a lung tissue sample from said individual, wherein the sample comprises stage I or stage II NSCLC cells or is suspected to comprise stage I or stage II NSCLC cells;
determining a level of RNA for a set of genes comprising at least two of the genes indicated by SEQ ID NOS: 1-216 and 218-237 in Table 3 in said sample;
determining a similarity value for the level of RNA in said sample and a level of RNA for said set of genes in a patient having a low risk of recurrence of NSCLC within three years from identification of said NSCLC in said individual; and
classifying said individual as having a low risk of recurrence of NSCLC within three years from identification of said NSCLC in said individual if said similarity value exceeds a first similarity threshold value, and classifying said individual as having a high risk of recurrence of NSCLC within three years of identification of said NSCLC in said individual if said similarity value is below said first similarity threshold value.

7. The method according to claim 3, wherein the one gene listed in Table 3 is C3orf41 indicated by SEQ ID NO: 1, while the second gene listed in Table 3 is C1orf24, indicated by SEQ ID NO: 2.

* * * * *